(12) United States Patent
Tanabe et al.

(10) Patent No.: US 10,135,004 B2
(45) Date of Patent: *Nov. 20, 2018

(54) FLUORESCENT ORGANIC LIGHT EMITTING ELEMENTS HAVING HIGH EFFICIENCY

(71) Applicant: UDC IRELAND LIMITED, Dublin (IE)

(72) Inventors: Junichi Tanabe, Hyogo (JP); Christian Lennartz, Schifferstadt (DE)

(73) Assignee: UDC IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/846,655

(22) Filed: Dec. 19, 2017

(65) Prior Publication Data

US 2018/0114925 A1   Apr. 26, 2018

Related U.S. Application Data

(63) Continuation of application No. 15/301,863, filed as application No. PCT/EP2015/056892 on Mar. 30, 2015, now Pat. No. 9,853,224.

(30) Foreign Application Priority Data

Apr. 4, 2014 (EP) .................................... 14163538

(51) Int. Cl.

| C07D 401/14 | (2006.01) |
| H01L 51/00 | (2006.01) |
| C07D 413/14 | (2006.01) |
| C07D 401/04 | (2006.01) |
| C07D 401/10 | (2006.01) |
| C07D 403/04 | (2006.01) |
| C07D 403/10 | (2006.01) |
| C07D 403/14 | (2006.01) |
| C07D 413/04 | (2006.01) |
| C07D 413/10 | (2006.01) |
| C07D 417/04 | (2006.01) |
| C07D 417/10 | (2006.01) |
| C07D 417/14 | (2006.01) |
| C07D 249/20 | (2006.01) |
| C07D 249/22 | (2006.01) |
| C07D 487/04 | (2006.01) |
| C09K 11/06 | (2006.01) |
| H01L 51/50 | (2006.01) |

(Continued)

(52) U.S. Cl.
CPC ........ *H01L 51/0072* (2013.01); *C07D 249/20* (2013.01); *C07D 249/22* (2013.01); *C07D 401/04* (2013.01); *C07D 401/10* (2013.01); *C07D 401/14* (2013.01); *C07D 403/04* (2013.01); *C07D 403/10* (2013.01); *C07D 403/14* (2013.01); *C07D 413/04* (2013.01); *C07D 413/10* (2013.01); *C07D 413/14* (2013.01); *C07D 417/04* (2013.01); *C07D 417/10* (2013.01); *C07D 417/14* (2013.01); *C07D 487/04* (2013.01); *C09B 15/00* (2013.01); *C09B 17/00* (2013.01); *C09B 19/00* (2013.01); *C09B 21/00* (2013.01); *C09B 57/00* (2013.01); *C09B 57/008* (2013.01); *C09K 11/02* (2013.01); *C09K 11/025* (2013.01); *C09K 11/06* (2013.01); *H01L 51/00* (2013.01); *H01L 51/0071* (2013.01); *H01L 51/50* (2013.01); *H05B 33/14* (2013.01); *H05K 999/00* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *H01L 51/0054* (2013.01); *H01L 51/0067* (2013.01); *H01L 51/5012* (2013.01); *H01L 51/5028* (2013.01); *H01L 2251/552* (2013.01); *Y02E 10/549* (2013.01)

(58) Field of Classification Search
CPC .. C07D 401/14; C07D 413/04; C07D 413/14; C07D 417/14; C09K 11/02; C09K 11/025; C09K 11/06; H01L 51/0072; H01L 51/0071
USPC ........................................................ 544/43
See application file for complete search history.

(56) References Cited

U.S. PATENT DOCUMENTS 4,533,612 A    8/1985  Eilingsfeld
9,853,224 B2 * 12/2017 Tanabe ................ H01L 51/0072

FOREIGN PATENT DOCUMENTS

EP    0418386 A1   3/1991
EP    1097981 A2   5/2001
(Continued)

OTHER PUBLICATIONS

Ichikawa et al., "Bipyridyl-substituted benzo [1,2,3]triazoles as a thermally stable electron transporting material for organic light-emitting devices", J. Mater. Chem, 2011. 21:11791-11799.
Xu et al., "Porphyrins with Four Monodisperse Oligocarbazole Arms: Facile Synthesis and Photophysical Properties" J. Org. Chem, 2008, 73, 1809-1817.
Endo, et al., "Efficient up-conversion of triplet excitors into a singlet state and its application for organic light emitting diodes". Appl. Phys. Lett, 2011. 98:083302.

(Continued)

*Primary Examiner* — Kahsay Habte
(74) *Attorney, Agent, or Firm* — Riverside Law LLP

(57) ABSTRACT

The present invention relates to organic light emitting elements, comprising thermally activated delayed fluorescence (TADF) emitters and/or hosts on basis of benzotriazoles, which have a sufficiently small energy gap between $S_1$ and $T_1$ ($\Delta E_{ST}$) to enable up-conversion of the triplet exciton from $T_1$ to $S_1$. The organic light emitting elements show high electroluminescent efficiency.

22 Claims, 2 Drawing Sheets

Figure 1:
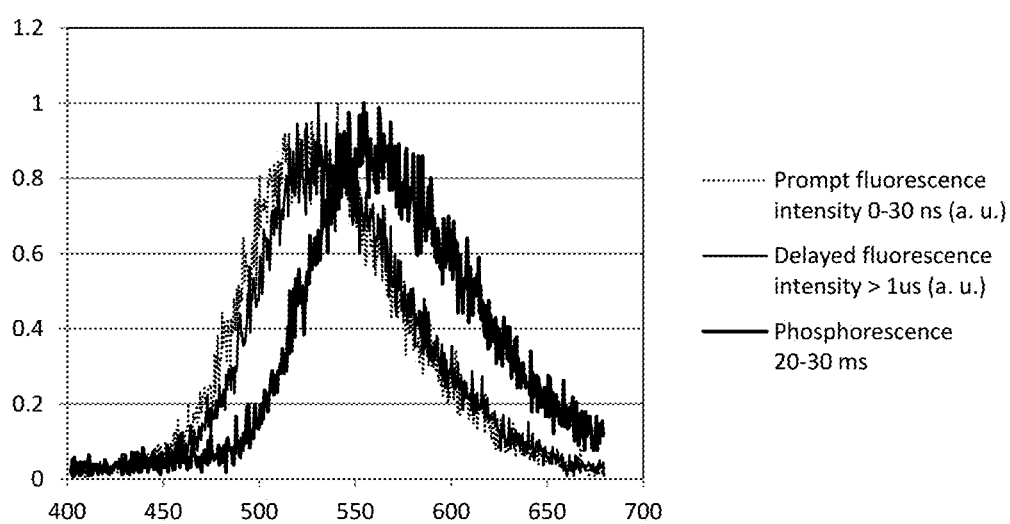

(51) Int. Cl.
*H05B 33/14* (2006.01)
*C09K 11/02* (2006.01)
*C09B 15/00* (2006.01)
*C09B 17/00* (2006.01)
*C09B 19/00* (2006.01)
*C09B 21/00* (2006.01)
*C09B 57/00* (2006.01)

(56) References Cited

FOREIGN PATENT DOCUMENTS

| | | |
|---|---|---|
| EP | 1786050 A1 | 5/2007 |
| EP | 1970371 A1 | 9/2008 |
| EP | 2128216 A1 | 12/2009 |
| EP | 2265092 A1 | 12/2010 |
| WO | 03105538 A1 | 12/2003 |
| WO | 2005054212 A2 | 6/2005 |
| WO | 2013054764 A1 | 4/2013 |

OTHER PUBLICATIONS

Haneder, et al., "Controlling the Radiative Rate of Deep-Blue Electrophosphorescent Organometallic Complexes by Singlet-Triplet Gap Engineering". Adv. Mater. 2008, 20:3325-3330.

Nakagawa, et al., Electroluminescence based on thermally activated delayed fluorescence generated by a spirobifluorene donor—acceptor structure. Chem. Commun., 2012. 48:9580-9582.

Endo, et al., "Thermally Activated Delayed Fluorescence from Sn4+—Porphyrin Complexes and Their Application to Organic Light-Emitting Diodes—A Novel Mechanism for Electroluminescence". Adv, Mater., 2009. 21:4802-4806.

\* cited by examiner

FLUORESCENT ORGANIC LIGHT EMITTING ELEMENTS HAVING HIGH EFFICIENCY

CROSS-REFERENCE TO RELATED APPLICATIONS

The present application is a continuation of U.S. patent application Ser. No. 15/301,863, now allowed, which is the U.S. National Stage of International Application No. PCT/EP2015/056892, filed Mar. 30, 2015, which claims the benefit of European Patent Application No. 14163538.3, filed Apr. 4, 2014, the entire contents all of which are incorporated herein by reference.

The present invention relates to organic light emitting elements, comprising thermally activated delayed fluorescence (TADF) emitters and/or hosts on basis of benzotriazoles, which have a sufficiently small energy gap between $S_1$ and $T_1$ ($\Delta E_{ST}$) to enable up-conversion of the triplet exciton from $T_1$ to $S_1$. The organic light emitting elements show high electroluminescent efficiency.

The development of OLED luminescent materials is an important issue and these materials have been classified into two major categories. The first is fluorescent materials, which can harvest only the singlet excitons (25%) that are generated by electrical excitation. The second is phosphorescent materials, which can harvest the triplet excitons generated (75%). The branching ratio of singlet and triplet excitons is 1:3. Therefore, in recent devices, phosphorescent materials and their related technologies have been indispensable to obtain high EL efficiency. However, phosphorescent materials generally contain a rare metal element such as Ir or Pt. These metals are rather expensive and are dependent on limited global resources.

Recently, the alternative concept of thermally activated delayed fluorescence (TADF) as a third generation luminescent material, instead of the conventional fluorescent and phosphorescent materials was described by C. Adachi et al. in Adv. Mater., 2009, 21, 4802; Appl. Phys. Lett., 2011, 98, 083302 and Chem. Commun., 2012, 48, 9580.

The TADF strongly depends on HOMO-LUMO separation in a single molecule. TADF materials have a sufficiently small energy gap between $S_1$ and $T_1$ ($\Delta E_{ST}$) to enable up-conversion of the triplet exciton from $T_1$ to $S_1$. This small $\Delta E_{ST}$ enables TADF materials to realize 100% of the exciton formation generated by electrical excitation at $S_1$.

WO03/105538 relates to electroluminescent devices comprising organic layers that contain certain 2H-benzotriazole compounds. The 2H-benzotriazole compounds are suitable components of blue-emitting, durable, organo-electroluminescent layers. The following compounds are explicitly mentioned:

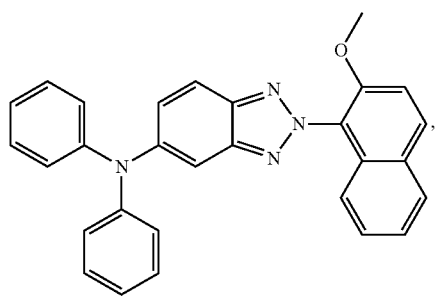

(A9)

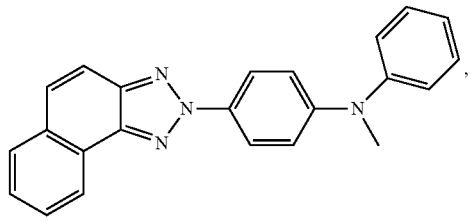

(B1)

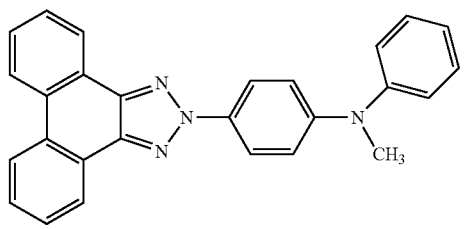

(C1)

WO2005/054212 relates among others to compounds of formula

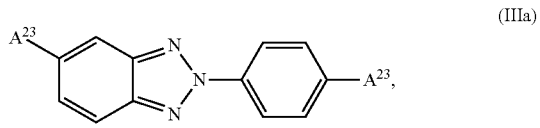

(IIIa)

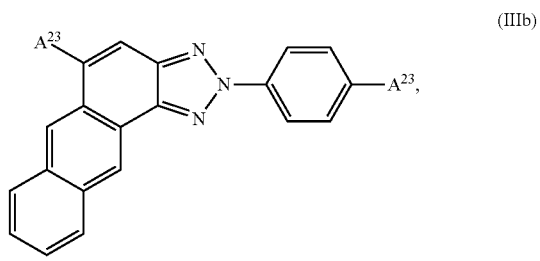

(IIIb)

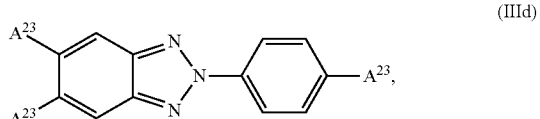

(IIId)

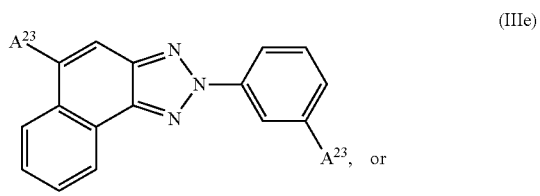

(IIIe)

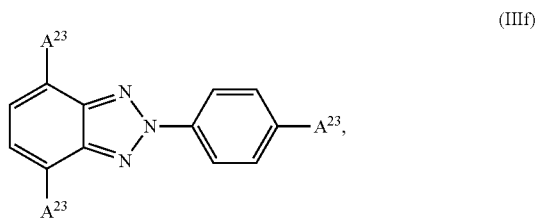

(IIIf)

especially (IIIc)

wherein $R^{102}$ is $C_1$-$C_{24}$alkyl, especially $C_1$-$C_{12}$alkyl, in particular H, $A^{23}$ is a group of formula or a group of formula especially

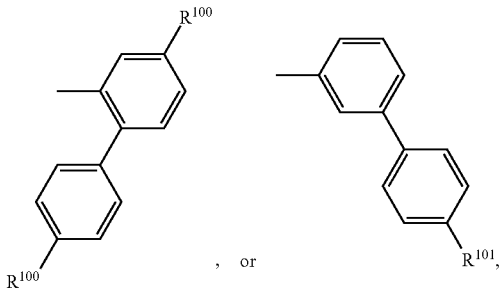

wherein $R^{100}$ and $R^{101}$ are independently of each other H, $C_1$-$C_{24}$alkyl, especially $C_1$-$C_{12}$alkyl, very especially tert-butyl, or

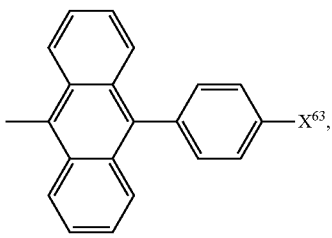

wherein $X^{51}$, $X^{52}$, $X^{53}$, $X^{63}$, $X^{64}$, $X^{65}$ and $X^{66}$ are independently of each other fluorine, $C_1$-$C_{24}$alkyl, especially $C_1$-$C_{12}$alkyl, very especially tert-butyl, $C_5$-$C_{12}$cycloalkyl, especially cyclohexyl, which can optionally be substituted by one, or two $C_1$-$C_8$alkyl groups, or 1-adamantyl, $C_1$-$C_{24}$perfluoroalkyl, especially $C_1$-$C_{12}$perfluoroalkyl, such as $CF_3$, $C_6$-$C_{14}$perfluoroaryl, especially pentafluorophenyl, $NR^{25}R^{26}$, wherein $R^{25}$ and $R^{26}$ are $C_6$-$C_{14}$aryl, especially phenyl, which can be substituted by one, or two $C_1$-$C_{24}$alkyl groups, or $R^{25}$ and $R^{26}$ together form a five or six membered heterocyclic ring, especially

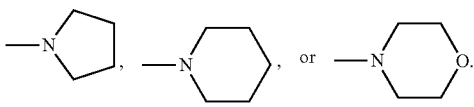

In a preferred embodiment WO2005/054212 discloses compounds of formula especially

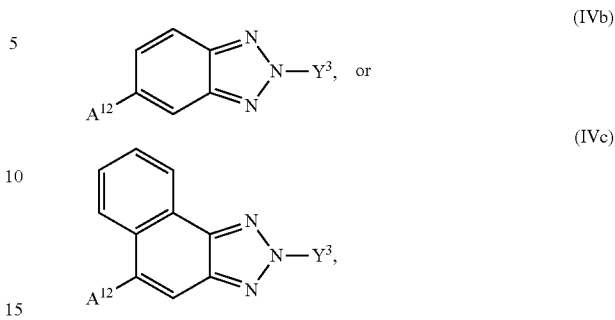

wherein
$Y^3$ is

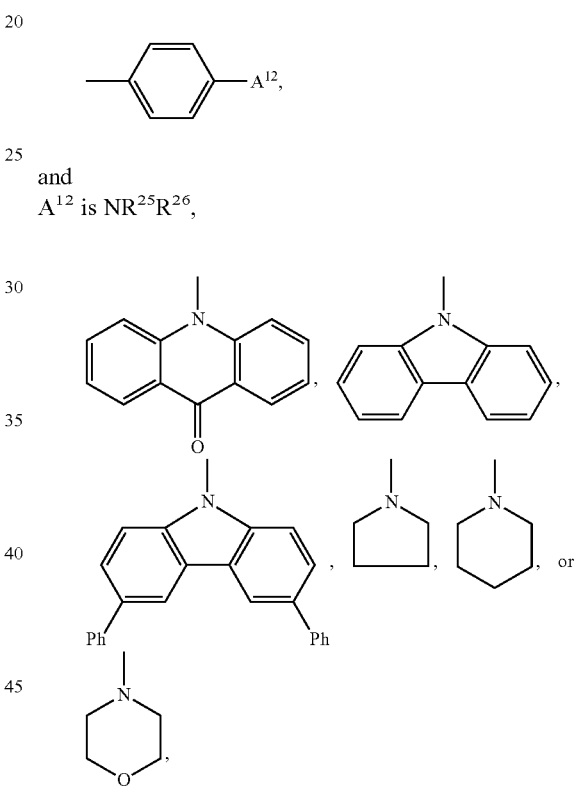

and
$A^{12}$ is $NR^{25}R^{26}$, $R^{25}$ and $R^{26}$ are $C_6$-$C_{14}$aryl, especially phenyl, 1-naphthyl, 2-naphthyl, which can optionally be substituted by one, or two $C_1$-$C_8$alkyl groups, or $C_1$-$C_8$alkoxy groups. The following compounds are explicitly mentioned:

-continued

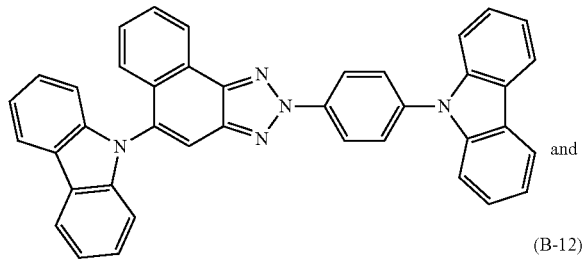
(B-10)

and

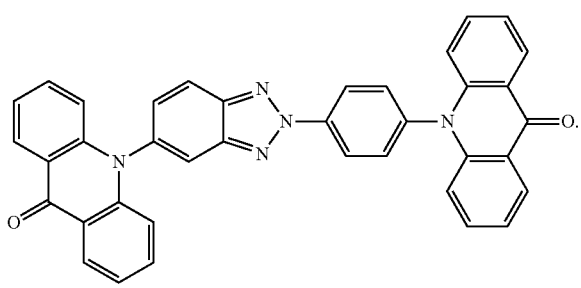
(B-12)

The 2H-benzotriazoles of WO2005/054212 are preferably used as the light emitting material in the light emitting layer, optionally as a host or guest component.

Musubu Ichikawa et al., J. Mater. Chem., 2011, 21, 11791-11799 describe new electron-transporting materials (ETMs) for organic light-emitting devices (OLEDs) based on benzo[1,2,3]triazole and two bipyridines.

WO2013/054764 relates to benzotriazole derivatives represented by formula

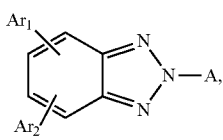
(1)

wherein $Ar_1$ and $Ar_2$ represent an aromatic hydrocarbon group, an aromatic heterocyclic group, or the like; A represents a group which includes a pyridine ring. The derivatives exhibit electron injection and transport performance, and have hole-blocking ability.

An object of the present invention is to provide a highly efficient and practically useful organic light-emitting element and an organic light-emitting material suitable for the organic light-emitting element. It has surprisingly been found that certain 2H-benzotriazole compounds emit delayed fluorescence and the use thereof in an organic light-emitting element provides a highly efficient organic EL element.

Accordingly, the present invention relates to an organic light-emitting element, comprising a light-emitting layer comprising
i) a compound of formula

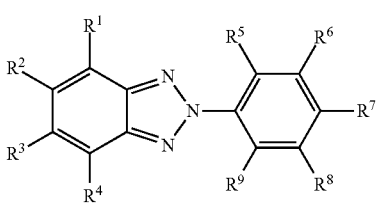
(I)

as guest and a host material; or
ii) a compound of formula

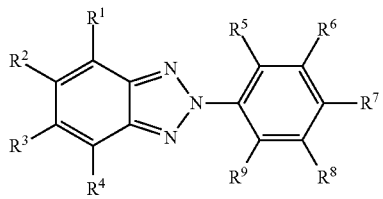
(I)

as host and a fluorescent guest material, wherein
$R^1$, $R^2$, $R^3$ and $R^4$ are independently of each other H, D, F, Cl, a $C_1$-$C_{25}$alkyl group, a $C_1$-$C_{25}$alkoxy group, a $C_6$-$C_{10}$aryloxy group, or a donor group of formula

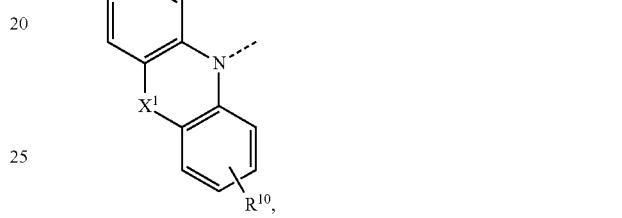
(Xa)

(Xb)

(Xc)

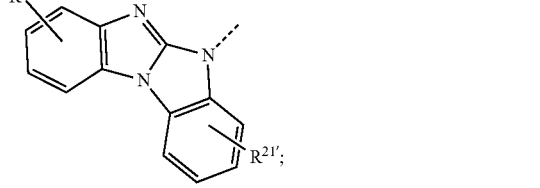
(Xd)

$R^5$, $R^6$, $R^7$, $R^8$ and $R^9$ are independently of each other H, D, F, Cl, a $C_1$-$C_{25}$alkyl group, a $C_1$-$C_{25}$alkoxy group, a $C_6$-$C_{10}$aryloxy group, a group of formula

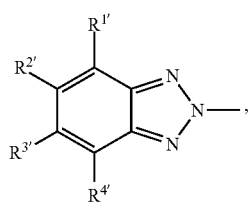

(Xa), (Xb), (Xc), or (Xd);
$R^{1'}$, $R^{2'}$, $R^{3'}$ and $R^{4'}$ are independently of each other H, D, F, Cl, a $C_1$-$C_{25}$alkyl group, a $C_1$-$C_{25}$alkoxy group, or a $C_6$-$C_{10}$aryloxy group;

$R^1$ and $R^2$ together form a group of formula

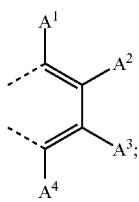

$R^{1'}$ and $R^{2'}$ together form a group of formula

$R^3$ and $R^4$ together form a group of formula

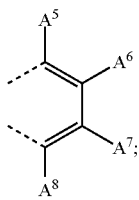

$R^{3'}$ and $R^{4'}$ together form a group of formula

$R^5$ and $R^6$ together form a group of formula

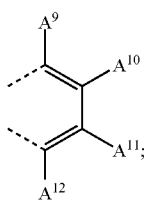

and/or
$R^8$ and $R^9$ together form a group of formula

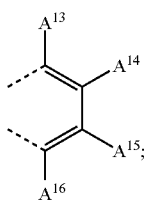

$A^1$, $A^2$, $A^3$, $A^4$, $A^5$, $A^6$, $A^7$ and $A^8$ are independently of each other H, D, F, Cl, a $C_1$-$C_{25}$alkyl group, or a donor group of formula (Xa), (Xb), (Xc), or (Xd);

$A^9$, $A^{10}$, $A^{11}$, $A^{12}$, $A^{13}$, $A^{14}$, $A^{15}$ and $A^{16}$ are independently of each other H, D, F, Cl, a $C_1$-$C_{25}$alkyl group, or a donor group of formula (Xa), (Xb), (Xc), or (Xd);

$X^1$ and $X^2$ are independently of each other a single bond, O, S, $N(R^{15})$, $C(=O)$, $C(R^{16})(R^{17})$, $B(R^{18})$, or $Si(R^{19})(R^{20})$ and $R^{10}$, $R^{11}$, $R^{12}$, $R^{13}$, $R^{21}$ and $R^{21'}$ are independently of each other H, D, F, Cl, or a $C_1$-$C_{25}$alkyl group;

$R^{14}$, $R^{15}$, $R^{16}$, $R^{17}$, $R^{18}$, $R^{19}$ and $R^{20}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group; with the proviso that at least one donor group of formula (Xa), (Xb), (Xc), or (Xd) is present in the compound of formula (I), characterized in that it emits delayed fluorescence.

The present invention is also directed to the use of compounds of formula (I) for generating delayed fluorescence emission.

E-type delayed fluorescence fluorescence is defined herein as a process in which the first excited singlet state becomes populated by a thermally activated radiationless transition from the first excited triplet state.

Thermally activated delayed fluorescence (TADF, E-type delayed fluorescence) is a promising way to obtain a high efficiency of exciton formation by converting spin-forbidden triplet excitons up to the singlet level by the mechanism of reverse intersystem crossing (RISC). In a TADF emitter, the upconversion mechanism uses the vibronic energy that, at sufficiently high temperatures (≥300 K), allows all of the excitons in an OLED to eventually produce light through singlet decay.

The organic light-emitting element offers an external quantum efficiency of more than 5%, especially more than 10% and reduced efficiency roll-off characteristics at high luminance.

The compound of formula (I) has preferably a difference between excited singlet energy and excited triplet energy ($\Delta E_{ST}$) of 0.5 eV or less, more preferably $\Delta E_{ST}$ of 0.35 eV or less, i.e. of 0.01 to 0.5 eV, especially 0.01 to 0.35 eV.

The determination of $\Delta E_{ST}$ can be carried either by quantum mechanical calculations (for example TD-DFT (time dependent density functional theory) calculations, for example with commercially available Gaussian 09 or ADF Amsterdam Density Functional software programs; for example as described in Adv. Mater. 2008, 20, 3325-3330), or experimentally.

Experimental Determination of $\Delta E_{ST}$:

i) $\Delta E_{ST}$ can be determined based on the information given in the following formula:

$$\text{Int}(S_1 \rightarrow S_0)/\text{Int}(T_1 \rightarrow T_0) = k(S_1)/k(T_1)\exp(-\Delta E/k_B T).$$

The intensities $\text{Int}(S_1 \rightarrow S_0)$ and $\text{Int}(T_1 \rightarrow T_0)$ can be determined spectroscopically by a spectrophotometer. A graph of the logarithmic intensity ratios $\text{Int}(S_1 \rightarrow S_0)/\text{Int}(T_1 \rightarrow T_0)$ measured at different temperatures versus the reciprocal of the absolute temperature T generally shows a straight line. The measurement is carried out in a temperature range from room temperature (300 K) to 77 K to 4.2 K (the temperature can be adjusted by means of a cryostat). The respective transitions $(S_1 \rightarrow S_0)$ and $(T_1 \rightarrow T_0)$ (band intensities) can be identified since the triplet transition is at lower energy than the singlet transition and increases in intensity with decreasing temperature. The measurements are usually performed in oxygen-free dilute solutions (about $10^{-2}$ molL$^{-1}$) or thin films of the respective compounds or doped films comprising the corresponding compounds.

The slope of the straight line mentioned above is $-\Delta E/k_BT$. With $k_B=1.380\ 10^{-23}\ JK^{-1}=0.695\ cm^{-1}\ K^{-1}$, $\Delta E_{ST}$ can be determined.

ii) $\Delta E_{ST}$ can also be determined by measuring the temperature dependency of the emission decay as known by a person skilled in the art.

iii) An approximate estimation of $\Delta E_{ST}$ can be achieved by recording the fluorescence and phosphorescence spectra at low temperature (for example 77 K or 4.2 K using a cryostat). $\Delta E_{ST}$ then corresponds to an approximation of the energy difference between the high-energy rising edges of the fluorescence or phosphorescence band.

FIG. 1: PL emission spectra of codeposited film (3,3-di (9H-carbazol-9-yl)biphenyl (mCBP) doped with 8.6% by weight of compound

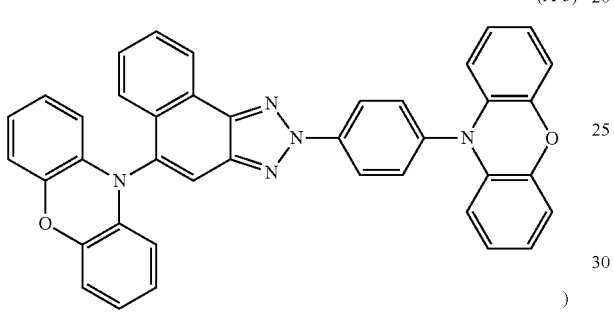
(A-5)

recorded with a streak camera. Fluorescence (dotted line) and TADF (thin line) spectra are recorded at 298 K using a time range of 0 to 30 ns and a time range of >1 μs, respectively. The phosphorescence (thick line) spectrum is measured at 8 K, by using a time range of 20 to 30 ms and omitting the prompt fluorescence.

Figure 2:
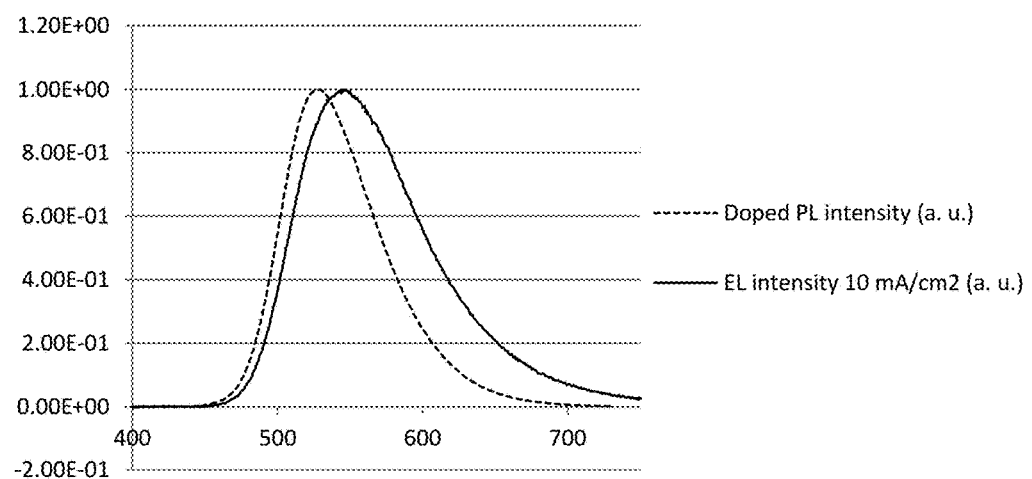

FIG. 2: Photoluminescence (PL, dotted line) and electroluminescence (EL, thin line; at 10 mA/cm²) spectra measured from a codeposited film (mCBP doped with 8.6% by weight of compound (A-5)) and the OLED of Application Example 2, respectively.

The compounds of formula (I) contain preferably one, or two donor groups of formula (Xa), (Xb), (Xc) and/or (Xd).

Compounds of formula (I) are preferred, wherein $R^1$, $R^2$, $R^3$, $R^4$, $R^6$, $R^7$, $R^8$ and $R^9$ are independently of each other H, a $C_1$-$C_{25}$alkyl group, a $C_1$-$C_{25}$alkoxy group, a $C_6$-$C_{10}$aryloxy group, a donor group of formula

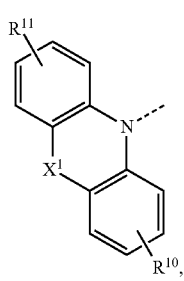
(Xa)

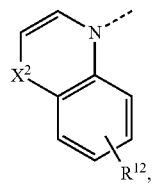
(Xb)

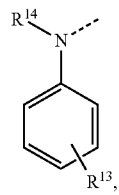
(Xc)

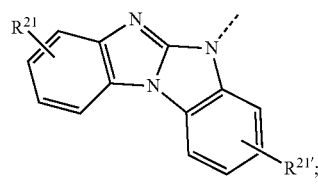
(Xd)

or
$R^1$ and $R^2$ together form a group of formula

and/or
$R^8$ and $R^9$ together form a group of formula

$R^5$ is H, a $C_1$-$C_{25}$alkyl group, a group of formula

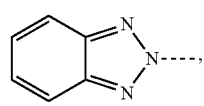

or a donor group of formula (Xa), (Xb), (Xc), or (Xd);
$X^1$ and $X^2$ are independently of each other a single bond, O, S, C(O), N($R^{15}$), or C($R^{16}$)($R^{17}$); and
$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

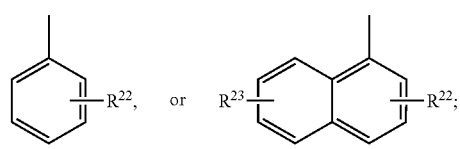

$R^{16}$ and $R^{17}$ are independently of each other H, a $C_1$-$C_{25}$alkyl group;

$R^{22}$ and $R^{23}$ are independently of each other H, a $C_1$-$C_{25}$alkyl group, a $C_1$-$C_{25}$alkoxy group, or a $C_6$-$C_{10}$aryloxy group;

with the proviso that at least one of $R^1$, $R^2$, $R^3$, $R^4$, $R^5$, $R^6$, $R^7$, $R^8$ and $R^9$ is a donor group of formula (Xa), (Xb), (Xc), or (Xd).

Among the compounds of formula (I) compounds of formula

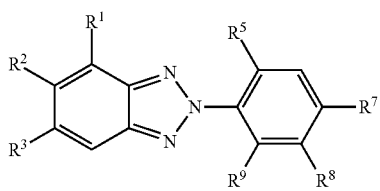
(Ia)

are more preferred, wherein $R^1$ and $R^2$ are independently of each other H, or a $C_1$-$C_{25}$alkyl group, or $R^1$ and $R^2$ together form a group of formula

;

$R^3$, $R^7$ and $R^8$ are independently of each other H, a $C_1$-$C_{25}$alkyl group, or a donor group of formula

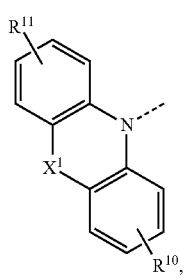
(Xa)

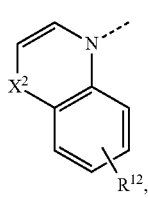
(Xb)

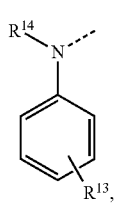
(Xc)

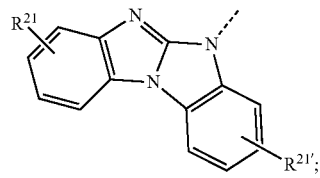
(Xd)

$R^5$ is H, a $C_1$-$C_{25}$alkyl group, a group of formula

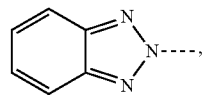
, or a donor group of formula (Xa), (Xb), (Xc), or (Xd);

$R^9$ is H, or $R^8$ and $R^9$ together form a group of formula

;

$X^1$ and $X^2$ are independently of each other a single bond, O, S, N($R^{15}$), or C($R^{16}$)($R^{17}$);

$R^{10}$, $R^{11}$, $R^{12}$, $R^{13}$, $R^{21}$ and $R^{21'}$ are independently of each other H, or a $C_1$-$C_{25}$alkyl group;

$R^{14}$ and $R^{15}$ are independently of each other a group of formula

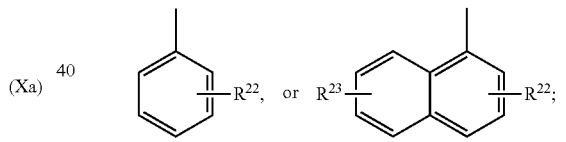
;

$R^{16}$ and $R^{17}$ are independently of each other H, a $C_1$-$C_{25}$alkyl group;

$R^{22}$ and $R^{23}$ are independently of each other H, or a $C_1$-$C_{25}$alkyl group;

with the proviso that at least one of $R^3$, $R^5$ and $R^7$ is a donor group of formula (Xa), (Xb), (Xc), or (Xd).

Among the compounds of formula (Ia) compounds of formula

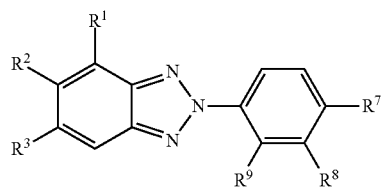
(Ia')

are more preferred, wherein $R^1$ and $R^2$ are independently of each other H, or a $C_1$-$C_{25}$alkyl group, or $R^1$ and $R^2$ together form a group of formula

;

$R^3$ is H, a $C_1$-$C_{25}$alkyl group, or a donor group of formula

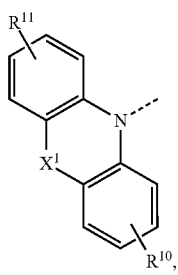

(Xa)

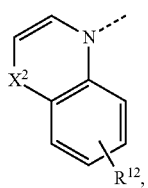

(Xb)

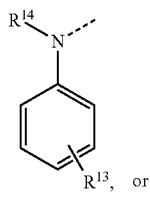

(Xc)

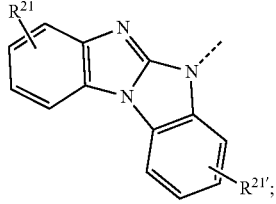

(Xd)

;

$R^7$ is H, a $C_1$-$C_{25}$alkyl group, or a donor group of formula (Xa), (Xb), (Xc), or (Xd);
$R^8$ and $R^9$ are H, or
$R^8$ and $R^9$ together form a group of formula

;

$X^1$ and $X^2$ are independently of each other a single bond, O, S, $N(R^{15})$, or $C(R^{16})(R^{17})$;
$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

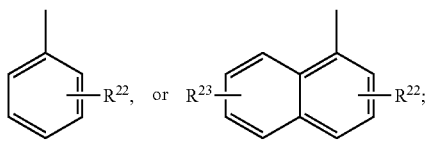

;

$R^{16}$ and $R^{17}$ are independently of each other H, a $C_1$-$C_{25}$alkyl group;

$R^{22}$ and $R^{23}$ are independently of each other H, or a $C_1$-$C_{25}$alkyl group;
with the proviso that at least one of $R^3$ and $R^7$ is a donor group of formula (Xa), (Xb), (Xc), or (Xd).

In addition, among the compounds of formula (Ia) compounds of formula

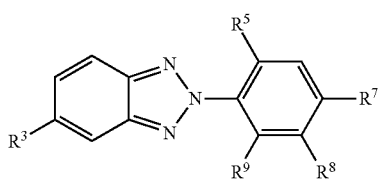

(Ia'')

are more preferred, wherein
$R^5$, $R^8$ and $R^9$ are H;
$R^3$ is H and $R^7$ is a donor group of formula

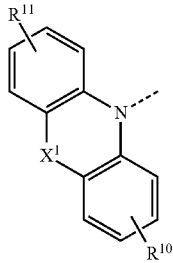

(Xa)

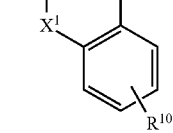

(Xb)

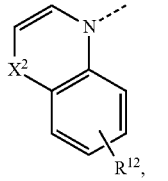

(Xc)

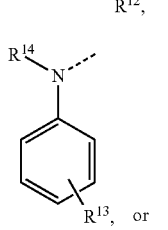

, or

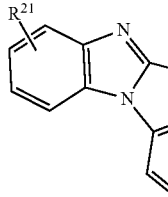

(Xd)

;

or
$R^3$ is a donor group of formula (Xa), (Xb), (Xc), or (Xd) and $R^7$ is H; or
$R^3$ and $R^7$ are a donor group of formula (Xa), (Xb), (Xc), or (Xd); or
a compound of formula (Ia''), wherein
$R^5$ is H;

$R^8$ and $R^9$ together form a group of formula

$R^3$ is H and $R^7$ is a donor group of formula (Xa), (Xb), (Xc), or (Xd); or
$R^3$ is a donor group of formula (Xa), (Xb), (Xc), or (Xd) and $R^7$ is H; or
$R^3$ and $R^7$ are a donor group of formula (Xa), (Xb), (Xc), or (Xd); or
a compound of formula (Ia″), wherein
$R^3$, $R^7$, $R^8$ and $R^9$ are H;
$R^5$ is a donor group of formula (Xa), (Xb), (Xc), or (Xd); or
a compound of formula (Ia‴), wherein
$R^5$, $R^8$ and $R^9$ are H;
$R^3$ is H and $R^7$ is a donor group of formula (Xa), (Xb), (Xc), or (Xd); or
$R^3$ is a donor group of formula (Xa), (Xb), (Xc), or (Xd) and $R^7$ is H; or
$R^3$ and $R^7$ are a donor group of formula (Xa), (Xb), (Xc), or (Xd); or

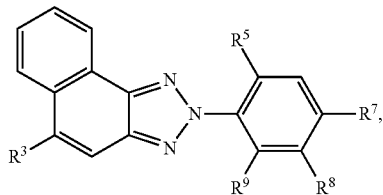

(Ia‴)

wherein
$R^5$, $R^8$ and $R^9$ are H;
$R^3$ is H and $R^7$ is a donor group of formula (Xa), (Xb), (Xc), or (Xd); or
$R^3$ is a donor group of formula (Xa), (Xb), (Xc), or (Xd) and W is H; or
$R^3$ and $R^7$ are a donor group of formula (Xa), (Xb), (Xc), or (Xd); or
a compound of formula (Ia‴), wherein
$R^5$ is H;
$R^8$ and $R^9$ together form a group of formula

$R^3$ is H and $R^7$ is a donor group of formula (Xa), (Xb), (Xc), or (Xd); or
$R^3$ is a donor group of formula (Xa), (Xb), (Xc), or (Xd) and $R^7$ is H; or
$R^3$ and $R^7$ are a donor group of formula (Xa), (Xb), (Xc), or (Xd); or
a compound of formula (Ia‴), wherein
$R^3$, $R^7$, $R^8$ and $R^9$ are H;
$R^5$ is a donor group of formula (Xa), (Xb), (Xc), or (Xd);
$X^1$ and $X^2$ are independently of each other a single bond, O, S, $N(R^{15})$, or $C(R^{16})(R^{17})$;

$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

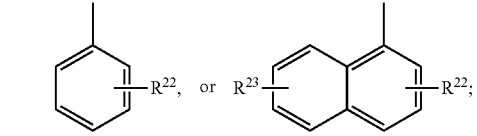

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group. In said embodiment compounds of formula (Ia″) are more preferred, wherein $R^5$, $R^8$ and $R^9$ are H; $R^3$ is H and $R^7$ is a donor group of formula

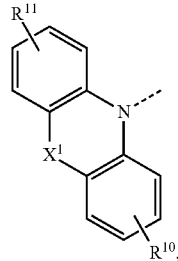

(Xa)

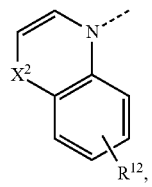

(Xb)

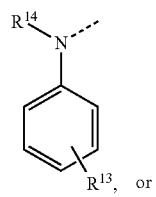

(Xc)

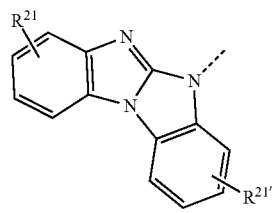

(Xd)

or
$R^3$ is a donor group of formula (Xa), (Xb), (Xc), or (Xd) and W is H; or
$R^3$ and $R^7$ are a donor group of formula (Xa), (Xb), (Xc), or (Xd).
In said embodiment compounds of formula (Iam) are more preferred, wherein
$R^5$, $R^8$ and $R^9$ are H;
$R^3$ is H and $R^7$ is a donor group of formula (Xa), (Xb), (Xc), or (Xd); or $R^3$ is a donor group of formula (Xa), (Xb), (Xc), or (Xd) and $R^7$ is H; or
$R^3$ and $R^7$ are a donor group of formula (Xa), (Xb), (Xc), or (Xd) and
$X^1$ and $X^2$ are independently of each other a single bond, O, S, C(O), N($R^{15}$), or C($R^{16}$)($R^{17}$);
$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

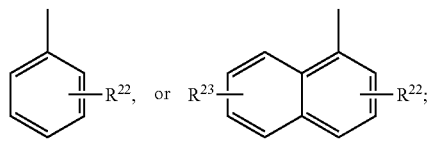

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group.

In an additional preferred embodiment the present invention is directed to organic light-emitting elements, comprising compounds of formula

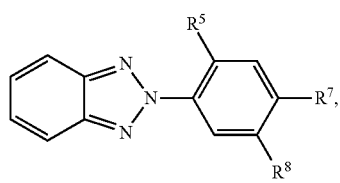

(Ib)

wherein
$R^5$ is a group of formula

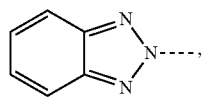

$R^7$ and $R^8$ are a donor group of formula

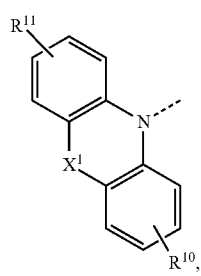

(Xa)

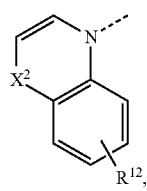

(Xb)

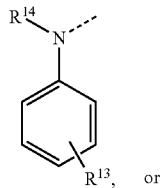

(Xc)

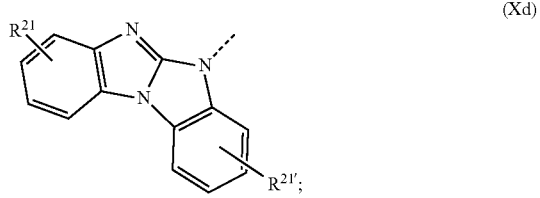

(Xd)

or
compounds of formula (Ib), wherein
$R^5$ is a donor group of formula (Xa), (Xb), (Xc), or (Xd), and
$R^7$ and $R^8$ are independently of each other H, or a $C_1$-$C_{25}$alkyl group; and
$X^1$ and $X^2$ are independently of each other a single bond, O, S, C(O), N($R^{15}$), or C($R^{16}$)($R^{17}$);
$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

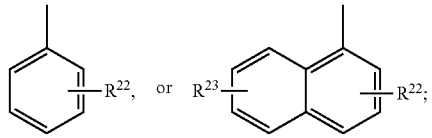

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group.

In an additional preferred embodiment the present invention is directed to organic light-emitting elements, comprising compounds of formula

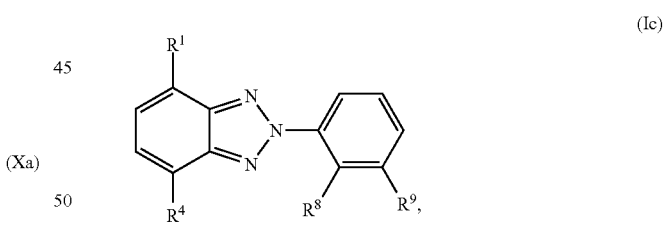

(Ic)

wherein
$R^1$ and $R^4$ are a donor group of formula

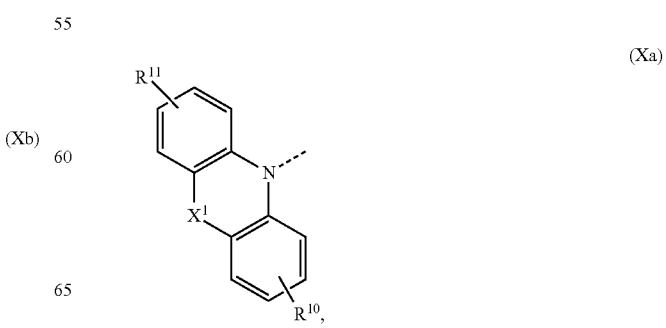

(Xa)

-continued

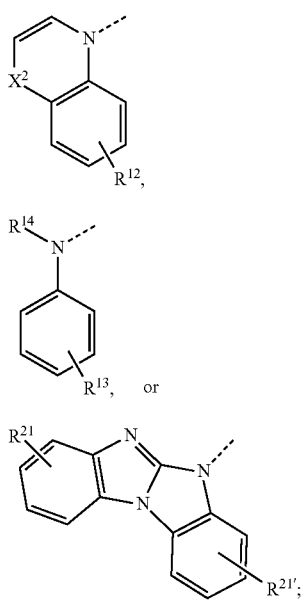

and
$X^1$ and $X^2$ are independently of each other a single bond, O, S, C(O), N($R^{15}$), or C($R^{16}$)($R^{17}$);
$R^8$ and $R^9$ are H, or
$R^8$ and $R^9$ together form a group of formula

$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

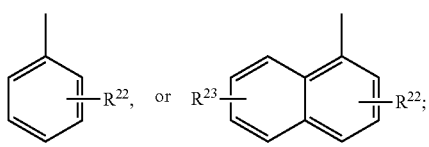

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group.

Examples of donor groups of formula (Xa) are a group of formula

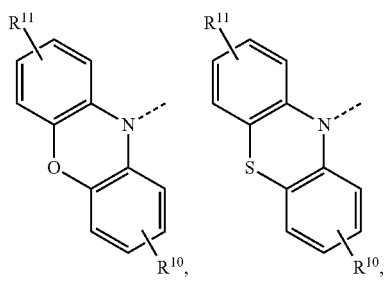

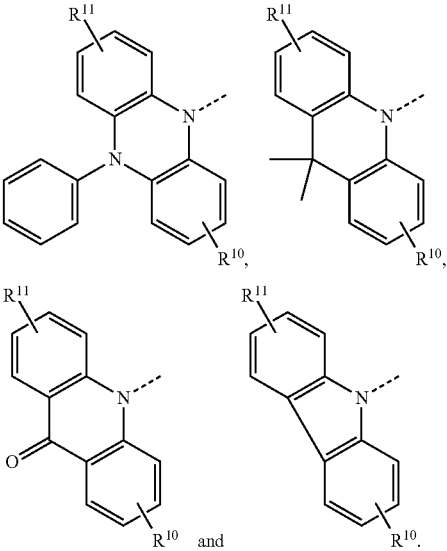

Groups of formula

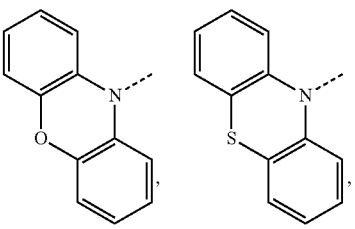

are preferred. Groups of formula

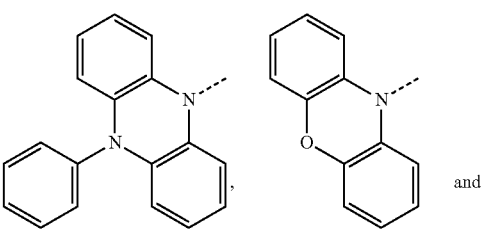

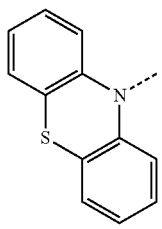

are most preferred.

Examples of the donor group of formula (Xb) are groups of formula

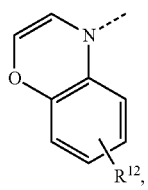 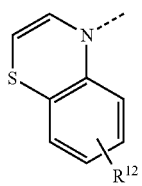 and 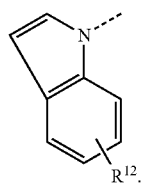

Groups of formula

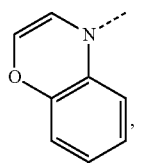 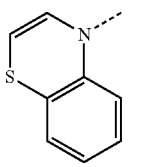 and 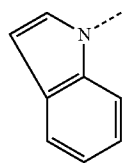

are preferred. A group of formula

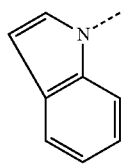

is most preferred.

Examples of the donor group of formula (Xc) are a group of formula

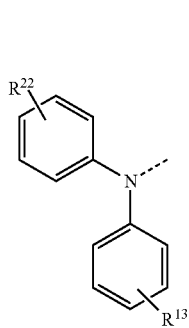 and 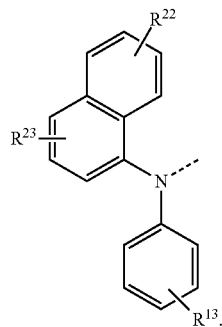

Groups of formula

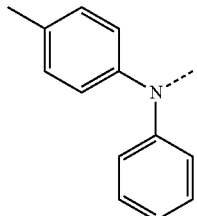 and 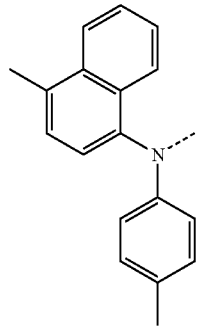

are most preferred.

Among the donor groups of formula (Xd) a group of formula

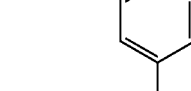

is preferred. The donor group is preferably a donor group of formula (Xa), wherein $X^1$ is a single bond, O, S, C(CH$_3$)(CH$_3$), C(=O),

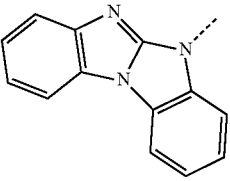

or a donor group of formula (Xb), wherein $X^2$ is a single bond and $R^{12}$ is H; or a donor group of formula (Xc), wherein $R^{13}$ is a group of formula

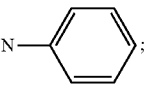

and $R^{14}$ is a group of formula

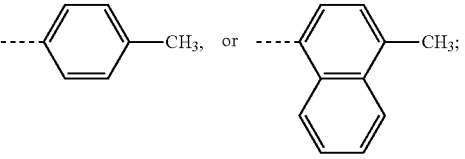

or a donor group of formula (Xd), wherein $R^{21}$ and $R^{21'}$ are H.

Among the donor groups of formula (Xa), (Xb), (Xc) and (Xd) donor groups of formula (Xa) and (Xc) are preferred. Donor groups of formula (Xa) are most preferred.

Among the donor groups of formula (Xa) groups of formula
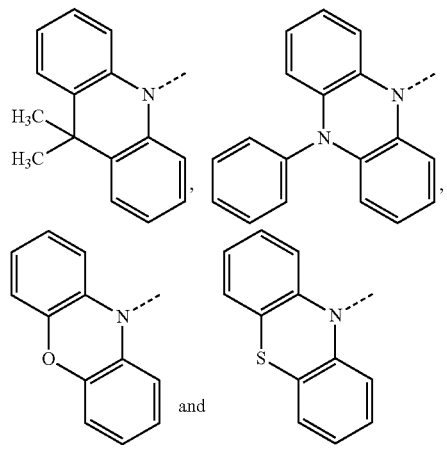
and
are most preferred.
Examples of compounds of formula (Ia) are shown below:
(A-1)
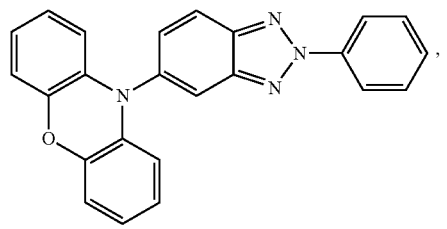
(A-2)
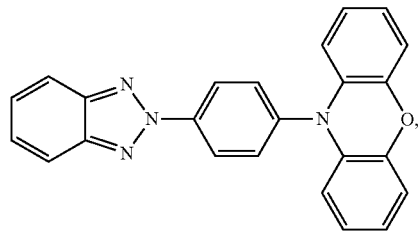
(A-3)
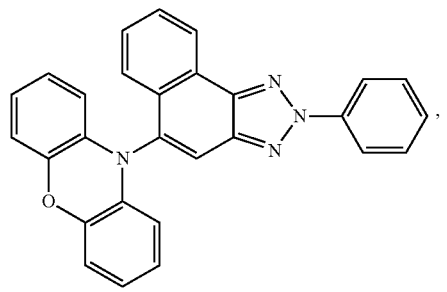
(A-4)
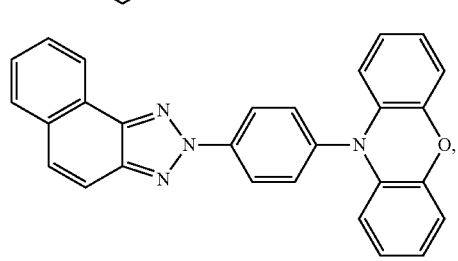
(A-5)
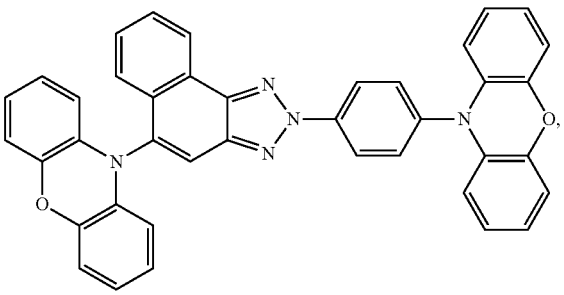
(A-6)
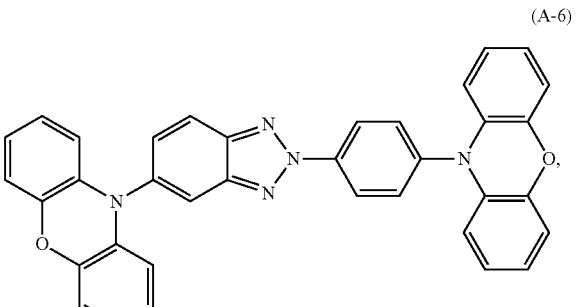
(A-7)
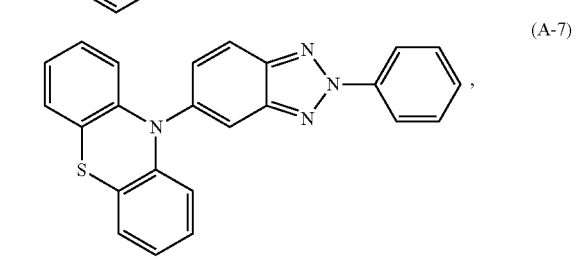
(A-8)
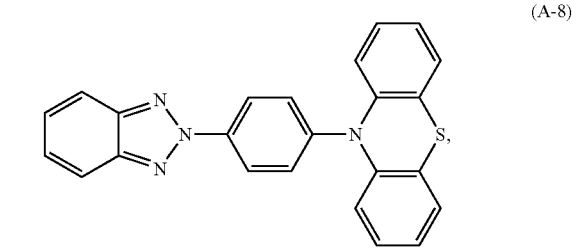
(A-9)
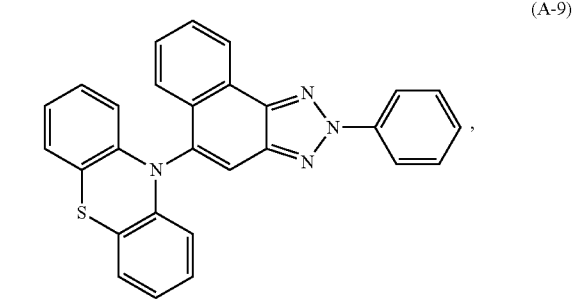
(A-10)
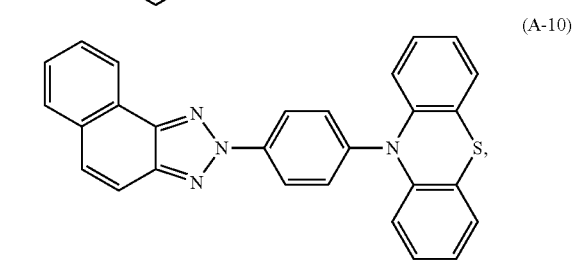

(A-11)
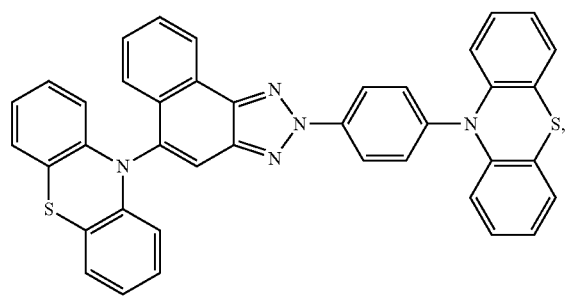
(A-17)
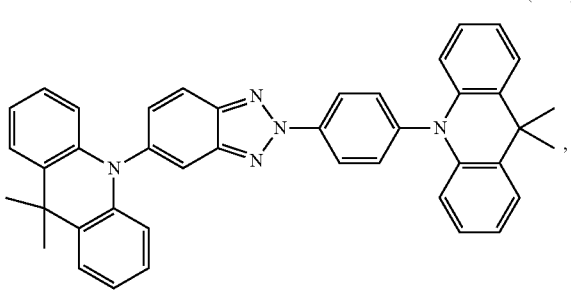
(A-12)
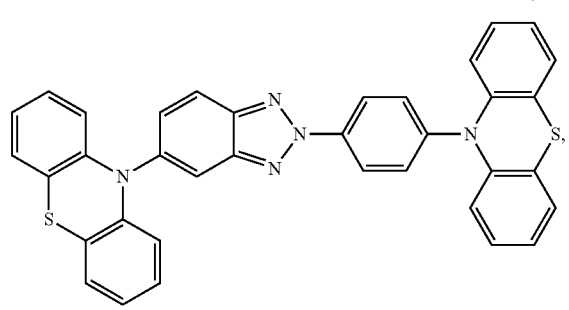
(A-18)
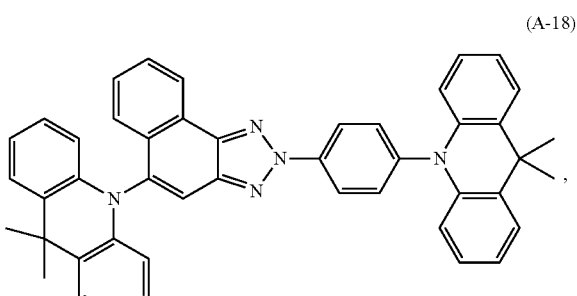
(A-13)
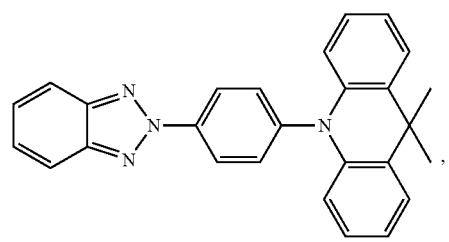
(A-19)
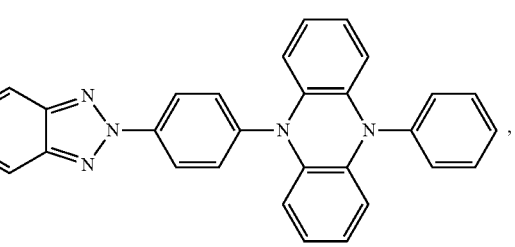
(A-14)
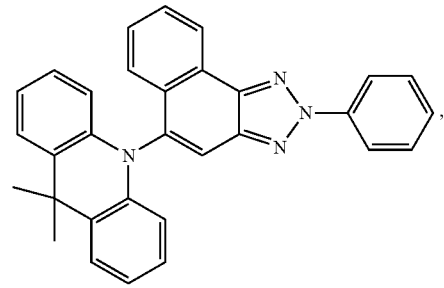
(A-20)
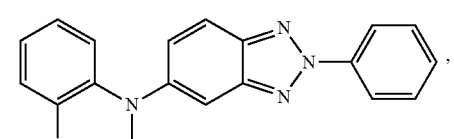
(A-15)
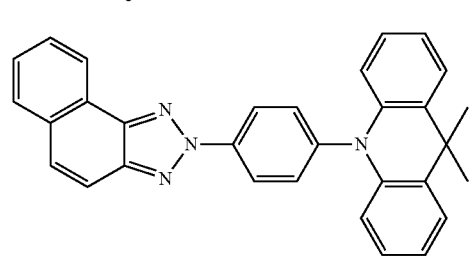
(A-21)
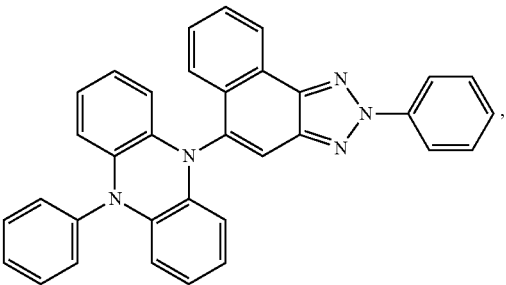
(A-16)

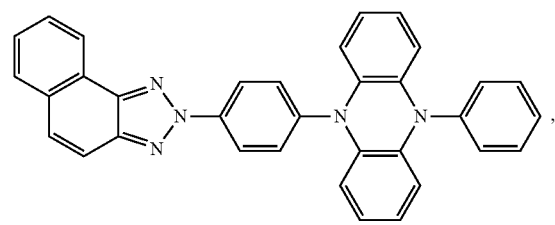
(A-22)
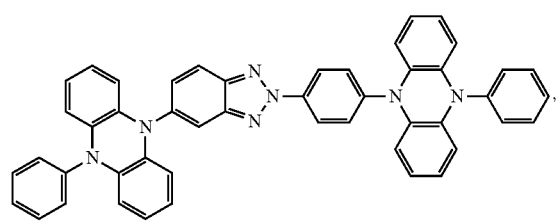
(A-23)
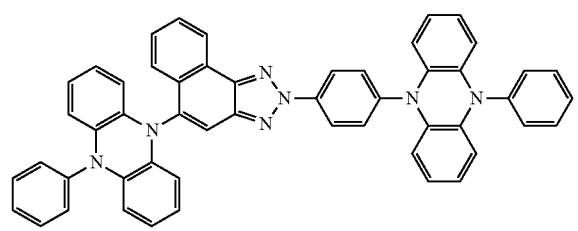
(A-24)
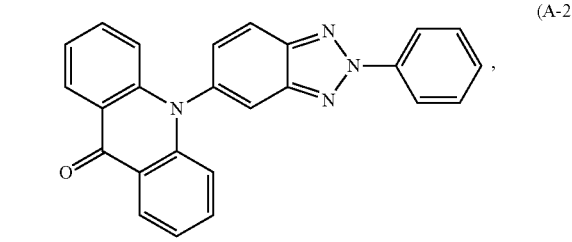
(A-25)
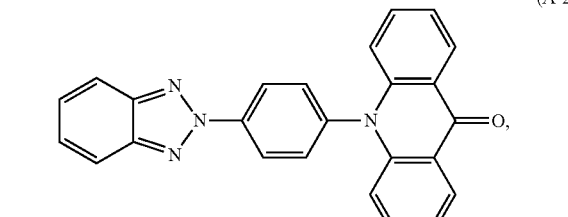
(A-26)
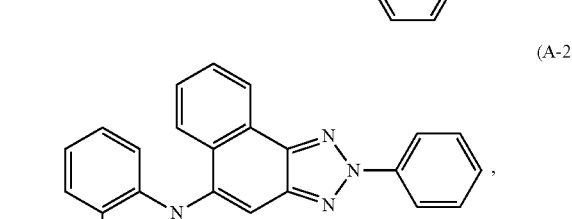
(A-27)
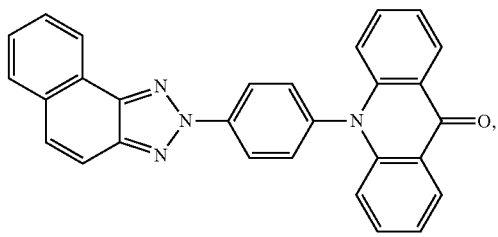
(A-28)
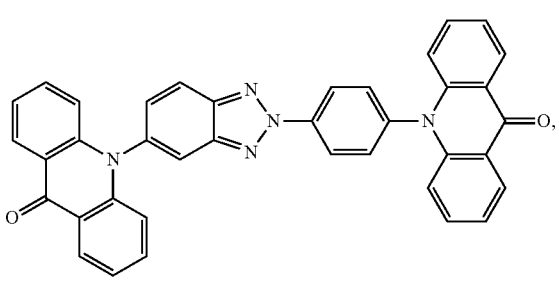
(A-29)
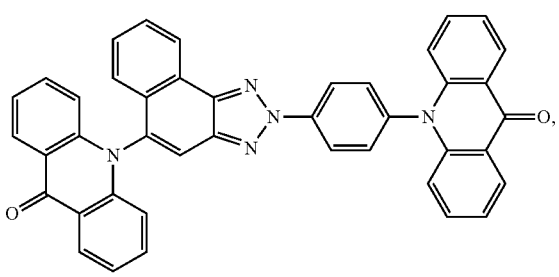
(A-30)
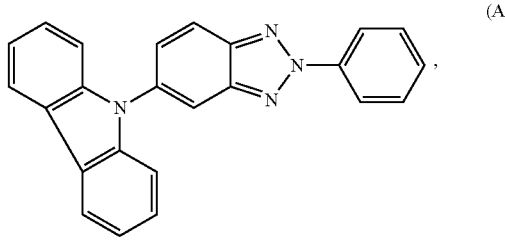
(A-31)
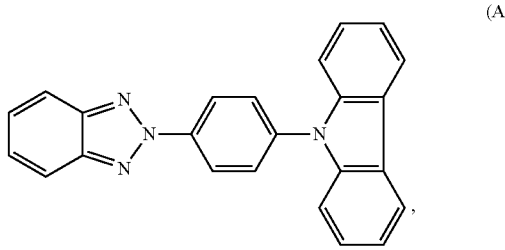
(A-32)
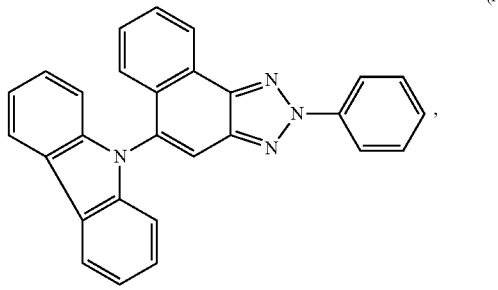
(A-33)

(A-34)
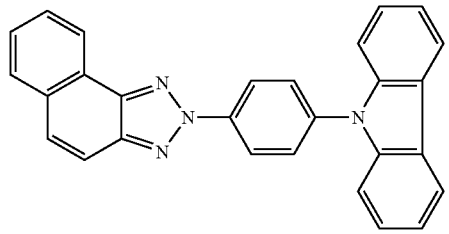
(A-35)
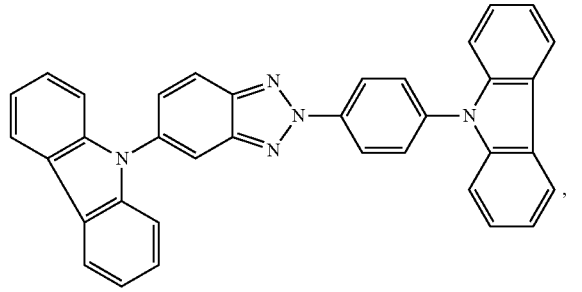
(A-36)
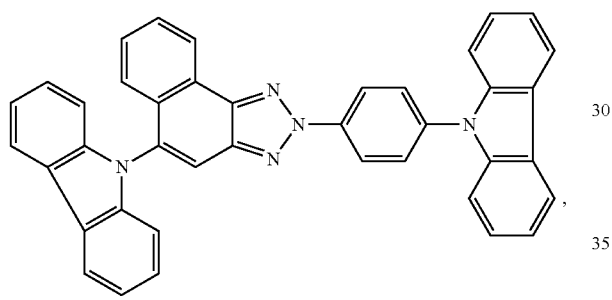
(A-37)
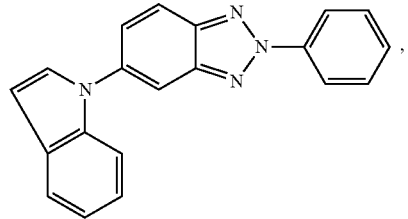
(A-38)
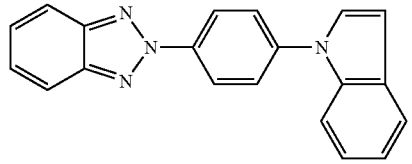
(A-39)
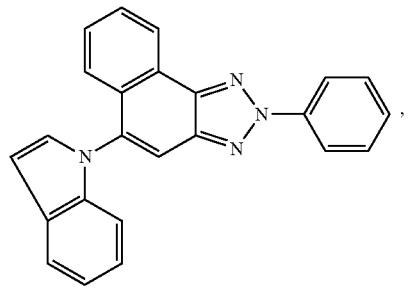
(A-40)
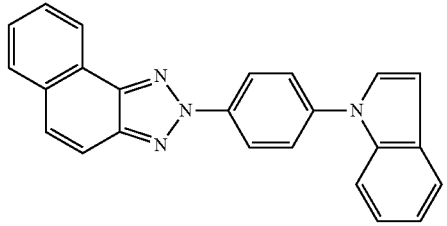
(A-41)
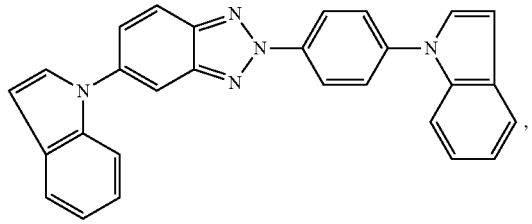
(A-42)
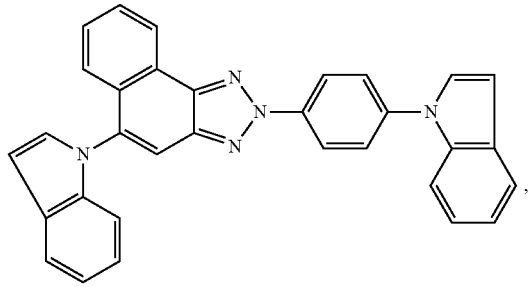
(A-43)
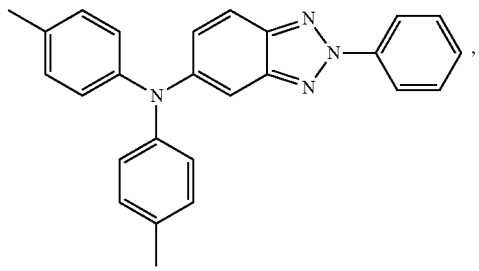
(A-44)
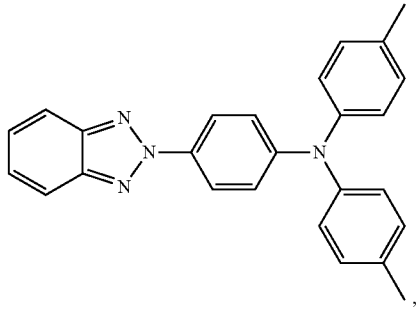

-continued
(A-45)
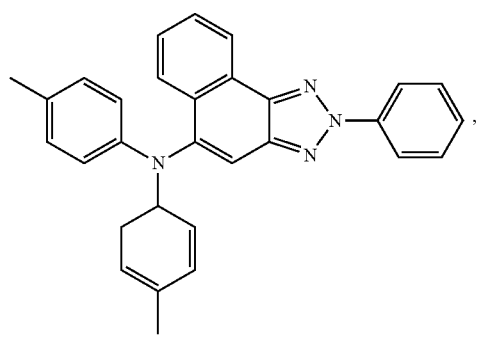
(A-46)
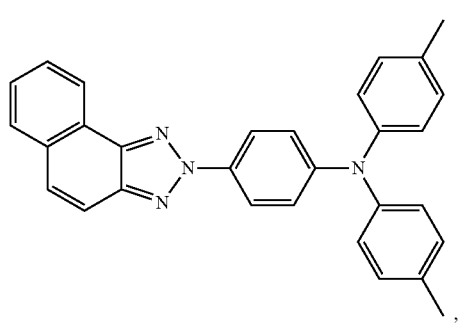
(A-47)
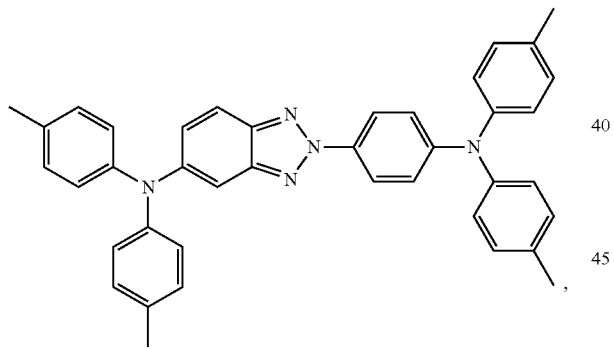
(A-48)
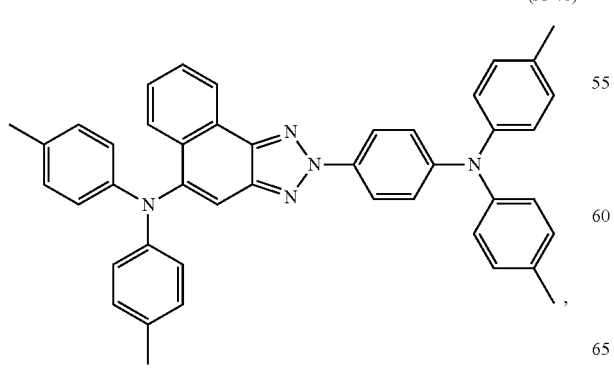
-continued
(A-49)
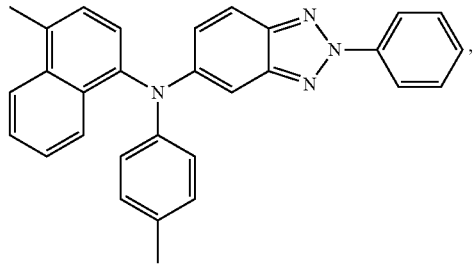
(A-50)
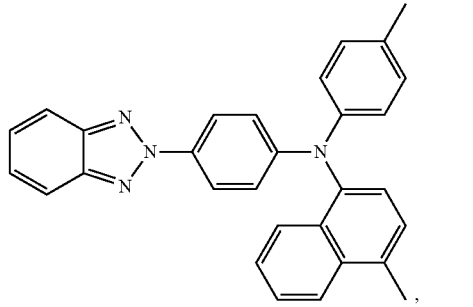
(A-51)
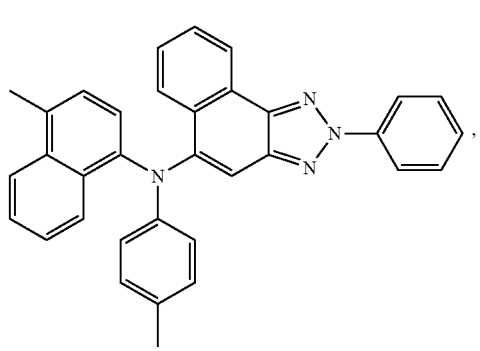
(A-52)
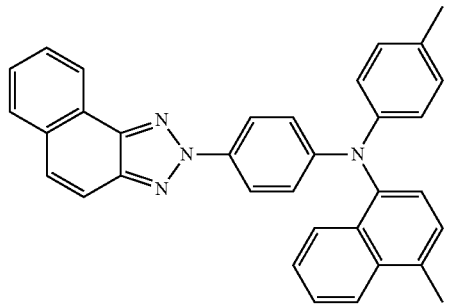
(A-53)
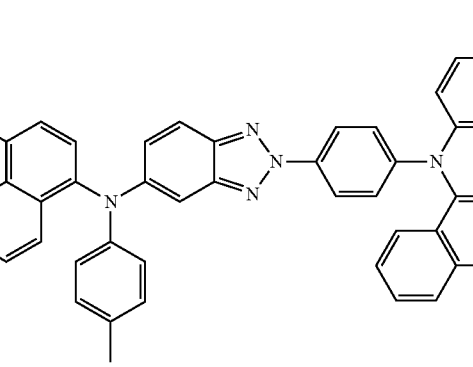

(A-54)
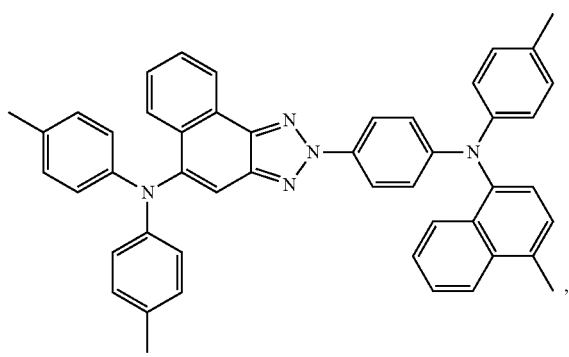
(A-55)
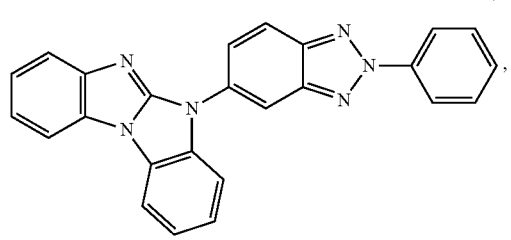
(A-56)
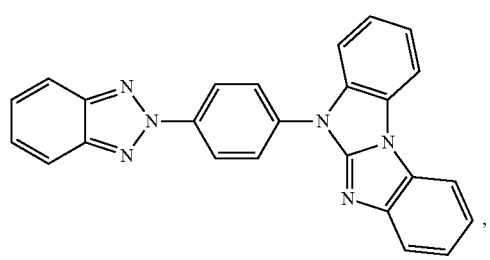
(A-57)
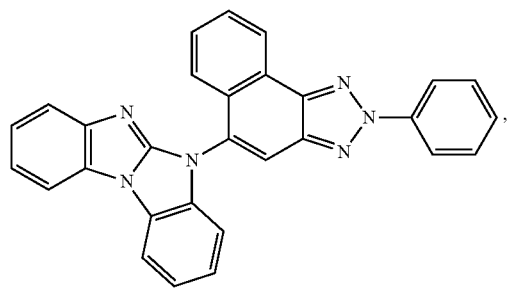
(A-58)
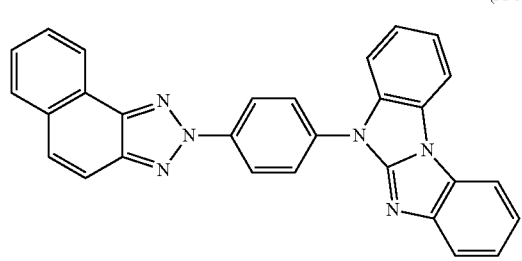
(A-59)
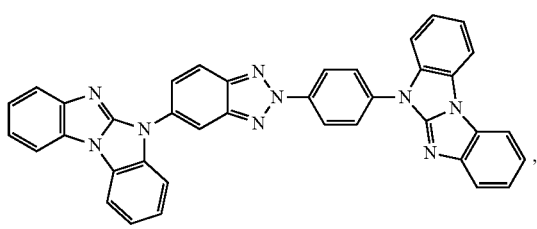
(A-60)
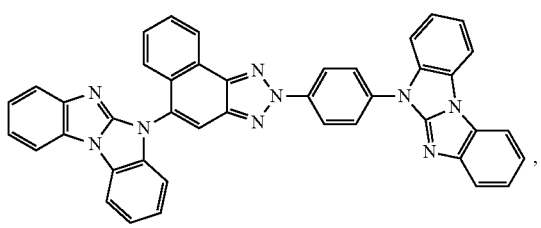
(A-61)
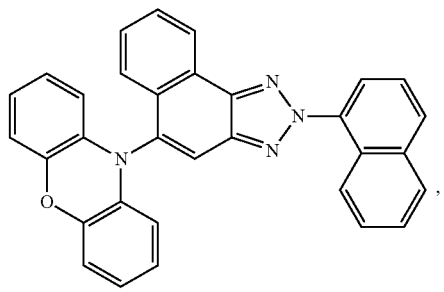
(A-62)
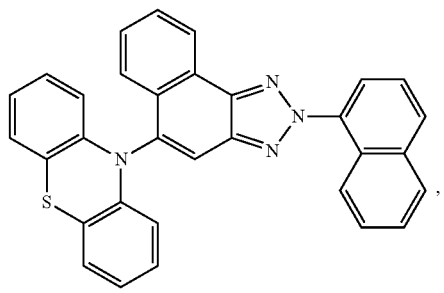
(A-63)
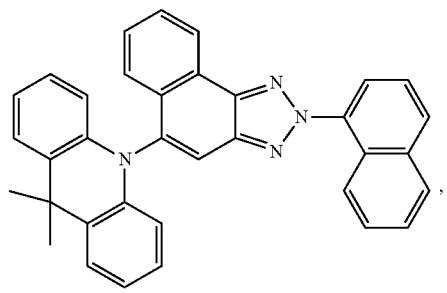

(A-64)
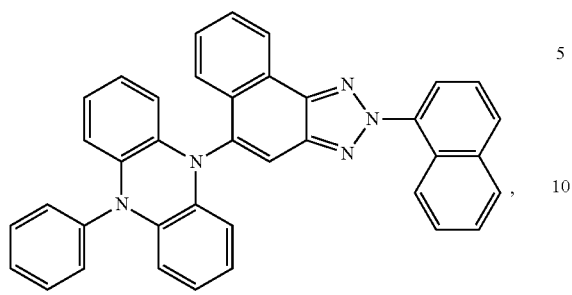
(A-65)
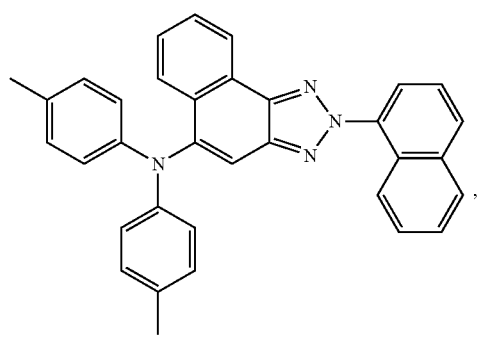
(A-66)
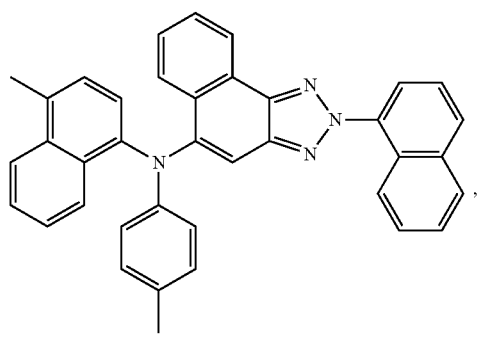
(A-67)
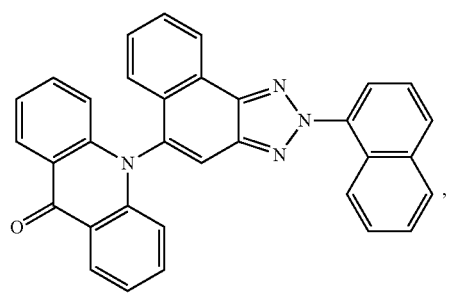
(A-68)
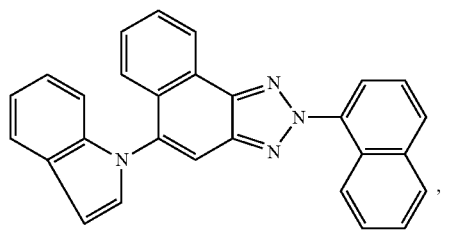
(A-69)
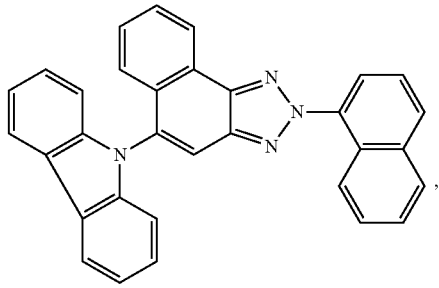
(A-70)
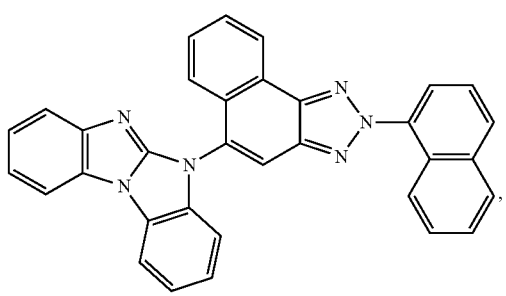
(A-71)
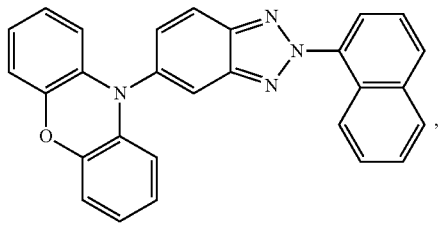
(A-72)
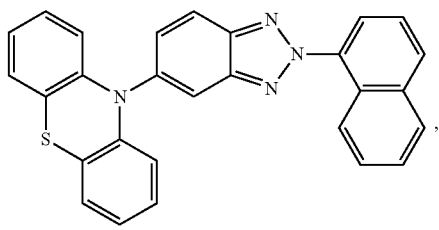
(A-73)
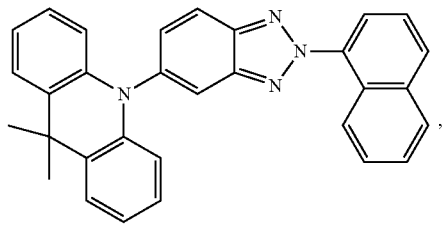
(A-74)
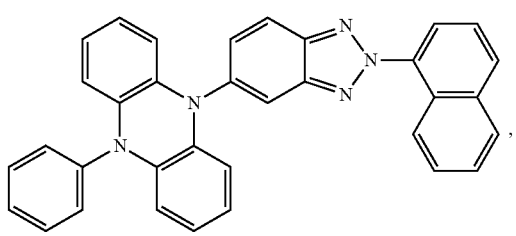

(A-75)
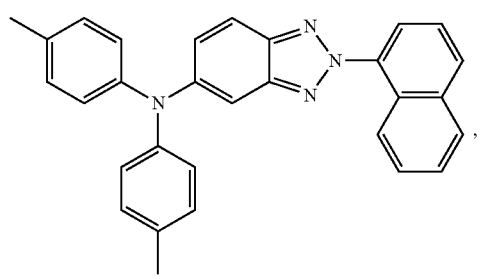
(A-76)
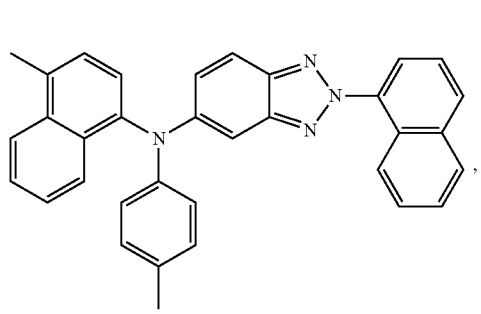
(A-77)
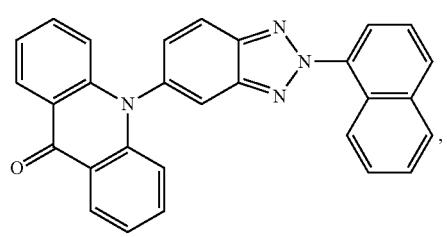
(A-78)
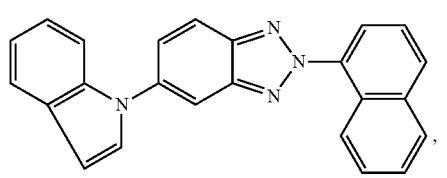
(A-79)
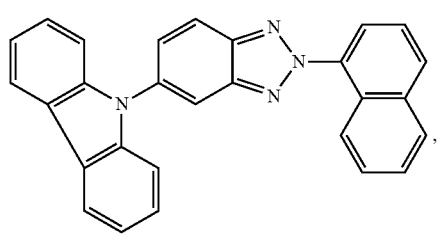
(A-80)
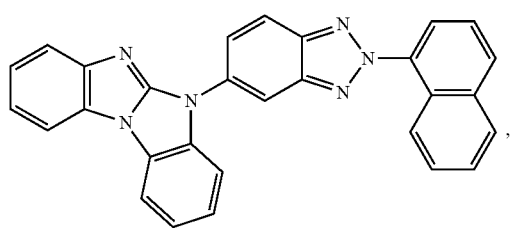
(A-81)
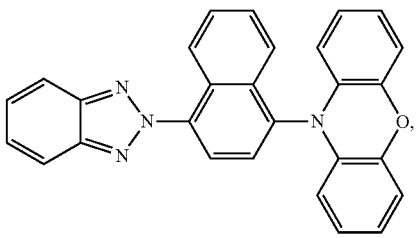
(A-82)
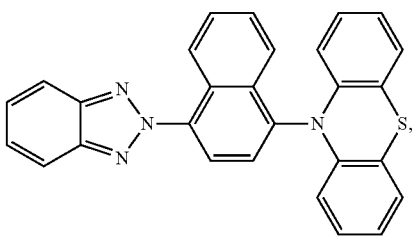
(A-83)
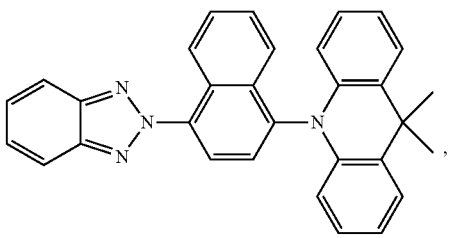
(A-84)
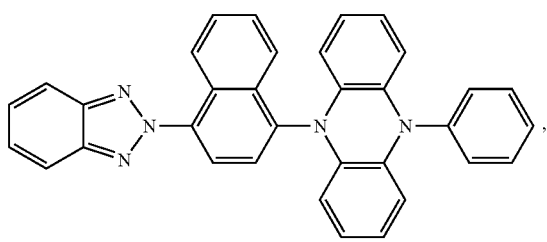
(A-85)
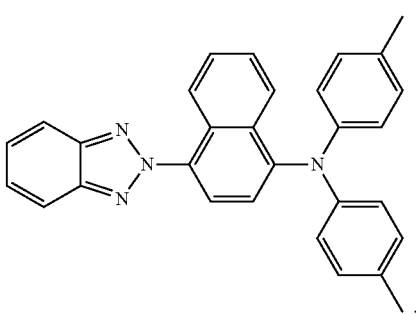
(A-86)
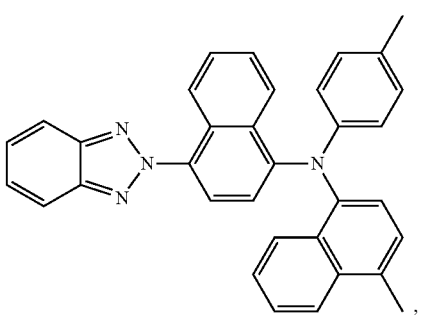

(A-87)
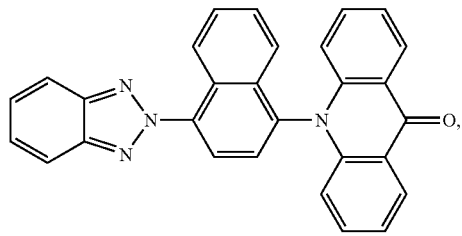
(A-88)
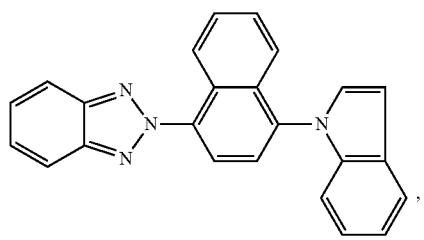
(A-89)
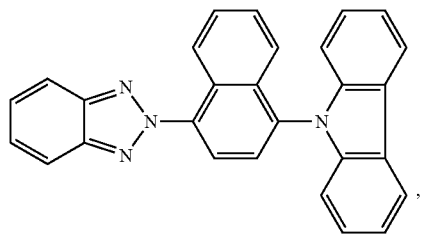
(A-90)
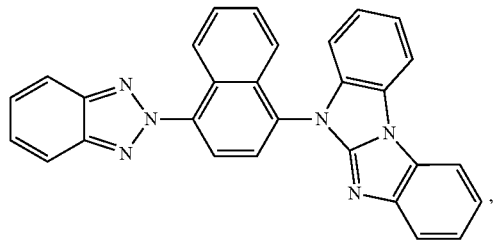
(A-91)
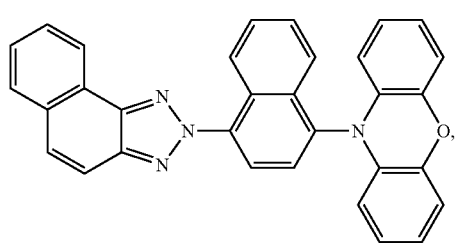
(A-92)
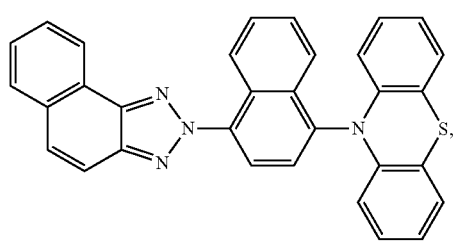
(A-93)
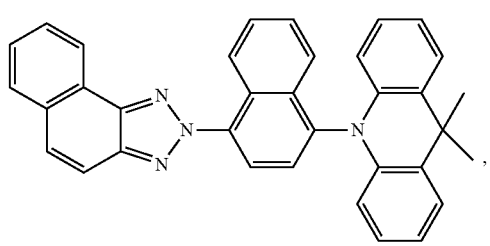
(A-94)
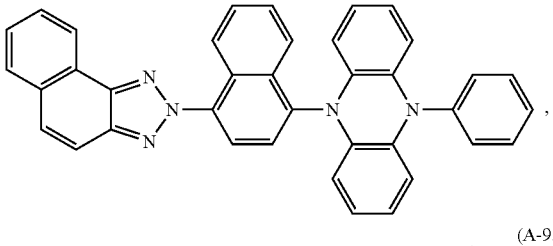
(A-95)
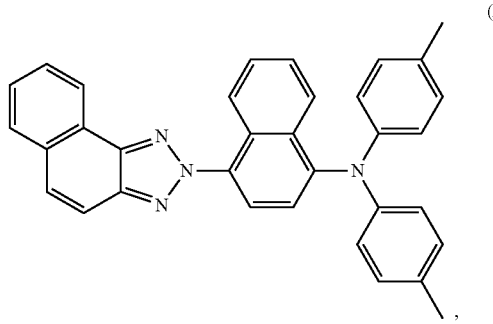
(A-96)
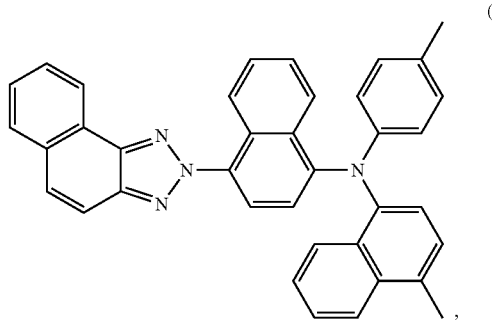
(A-97)
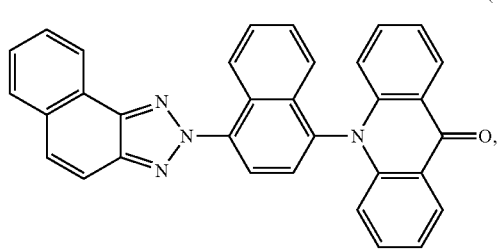
(A-98)
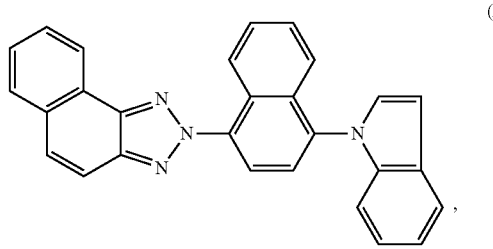

(A-99)
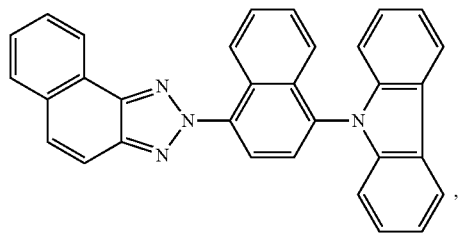
(A-100)
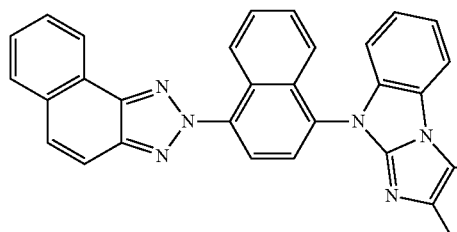
(A-101)
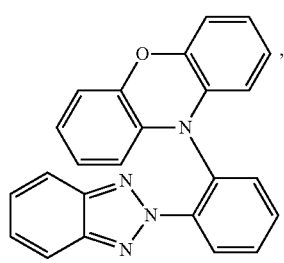
(A-102)
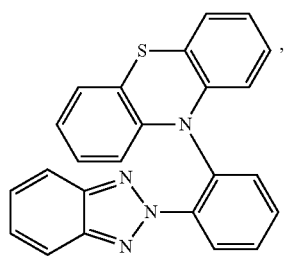
(A-103)
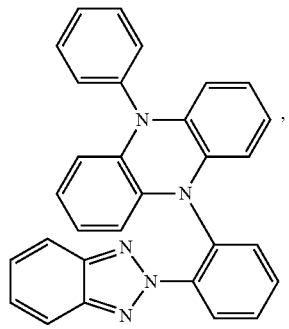
(A-104)
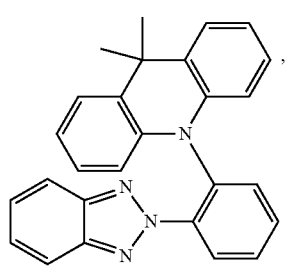
(A-105)
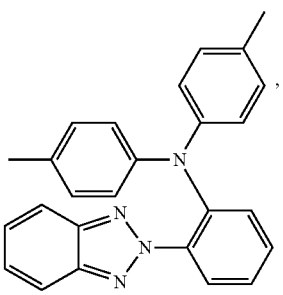
(A-106)
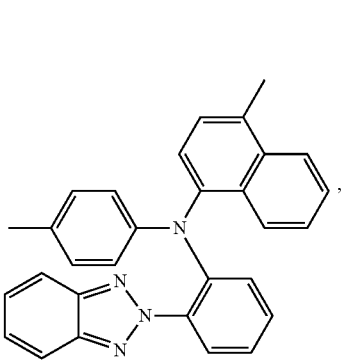
(A-107)
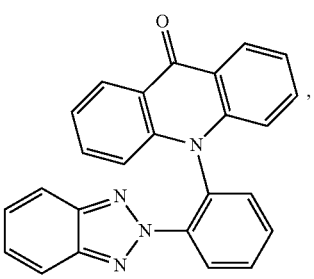
(A-108)
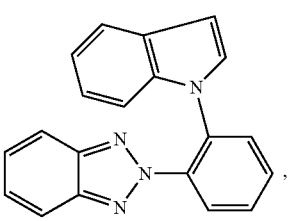
(A-109)
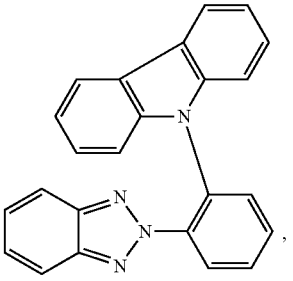

(A-110) 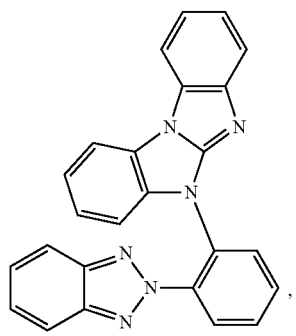
(A-111) 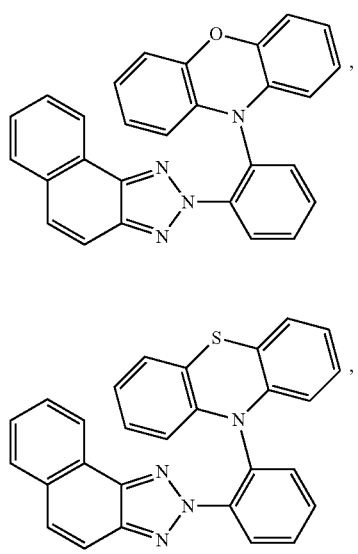
(A-112) 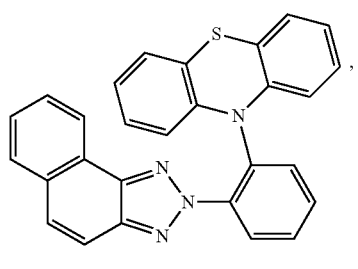
(A-113) 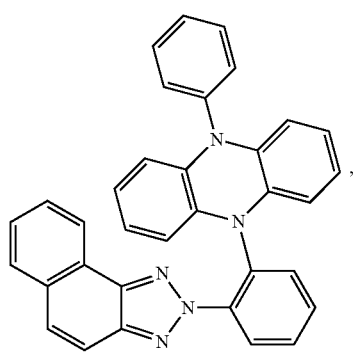
(A-114) 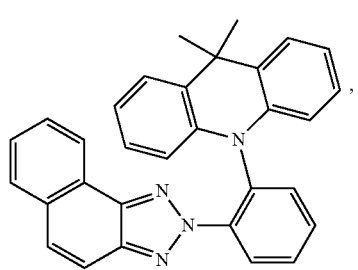
(A-115) 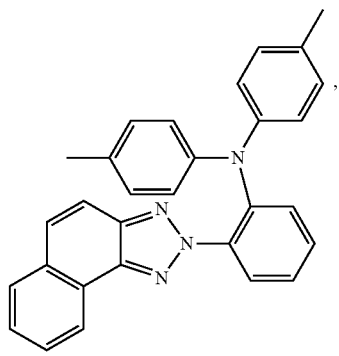
(A-116) 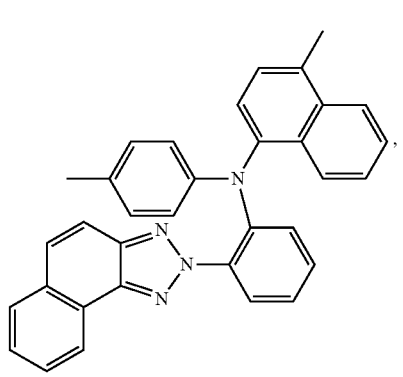
(A-117) 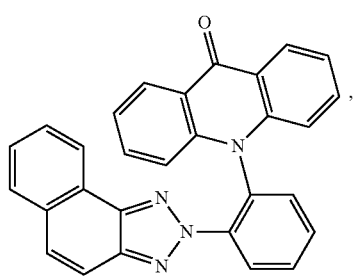
(A-118) 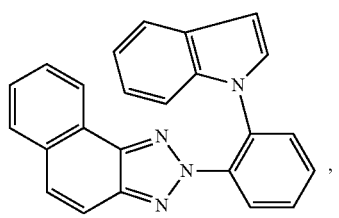
(A-119) and 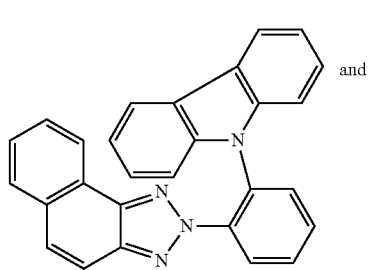

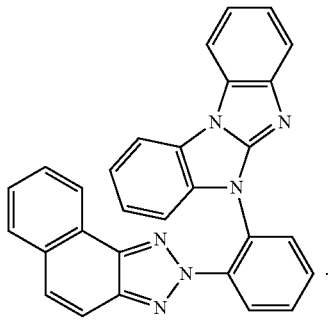
(A-120)
Among compounds of formula (Ia) those are preferred which are substituted by donor groups of formula (Xa), especially groups of formula
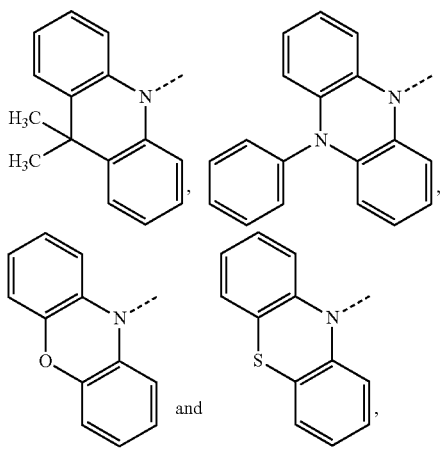
such as, for example, compounds (A-1), (A-2), (A-3), (A-4), (A-5), (A-6), (A-7), (A-8), (A-9), (A-10), (A-11), (A-12), (A-13), (A-14), (A-15), (A-16), (A-17), (A-18), (A-19), (A-20), (A-21), (A-22), (A-61), (A-62), (A-63), (A-64), (A-71), (A-72), (A-73), (A-74), (A-81), (A-82), (A-83), (A-84), (A-91), (A-92), (A-93), (A-94), (A-101), (A-102), (A-103), (A-104), (A-111), (A-112), (A-113) and (A-114).
Examples of compounds of formula (Ib) are shown below:
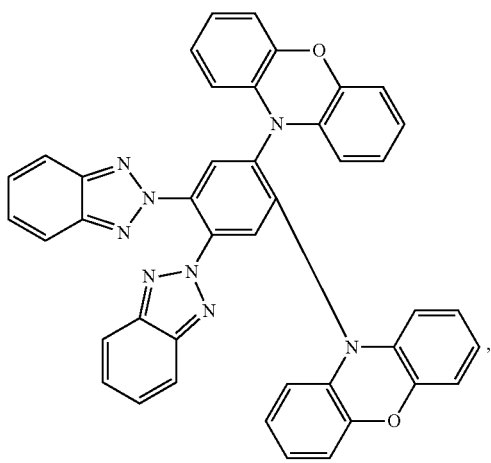
(B-1)
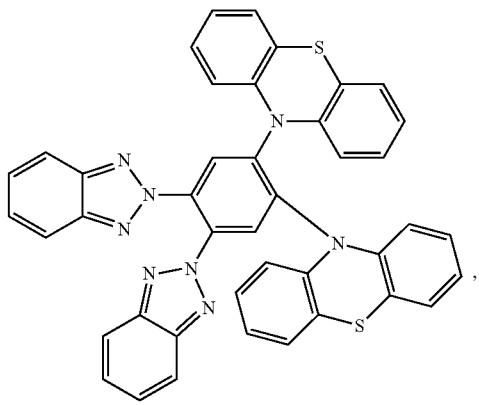
(B-2)
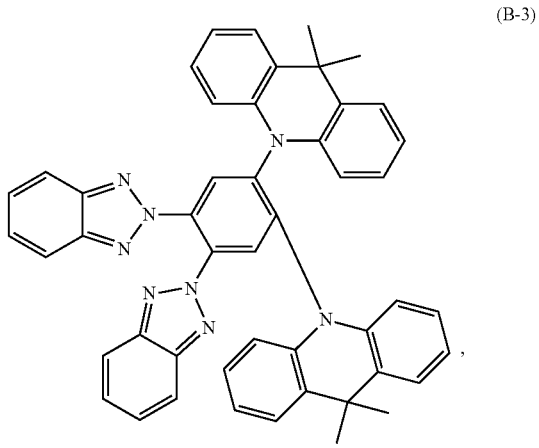
(B-3)
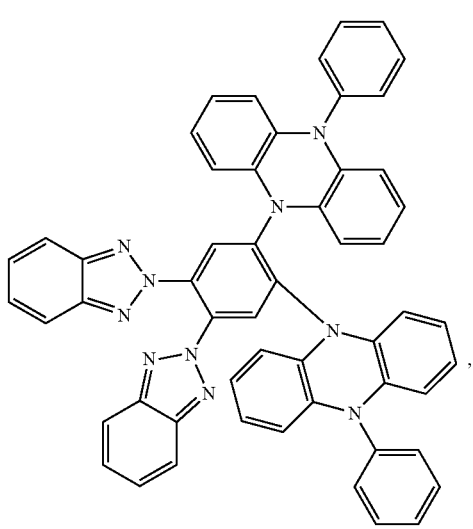
(B-4)

(B-5)
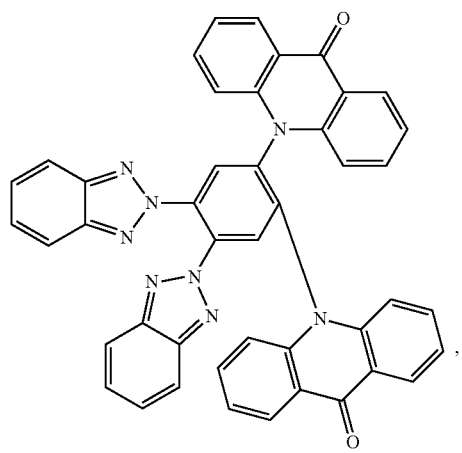
(B-6)
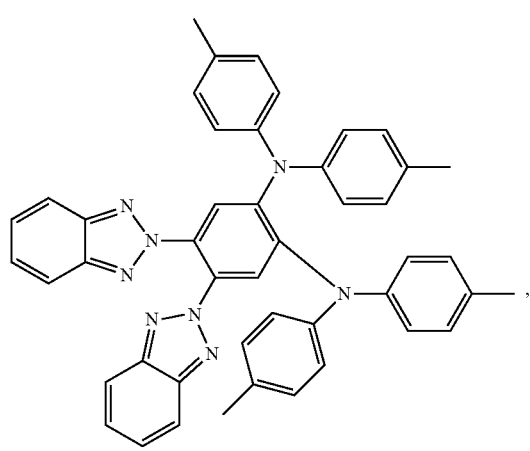
(B-7)
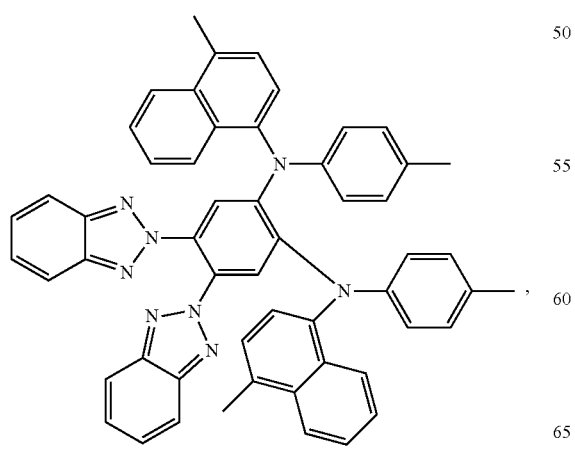
(B-8)
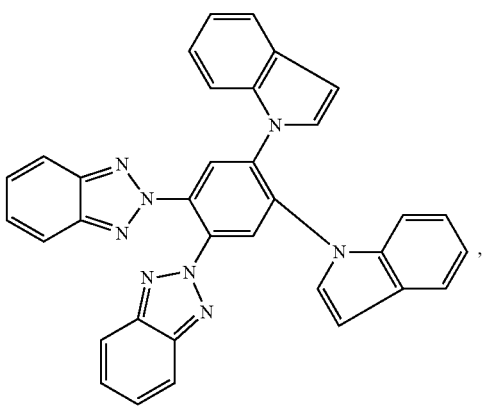
(B-9)
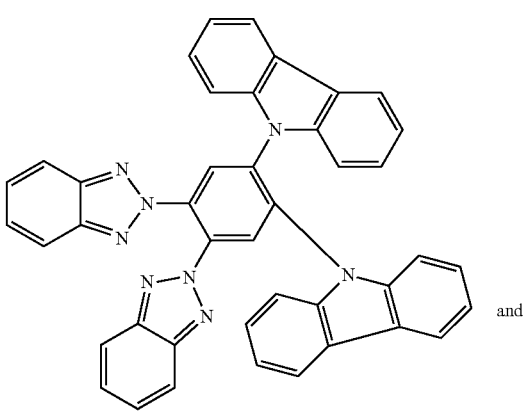
and
(B-10)
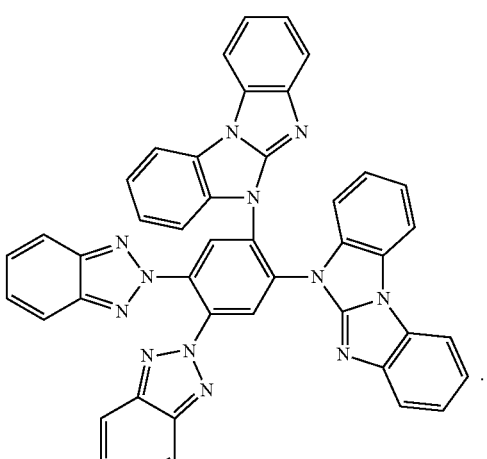
Among compounds of formula (Ib) those are preferred which are substituted by donor groups of formula (Xa), especially groups of formula

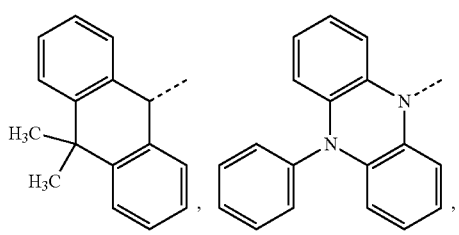
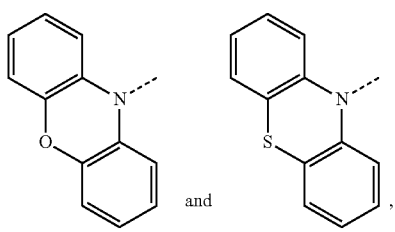
such as, for example, compounds (B-1), (B-2), (B-3) and (B-4).
Examples of compounds of formula (Ic) are shown below:
(C-1)
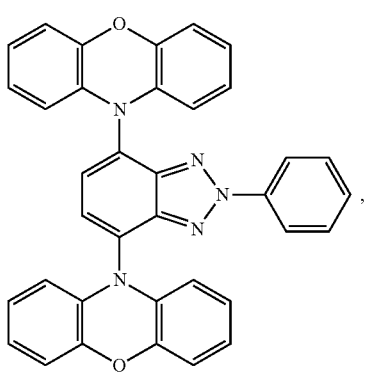
(C-2)
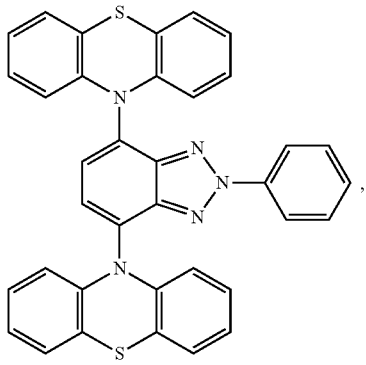
(C-3)
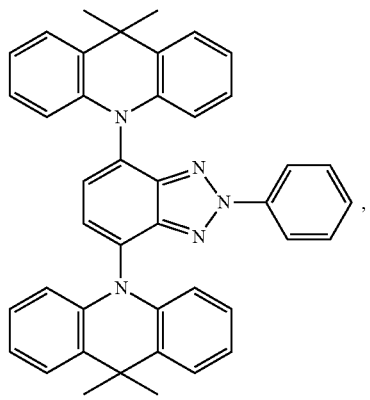
(C-4)
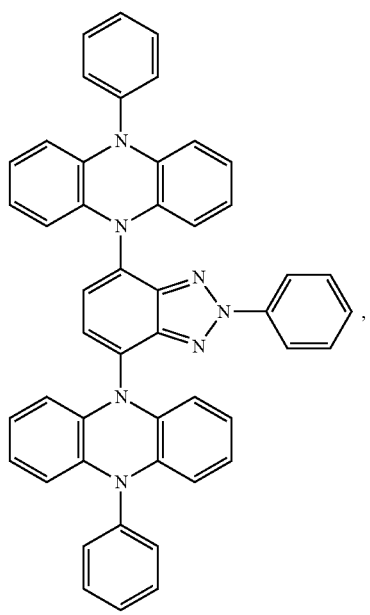
(C-5)
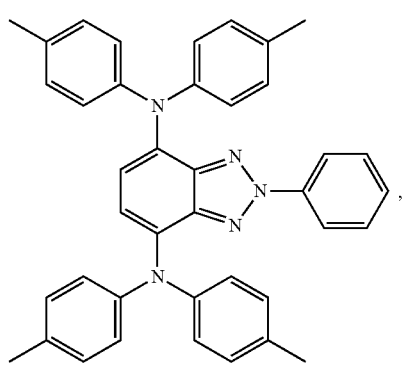

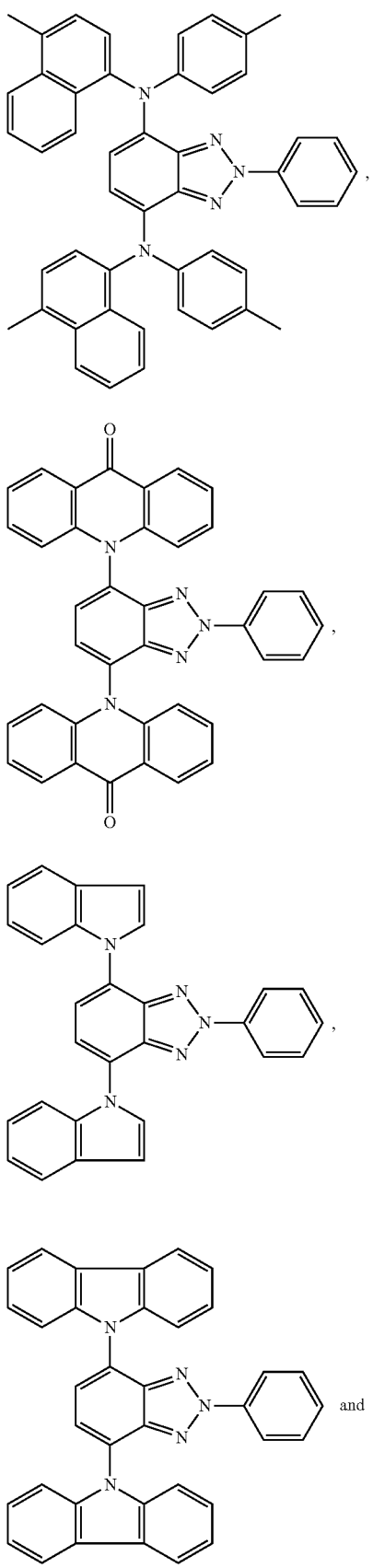

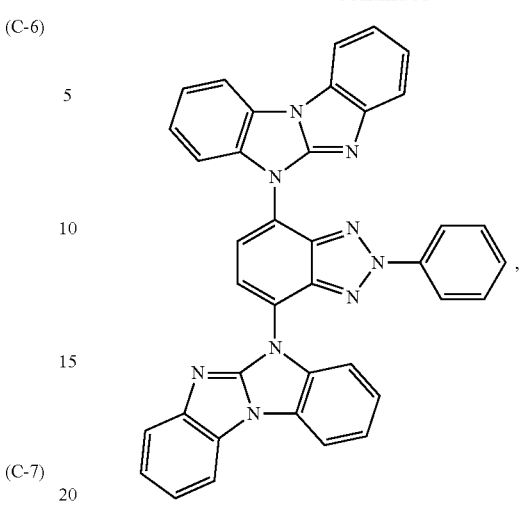

Among compounds of formula (Ic) those are preferred which are substituted by donor groups of formula (Xa), especially groups of formula

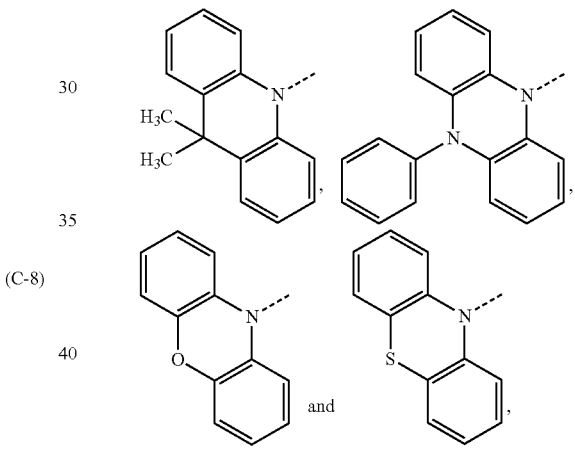

such as, for example, compounds (C-1), (C-2), (C-3) and (0-4).

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_6$-$C_{10}$aryl, which optionally can be substituted, is typically phenyl, naphthyl, especially 1-naphthyl, or 2-naphthyl, or biphenylyl, which may be unsubstituted or substituted by one, or more $C_1$-$C_8$alkyl, $C_1$-$C_8$alkoxy and/or $C_6$-$C_{10}$aryloxy groups, especially $C_1$-$C_8$alkyl, $C_1$-$C_8$alkoxy groups.

$C_6$-$C_{10}$aryloxy, which optionally can be substituted by one, or more $C_1$-$C_8$alkyl and/or $C_1$-$C_8$alkoxy groups, is typically phenoxy, 1-naphthoxy, or 2-naphthoxy.

The compounds of formula (I) can be used as host in combination with a fluorescent guest material in the emitting layer of an organic EL element. Known fluorescent materials are usable as the fluorescent guest material. Examples of the fluorescent guest material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative. Examples are 2,5,8,11-tetra-tert-butylperylene (TBPe), 9,10-bis[N,N-di-(p-tolyl)-amino]anthracene (TTPA), 2,8-di-tert-butyl-5,11-bis(4-tert-butylphenyl)-6,12-diphenyltetracene (TBRb) and dibenzo{[f,f']-4,4',7,7'-tetraphenyl}diindeno[1,2,3-cd:1',2',3'-Im]perylene (DBP). In case of using the compound of formula (I) as host material, the content of the compound of formula (I) in the light-emitting layer falls within the range of 51 to 99 wt %, preferably 80 to 99 wt %.

Alternatively, the compounds of formula (I) can be used as guest in combination with a host material in the emitting layer of an organic EL element. In said embodiment the compound of formula (I), i.e. the organic light-emitting material, has preferably a difference between excited singlet energy and excited triplet energy ($\Delta E_{ST}$) of 0.5 eV or less, more preferably $\Delta E_{ST}$ of 0.35 eV or less. The organic light-emitting material may be used alone in the light-emitting layer. However, as necessary, for the purpose of, for example, confining, in the organic light-emitting material, singlet excitons and triplet excitons generated in the organic light-emitting material, the organic light-emitting material of the present invention and an organic compound which has a higher value of at least any one of excited singlet energy and excited triplet energy than those of the organic light-emitting material and serves as a host material are preferably used in the light-emitting layer. At least any one of the excited singlet energy ($S_{1h}$) and excited triplet energy ($T_{1h}$) of the host compound is preferably higher by 0.1 eV or more, particularly preferably higher by 0.2 eV or more than the excited singlet energy ($S_{1g}$) and excited triplet energy ($T_{1g}$) of the organic light-emitting material of the present invention. That is, it is preferred that one or both of $(S_{1h})-(S_{1g})$ >0.1 eV and $(T_{1h})-(T_{1g})$>0.1 eV be satisfied and it is more preferred that one or both of $(S_{1h})-(S_{1g})$>0.2 eV and $(T_{1h})-(T_{1g})$>0.2 eV be satisfied.

The organic EL element of the present invention has, as essential layers, an anode, a hole-transporting layer, a light-emitting layer, and a cathode.

Further, the organic EL element of the present invention may have, as layers other than the essential layers, an electron-transporting layer, an electron-injecting layer, an electron-blocking layer, a hole-blocking layer, and an exciton element layer. In addition, the hole-transporting layer may be a hole-injecting/transporting layer having a hole-injecting function and the electron-transporting layer may be an electron-injecting/transporting layer having an electron-injecting function.

The organic EL element of the present invention may comprise in this order: a substrate, an anode, a hole-injecting layer, a hole-transporting layer, a light-emitting layer, an electron-transporting layer and a cathode. Alternatively, the cathode, the electron-transporting layer, the light-emitting layer, the hole-transporting layer, and the anode may be laminated on the substrate in the stated order.

Substrate

The organic EL element of the present invention is preferably supported by a substrate. The substrate is not particularly limited and may be any substrate which is conventionally used in an organic EL element. For example, a substrate formed of glass, transparent plastic, quartz, or the like may be used.

Anode

Preferably used as the anode in the organic EL element is one using, as an electrode substance, any of a metal, an alloy, an electrically conductive compound, and a mixture thereof with a high work function (4 eV or more). Specific examples of such electrode substance include metals such as Au and conductive transparent materials such as CuI, indium tin oxide (ITO), $SnO_2$, and ZnO. Further, a material capable of producing an amorphous transparent conductive film such as IDIXO ($In_2O_3$—ZnO) may be used. In the production of the anode, it is possible to form any of those electrode substances into a thin film by a method such as vapor deposition or sputtering, and then form a pattern having a desired shape by a photolithographic method. Alternatively, in the case of using a coatable substance such as an organic conductive compound, it is also possible to employ a wet film-forming method of a printing mode, a coating mode, or the like.

Cathode

Meanwhile, used as the cathode is one using, as an electrode substance, any of a metal (referred to as electron-injecting metal), an alloy, an electrically conductive compound, and a mixture thereof with a low work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, from the viewpoints of electron-injecting property and durability against oxidation and the like, a mixture of an electron-injecting metal and a second metal, which has a work function value higher than that of the electron-injecting metal and is a stable metal, such as a magnesium/silver mixture, a magnesium/aluminum mixture, a magnesium/indium mixture, an aluminum/aluminum oxide ($Al_2O_3$) mixture, a lithium/aluminum mixture, or aluminum is suitable. It should be noted that a case where any one of the anode and the cathode of the organic EL element is transparent or translucent in order to transmit emitted light is advantageous because light emission luminance is improved.

Light-Emitting Layer

The light-emitting layer is a layer which emits light after excitons have been generated through the recombination of holes and electrons injected respectively from an anode and a cathode. The light-emitting layer preferably includes an organic light-emitting material and a host material. As the organic light-emitting material, there may be used one kind or two or more kinds selected from the compounds of formula (I). In order that the organic EL element of the present invention exhibits high luminous efficiency, it is important to confine, in the organic light-emitting material, singlet excitons and triplet excitons generated in the organic light-emitting material. Accordingly, it is preferred to use the host material in addition to the organic light-emitting material in the light-emitting layer. As the host material, there may be used an organic compound having a higher value of at least any one of excited singlet energy and excited triplet energy than those of the organic light-emitting material of the present invention. This allows singlet excitons and triplet excitons generated in the organic light-emitting material of the present invention to be confined in the molecule of the organic light-emitting material of the present invention and allows the luminous efficiency to be exhibited sufficiently. In the organic EL element of the present invention, light is emitted from the organic light-emitting material of the present invention included in the light-emitting layer.

In case of using the host material, the content of the organic light-emitting material of the present invention in the light-emitting layer fall within the range of 1 to 50 wt %, preferably 1 to 20 wt %.

The host material in the light-emitting layer is preferably an organic compound which has a hole-transporting ability and/or an electron-transporting ability, prevents an emission wavelength from becoming longer, and has a high glass transition temperature.

The host material may be a polymer, for example poly (N-vinylcarbazole) or polysilane. The host material may, however, be a small molecule, for example 4,4'-N,N'-dicarbazolebiphenyl (CDP=CBP), 2,6-bis(N-carbazolyl)phenyl (mCP), 3,3-di(9H-carbazol-9-yl)bi-phenyl (mCBP)

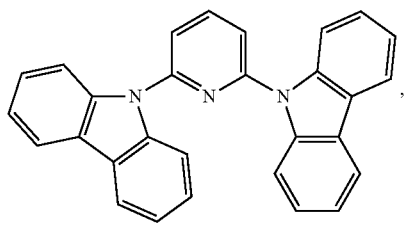

(PYD2)

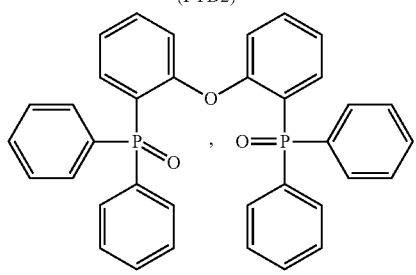

(DPEPO)

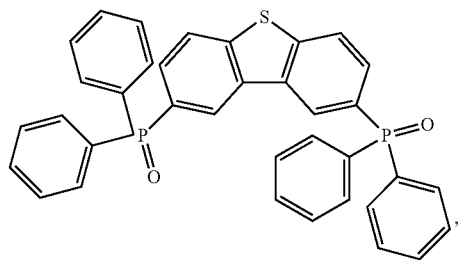

(PPT)

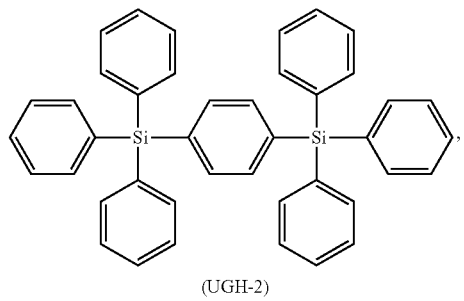

(UGH-2)

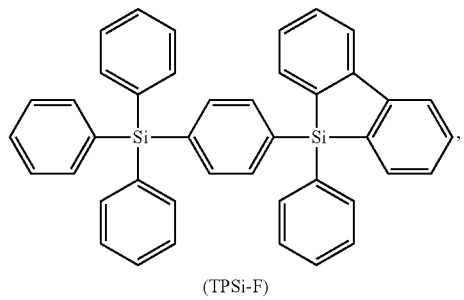

(TPSi-F)

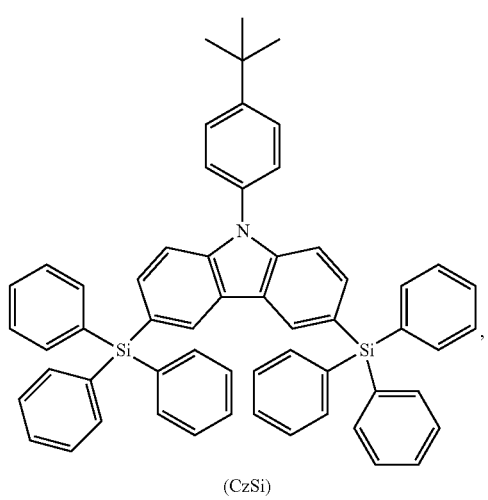

(CzSi)

-continued

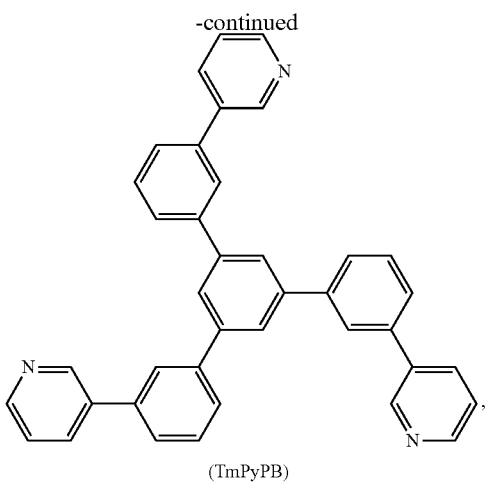

(TmPyPB)

or tertiary aromatic amines, for example 4-carbazol-9-yl-N, N-bis(4-carbazol-9-ylphenyl)aniline (TCTA).

Injecting Layer

The injecting layer refers to a layer to be provided between an electrode and an organic layer for the purposes of reducing a driving voltage and improving a light emission luminance. The injecting layer includes a hole-injecting layer and an electron-injecting layer, and may be provided between the anode and the light-emitting layer or the hole-transporting layer, and between the cathode and the light-emitting layer or the electron-transporting layer. The injecting layer may be provided as necessary.

Customarily used hole injection materials include α-NPD, CuPc, MTDATA, or dipyrazino[2,3-f:2',3'-h]quinoxaline-2,3,6,7,10,11-hexacarbonitrile (HAT-CN). Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly (4-styrenesulfonate) also called PEDOT/PSS.

Lithium-comprising organometallic compounds such as 8-hydroxyquinolatolithium (Liq), CsF, NaF, KF, $Cs_2CO_3$ or LiF may be applied between the electron transport layer and the cathode as an electron injection layer in order to reduce the operating voltage.

Blocking Layer

The blocking layer is capable of blocking charges (electrons or holes) and/or excitons present in the light-emitting layer from diffusing to the outside of the light-emitting layer. The electron-blocking layer may be arranged between the light-emitting layer and the hole-transporting layer, and blocks electrons from passing through the light-emitting layer toward the hole-transporting layer. Similarly, the hole-blocking layer may be arranged between the light-emitting layer and the electron-transporting layer, and blocks holes from passing through the light-emitting layer toward the electron-transporting layer. The blocking layer may also be used for blocking excitons from diffusing to the outside of the light-emitting layer. That is, the electron-blocking layer and the hole-blocking layer may each have a function of an exciton-blocking layer as well. The electron-blocking layer or exciton-blocking layer as used herein is meant to include a layer having a function of an electron-blocking layer and an exciton-blocking layer in one layer.

Hole-Blocking Layer

The hole-blocking layer has a function of the electron-transporting layer in a broad sense. The hole-blocking layer has a role in blocking holes from reaching the electron-transporting layer while transporting electrons. This can improve the probability of recombination of electrons and holes in the light-emitting layer. As a material for the hole-blocking layer, a material for the electron-transporting layer to be described below may be used as necessary.

Electron-Blocking Layer

The electron-blocking layer has a function of transporting holes in a broad sense. The electron-blocking layer has a role in blocking electrons from reaching the hole-transporting layer while transporting holes. This can improve the probability of recombination of electrons and holes in the light-emitting layer.

Exciton-Blocking Layer

The exciton-blocking layer refers to a layer for blocking excitons, which are generated by the recombination of holes and electrons in the light-emitting layer, from diffusing to a charge-transporting layer. The insertion of this layer allows excitons to be efficiently confined in the light-emitting layer, which can improve the luminous efficiency of an element. The exciton-blocking layer may be inserted on any of the anode side and the cathode side of the adjacent light-emitting layer, and may be simultaneously inserted on both of the sides. That is, when the exciton-blocking layer is provided on the anode side, the layer may be inserted between the hole-transporting layer and the light-emitting layer so as to be adjacent to the light-emitting layer. When the exciton-blocking layer is inserted on the cathode side, the layer may be inserted between the light-emitting layer and the cathode so as to be adjacent to the light-emitting layer. Further, the hole-injecting layer, the electron-blocking layer, and the like may be provided between the anode and the exciton-blocking layer adjacent to the anode side of the light-emitting layer, and the electron-injecting layer, the electron-transporting layer, the hole-blocking layer, and the like may be provided between the cathode and the exciton-blocking layer adjacent to the cathode side of the light-emitting layer. In the case of providing the blocking layer, it is preferred that at least any one of the excited singlet energy and excited triplet energy of a material to be used as the blocking layer be higher than the excited singlet energy and excited triplet energy of a light-emitting material.

Hole blocker materials typically used are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1, 3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2-bipyridyl, 2-phenyl-9,10-di (naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris (2,4,6-trimethyl-3-(pyridin-3-yl)phenyl)borane, 2,9-bis (naphthalene-2-yl)-4,7-diphenyl-1,10-phenanthroline, 1-methyl-2-(4-(naphthalene-2-yl)phenyl)-1H-imidazo[4,5-f][1,10]phenanthroline,

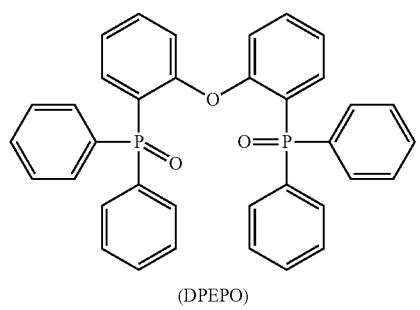 [SMILES: O=P(c1ccccc1)(c1ccccc1)c1ccccc1Oc1ccccc1P(=O)(c1ccccc1)c1ccccc1]

(DPEPO)

and 2,4,6-tris(biphenyl-3-yl)-1,3,5-triazine (T2T).

Hole-Transporting Layer

The hole-transporting layer is formed of a hole-transporting material having a function of transporting holes. The hole-transporting layer may be provided in a single layer or a plurality of layers.

The hole-transporting material has any of hole-injecting or -transporting property and electron-blocking property, and may be an organic material or an inorganic material. An applicable known hole-transporting material is exemplified by a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, or a conducting polymeric oligomer, particularly a thiophene oligomer. However, preferably used are a porphyrin compound, an aromatic tertiary amine compound, and a styrylamine compound, and more preferably used is an aromatic tertiary amine compound. Customarily used hole-transporting molecules are selected from the group consisting of

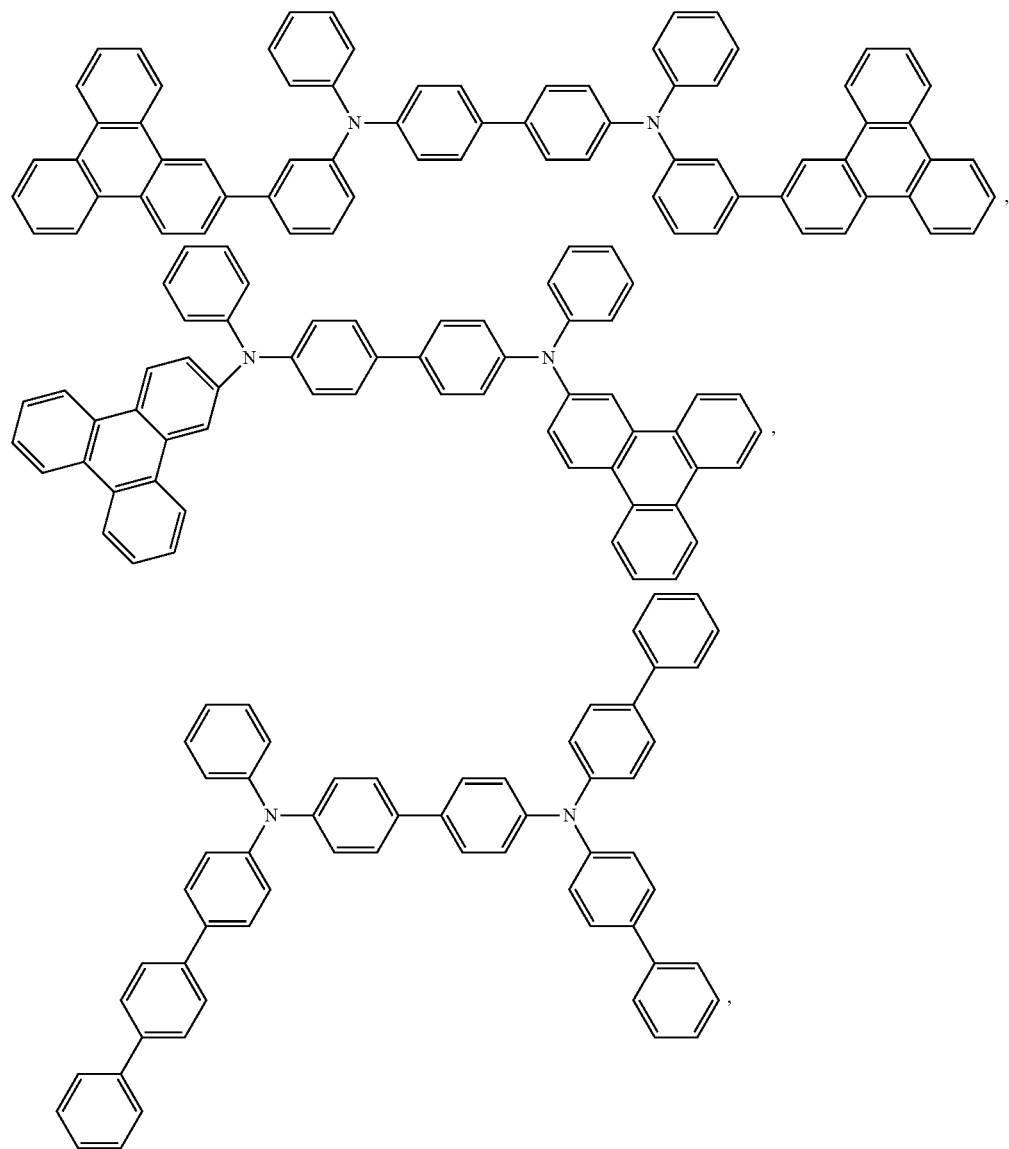

(4-phenyl-N-(4-phenylphenyl)-N-[4-[4-(N-[4-(4-phenylphenyl)phenyl]anilino)phenyl]phenyl]aniline)

-continued
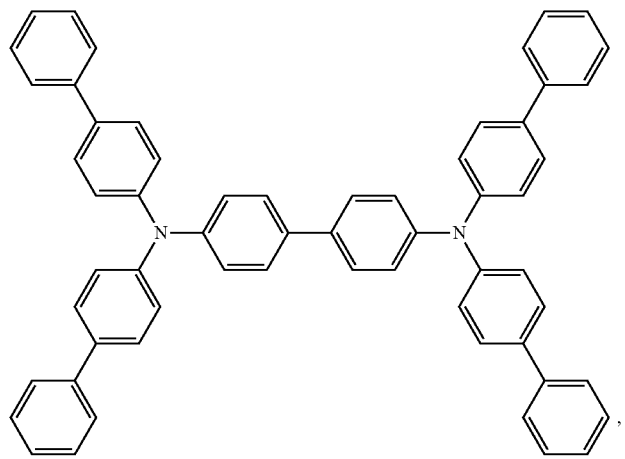
(4-phenyl-N-(4-phenylphenyl)-N-[4-[4-(4-phenyl-N-(4-phenylphenyl)anilino)phenyl]phenyl]aniline)
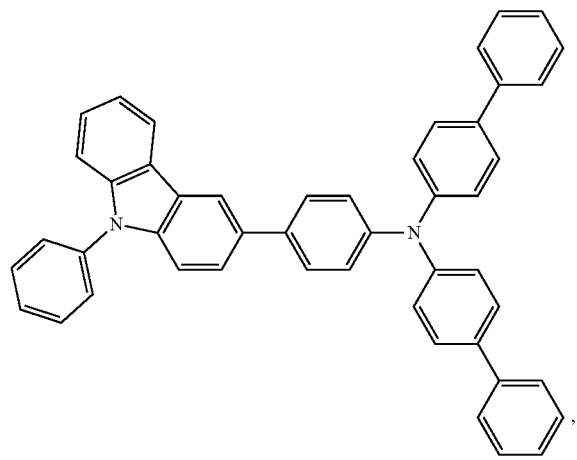
(4-phenyl-N-[4-(9-phenylcarbazol-3-yl)phenyl]-N-(4-phenylphenyl)aniline)
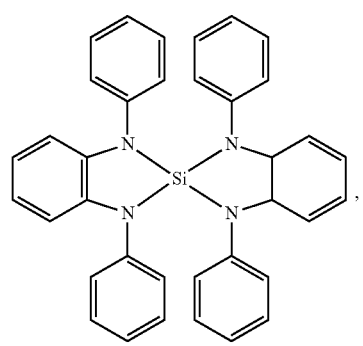
(1,1′,3,3′-tetraphenylspiro[1,3,2-benzodiazasilole-2,2′-3a,7a-dihydro-1,3,2-benzodiazasilole])

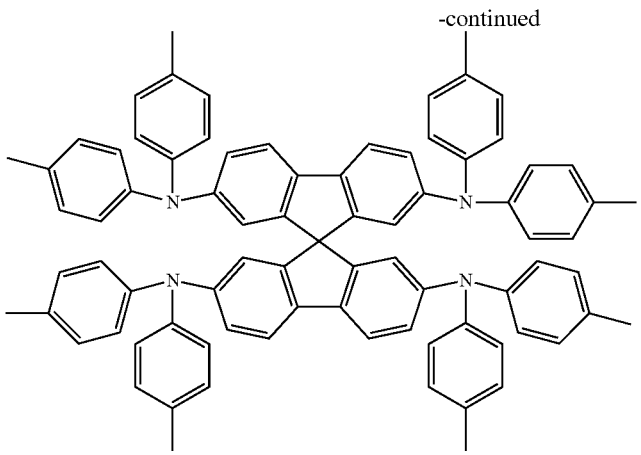

(N2,N2,N2', N2', N7,N7,N7', N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines, and CzSi. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Electron-Transporting Layer

The electron-transporting layer is formed of a material having a function of transporting electrons. The electron-transporting layer may be provided in a single layer or a plurality of layers.

An electron-transporting material (may also serve as a hole-blocking material) has only to have a function of transporting electrons, which are injected from the cathode, to the light-emitting layer. An applicable electron-transporting layer is exemplified by a nitro-substituted fluorene derivative, a diphenylquinone derivative, a thiopyran dioxide derivative, carbodiimide, a fluorenylidenemethane derivative, an anthraquinodimethane derivative, an anthrone derivative, or an oxadiazole derivative. In addition, in oxadiazole derivative, a thiadiazole derivative in which an oxygen atom of an oxadiazole ring is substituted by a sulfur atom, or a quinoxaline derivative having a quinoxaline ring known as an electron-withdrawing group may also be used as the electron-transporting material. In addition, a polymer material obtained by introducing any of those materials into a polymer chain, or a polymer material including any of those materials in a polymer main chain may also be used. Suitable electron-transporting materials comprise 1,3,5-tris(N-phenyl-2-benzylimidazolyl)benzene (TPBi),

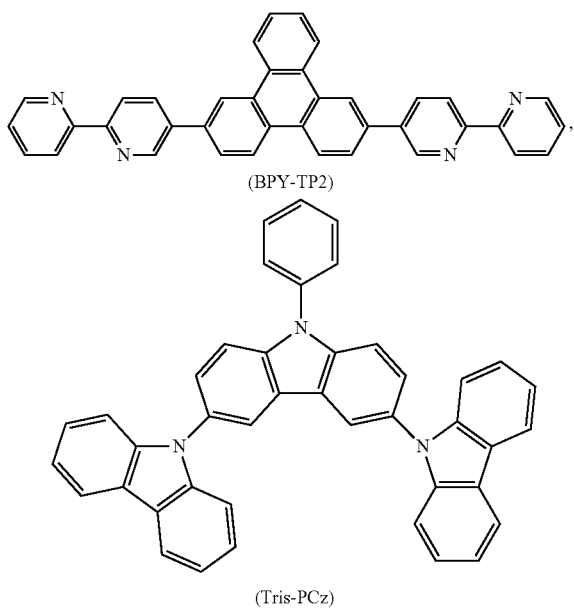

(BPY-TP2)

(Tris-PCz)

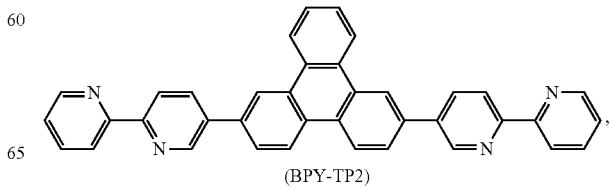

(BPY-TP2)

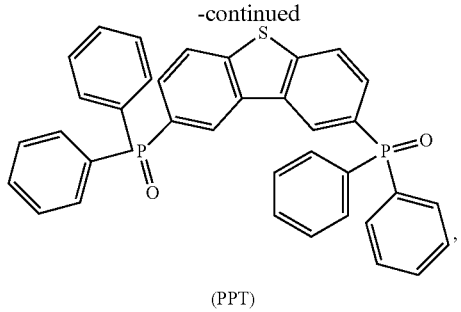

(PPT)

metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

Examples of possible element structures are shown below:

ITO (100 nm)/α-NPD (35 nm)/CBP: 6% by weight cpd. of formula (I) (15 nm)/TPBi (65 nm)/LiF (0.8 nm)/Al (80 nm)

ITO (100 nm)/α-NPD (40 nm)/mCP/PPT: 6% by weight cpd. of formula (I) (20 nm)/PPT (40 nm)/LiF (0.8 nm)/Al (80 nm)

ITO (30-100 nm)/α-NPD (60 nm)/mCP: 6% by weight cpd. of formula (I) (20 nm)/Bphen (40 nm)/MgAg (100 nm)/Ag (20 nm)

ITO (30-100 nm)/α-NPD (60 nm)/PYD2: 6% by weight cpd. of formula (I) (20 nm)/Bphen (40 nm)/MgAg (100 nm)/Al (20 nm)

ITO/α-NPD (35 nm)/6% by weight cpd. of formula (I): CBP (15 nm)/TPBi (65 nm)/LiF (0.8 nm)/Al (80 nm)

ITO (100 nm)/HAT-CN (10 nm)/Tris-PCz (30 nm)/CBP: 3, 6, 10, or 15% by weight cpd. of formula (I) (30 nm)/BPY-TP2 (40 nm)/LiF (0.8 nm)/Al (100 nm)

ITO (100 nm)/α-NPD (35 nm)/CBP (10 nm)/DPEPO: 6 to 12% by weight cpd. of formula (I) (15 nm)/DPEPO (10 nm)/TPBi (65 nm)/LiF (0.5 nm)/Al (80 nm)

ITO (100 nm)/HAT-CN (10 nm)/Tris-PCz (30 nm)/mCBP: 6 to 12% by weight cpd. of formula (I) (30 nm)/T2T (10 nm)/Bpy-TP2 (40 nm)/LiF (0.8 nm)/Al (100 nm)

ITO (100 nm)/α-NPD (30 nm)/TCTA (20 nm)/CzSi (10 nm)/DPEPO: 6 to 12% by weight cpd. of formula (I) (20 nm)/DPEPO (10 nm)/TPBi (30 nm)/LiF (0.8 nm)/Al (100 nm)

ITO: indium/tin oxide; α-NPD: 4,4'-bis[N-(1-naphthyl)-N-phenylamino]biphenyl;
CBP: 4,4'-N,N'-dicarbazolebiphenyl; TPBi: 1,3,5-tris(N-phenyl-2-benzylimidazolyl)benzene;
mCP: 2,6-bis(N-carbazolyl)pyridine; PPT:

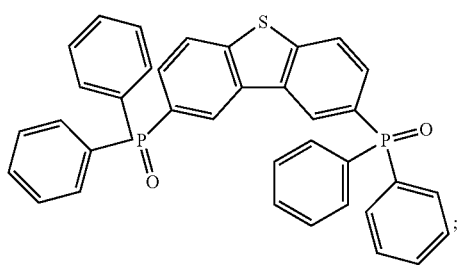

Bphen: 4,7-diphenyl-1,10-phenanthroline; PYD2:

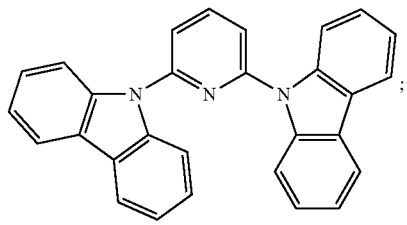 [SMILES: c1cc(-n2c3ccccc3c3ccccc32)nc(-n2c3ccccc3c3ccccc32)c1]

HAT-CN: dipyrazino[2,3-f:2',3'-h]quinoxaline-2,3,6,7,10,11-hexacarbonitrile; Tris-PCz:

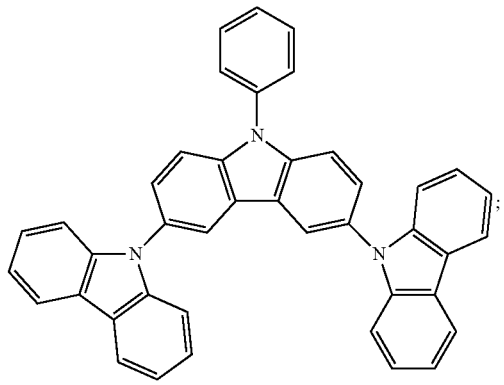

BPY-TP2:

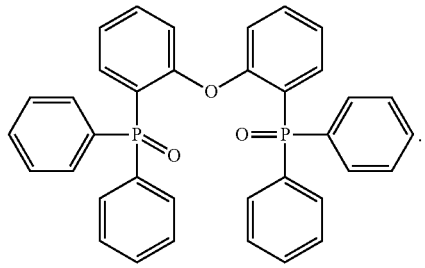

DPEPO:

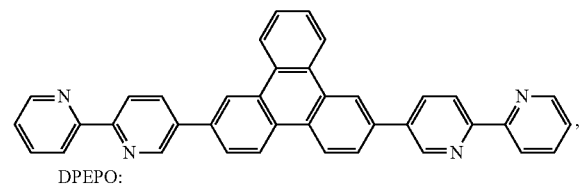

The organic EL element emits light when an electric field is applied between an anode and a cathode of the resultant element.

The organic EL element of the present invention may be applied to any of a single element, an element formed of a structure with arrangement in an array fashion, and a structure in which an anode and a cathode are arranged in an X-Y matrix fashion.

According to the present invention, there is provided an element having significantly improved luminous efficiency as compared to a conventional element using light emission from a singlet state by incorporating the organic light-emitting material having a specific skeleton of the present invention into the light-emitting layer. The element can exhibit excellent performance when being applied to a full-color or multi-color panel. The element may also be utilized in a backlight, lighting, and the like.

Compounds of Formula

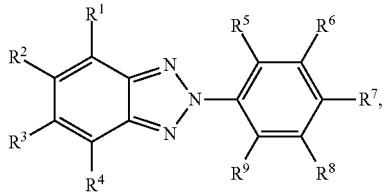 (I)

wherein

R¹, R², R³ and R⁴ are independently of each other H, D, F, Cl, a $C_1$-$C_{25}$alkyl group, a $C_1$-$C_{25}$alkoxy group, a $C_6$-$C_{10}$aryloxy group, or a donor group of formula

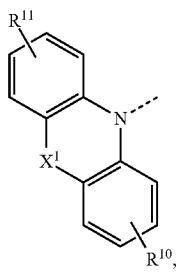 (Xa)

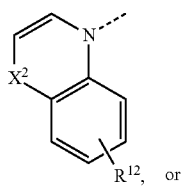 (Xb)

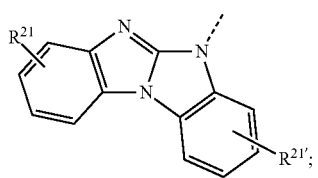 (Xd)

R⁵, R⁶, R⁷, R⁸ and R⁹ are independently of each other H, D, F, Cl, a $C_1$-$C_{25}$alkyl group, a $C_1$-$C_{25}$alkoxy group, a $C_6$-$C_{10}$aryloxy group, a group of formula

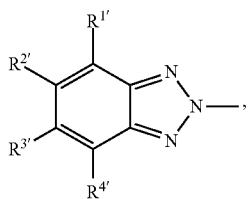

(Xa), (Xb), or (Xd);

R¹', R²', R³' and R⁴' are independently of each other H, D, F, Cl, a $C_1$-$C_{25}$alkyl group, a $C_1$-$C_{25}$alkoxy group, or a $C_6$-$C_{10}$aryloxy group;

R¹ and R² together form a group of formula

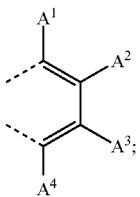

R¹' and R²' together form a group of formula

R³ and R⁴ together form a group of formula

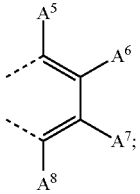

R³' and R⁴' together form a group of formula

R⁵ and R⁶ together form a group of formula

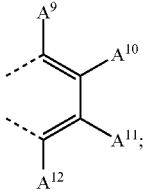

and/or
R⁸ and R⁹ together form a group of formula

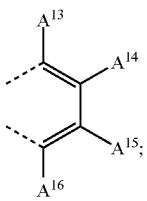

A¹, A², A³, A⁴, A⁵, A⁶, A⁷ and A⁸ are independently of each other H, D, F, Cl, a $C_1$-$C_{25}$alkyl group, or a donor group of formula (Xa), (Xb), or (Xd);

$A^9$, $A^{10}$, $A^{11}$, $A^{12}$, $A^{13}$, $A^{14}$, $A^{15}$ and $A^{16}$ are independently of each other H, D, F, Cl, a $C_1$-$C_{25}$alkyl group, or a donor group of formula (Xa), (Xb), or (Xd);

$X^1$ and $X^2$ are independently of each other O, S, N($R^{15}$), C($R^{16}$)($R^{17}$), B($R^{18}$), or Si($R^{19}$)($R^{20}$) and $R^{10}$, $R^{11}$, $R^{12}$, $R^{21}$ and $R^{21'}$ are independently of each other H, D, F, Cl, or a $C_1$-$C_{25}$alkyl group;

$R^{15}$, $R^{16}$, $R^{17}$, $R^{18}$, $R^{19}$ and $R^{20}$ are independently of each other H, a $C_1$-$C_{25}$alkyl group, or a $C_6$-$C_{14}$aryl group;

with the proviso that at least one donor group of formula (Xa), (Xb), or (Xd) is present in the compound of formula (I), are new and form a further subject of the present invention.

Compounds of formula (I) are preferred, wherein $R^1$, $R^2$, $R^3$, $R^4$, $R^6$, $R^7$, $R^8$ and $R^9$ are independently of each other H, a $C_1$-$C_{25}$alkyl group, a $C_1$-$C_{25}$alkoxy group, a $C_6$-$C_{10}$aryloxy group, a donor group of formula

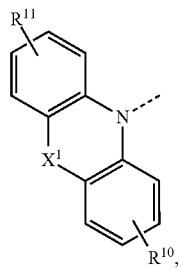 (Xa)

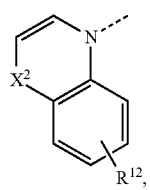 (Xb)

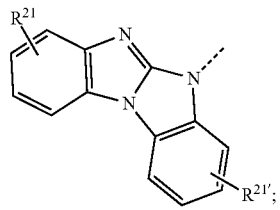 (Xd)

or
$R^1$ and $R^2$ together form a group of formula

and/or
$R^8$ and $R^9$ together form a group of formula

$R^5$ is H, a $C_1$-$C_{25}$alkyl group, a group of formula

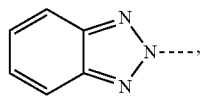

or a donor group of formula (Xa), (Xb), or (Xd);

$X^1$ and $X^2$ are independently of each other O, S, N($R^{15}$), or C($R^{16}$)($R^{17}$); and $R^{10}$, $R^{11}$, $R^{12}$, $R^{21}$ and $R^{21'}$ are independently of each other H, or a $C_1$-$C_{25}$alkyl group;

$R^{15}$ is a group of formula

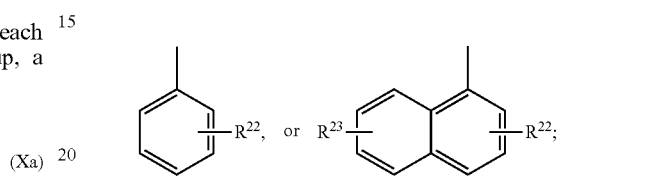

$R^{16}$ and $R^{17}$ are independently of each other H, a $C_1$-$C_{25}$alkyl group;

$R^{22}$ and $R^{23}$ are independently of each other H, a $C_1$-$C_{25}$alkyl group, a $C_1$-$C_{25}$alkoxy group, or a $C_6$-$C_{10}$aryloxy group;

with the proviso that at least one of $R^1$, $R^2$, $R^3$, $R^4$, $R^5$, $R^6$, $R^7$, $R^8$ and $R^9$ is a donor group of formula (Xa), (Xb), or (Xd).

In a preferred embodiment the present invention is directed to compounds of formula

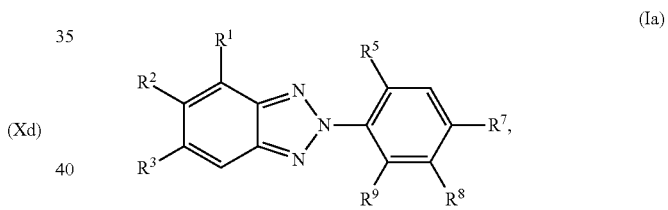 (Ia)

wherein
$R^1$ and $R^2$ are independently of each other H, or a $C_1$-$C_{25}$alkyl group, or
$R^1$ and $R^2$ together form a group of formula

$R^3$, $R^7$ and $R^8$ are independently of each other H, a $C_1$-$C_{25}$alkyl group, or a donor group of formula

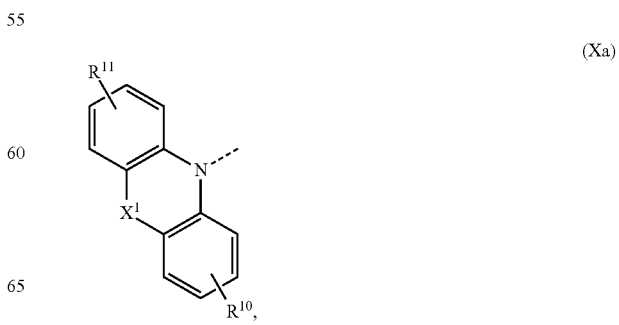 (Xa)

-continued

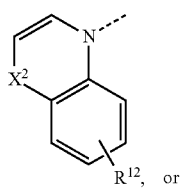
(Xb)

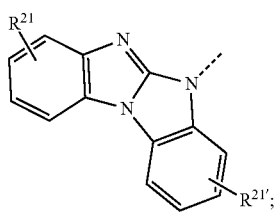
(Xd)

R⁵ is H, a $C_1$-$C_{25}$alkyl group, a group of formula

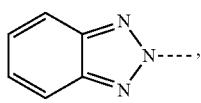

or a donor group of formula (Xa), (Xb), or (Xd);
R⁹ is H, or
R⁸ and R⁹ together form a group of formula

X¹ and X² are independently of each other O, S, N(R¹⁵), or C(R¹⁶)(R¹⁷);
R¹⁰, R¹¹, R¹², R²¹ and R²¹' are independently of each other H, or a $C_1$-$C_{25}$alkyl group;
R¹⁵ is a group of formula

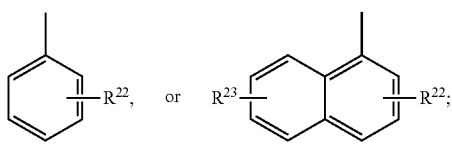

R¹⁶ and R¹⁷ are independently of each other H, a $C_1$-$C_{25}$alkyl group;
R²² and R²³ are independently of each other H, or a $C_1$-$C_{25}$alkyl group;
with the proviso that at least one of R³, R⁵ and R⁷ is a donor group of formula (Xa), (Xb), or (Xd).
Compounds of formula

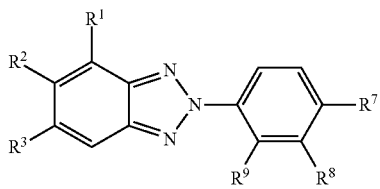
(Ia')

are more preferred, wherein R¹ and R² are independently of each other H, or a $C_1$-$C_{25}$alkyl group, or
R¹ and R² together form a group of formula

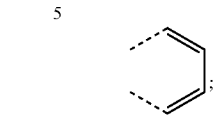

R³ is H, a $C_1$-$C_{25}$alkyl group, or a donor group of formula

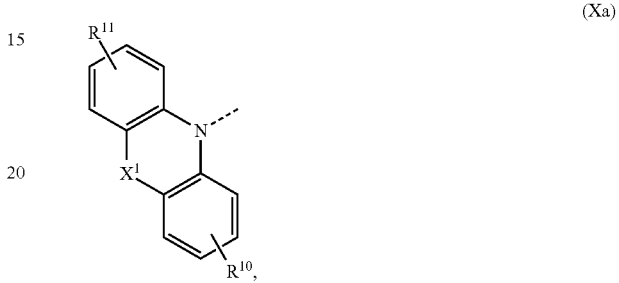
(Xa)

(Xb)

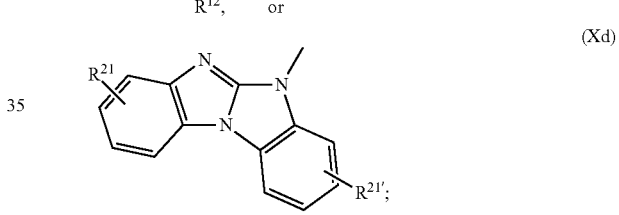
(Xd)

R⁷ is H, a $C_1$-$C_{25}$alkyl group, or a donor group of formula (Xa), (Xb), or (Xd);
R⁸ and R⁹ are H, or
R⁸ and R⁹ together form a group of formula

X¹ and X² are independently of each other O, S, N(R¹⁵), or C(R¹⁶)(R¹⁷);
R¹⁰, R¹¹, R¹², R²¹ and R²¹' are independently of each other H, or a $C_1$-$C_{25}$alkyl group;
R¹⁵ is a group of formula

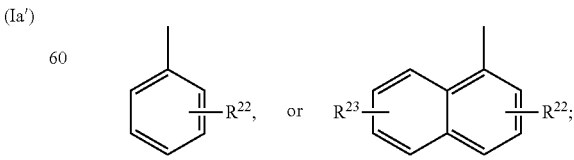

R¹⁶ and R¹⁷ are independently of each other H, a $C_1$-$C_{25}$alkyl group;

$R^{22}$ and $R^{23}$ are independently of each other H, or a $C_1$-$C_{25}$alkyl group;

with the proviso that at least one of $R^3$ and $R^7$ is a donor group of formula (Xa), (Xb), or (Xd). Compounds of formula

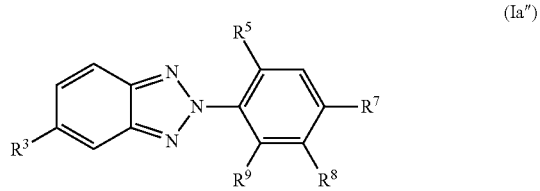
(Ia'')

are even more preferred, wherein
$R^3$ and $R^5$ are H and $R^7$ is a donor group of formula

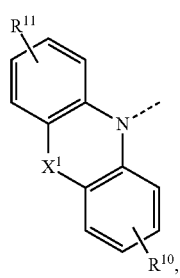
(Xa)

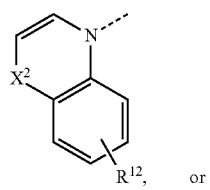
(Xb)

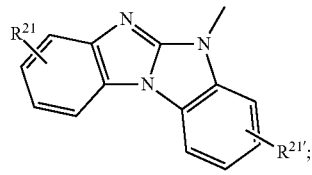
(Xd)

or
$R^3$ is a donor group of formula (Xa), (Xb), or (Xd) and $R^5$ and $R^7$ are H; or
$R^5$ is a donor group of formula (Xa), (Xb), or (Xd) and $R^3$ and $R^7$ are H; or
$R^3$ and $R^7$ are a donor group of formula (Xa), (Xb), or (Xd) and $R^5$ is H; or

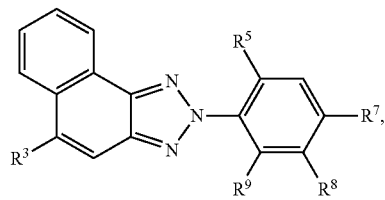
(Ia''')

wherein
$R^3$ and $R^5$ are H and $R^7$ is a donor group of formula (Xa), (Xb), or (Xd); or $R^3$ is a donor group of formula (Xa), (Xb), or (Xd) and $R^5$ and $R^7$ are H; or
$R^5$ is a donor group of formula (Xa), (Xb), or (Xd) and $R^3$ and $R^7$ are H; or
$R^3$ and $R^7$ are a donor group of formula (Xa), (Xb), or (Xd) and $R^5$ is H; and
$X^1$ and $X^2$ are independently of each other O, S, N($R^{15}$), or C($R^{16}$)($R^{17}$);
$R^8$ and $R^9$ are H, or
$R^8$ and $R^9$ together form a group of formula

;

$R^{10}$, $R^{11}$, $R^{12}$, $R^{21}$ and $R^{21'}$ are independently of each other H, or a $C_1$-$C_{25}$alkyl group;
$R^{15}$ is a group of formula

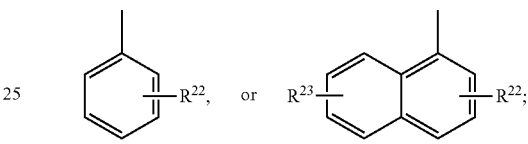

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group.

Most preferred are compound of formula (Ia''), wherein
$R^5$, $R^8$ and $R^9$ are H;
$R^3$ is H and W is a donor group of formula

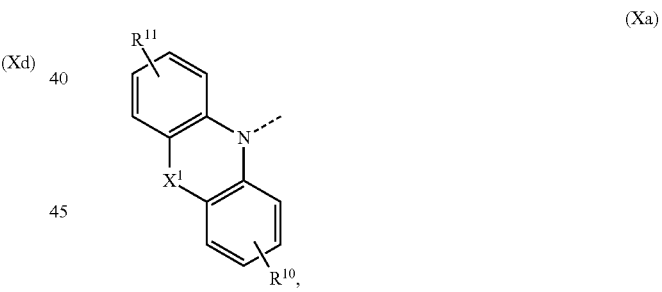
(Xa)

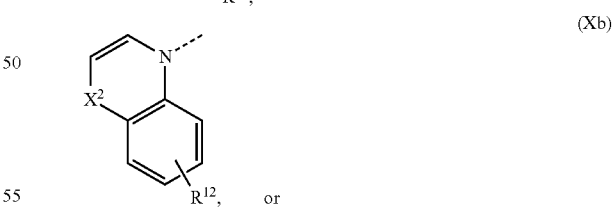
(Xb)

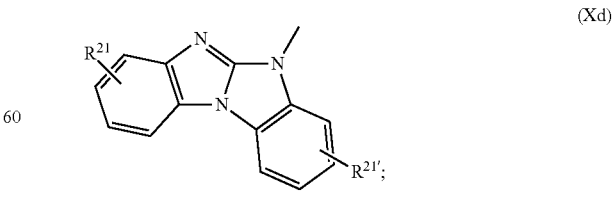
(Xd)

or
$R^3$ is a donor group of formula (Xa), (Xb), or (Xd) and $R^7$ is H; or $R^3$ and $R^7$ are a donor group of formula (Xa), (Xb), or (Xd); or a compound of formula (Ia'''), wherein
$R^5$, $R^8$ and $R^9$ are H;
$R^3$ is H and W is a donor group of formula (Xa), (Xb), or (Xd); or
$R^3$ is a donor group of formula (Xa), (Xb), or (Xd) and $R^7$ is H; or
$R^3$ and $R^7$ are a donor group of formula (Xa), (Xb), or (Xd) and
$X^1$ and $X^2$ are independently of each other O, S, N($R^{15}$), or C($R^{16}$)($R^{17}$);
$R^{10}$, $R^{11}$, $R^{12}$, $R^{21}$ and $R^{21'}$ are independently of each other H, or a $C_1$-$C_{25}$alkyl group;
$R^{15}$ is a group of formula

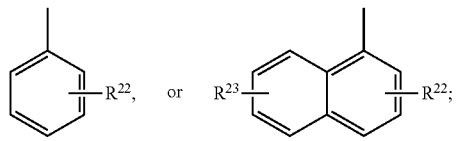

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group.

In another preferred embodiment the present invention is directed to compounds of formula

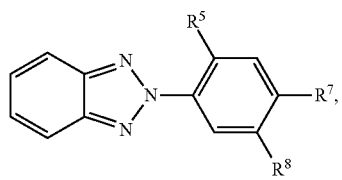

(Ib)

wherein
$R^5$ is a group of formula

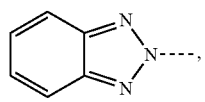

$R^7$ and $R^8$ are a donor group of formula

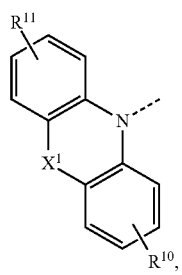

(Xa)

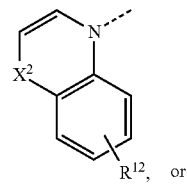

(Xb)

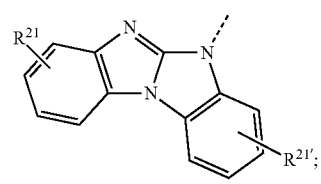

(Xd)

or
a compound of formula (Ib), wherein
$R^5$ is a donor group of formula (Xa), (Xb), or (Xd), and
$R^7$ and $R^8$ are independently of each other H, or a $C_1$-$C_{25}$alkyl group; and
$X^1$ and $X^2$ are independently of each other O, S, N($R^{15}$), or C($R^{16}$)($R^{17}$);
$R^{10}$, $R^{11}$, $R^{12}$, $R^{21}$ and $R^{21'}$ are independently of each other H, or a $C_1$-$C_{25}$alkyl group;
$R^{15}$ is a group of formula

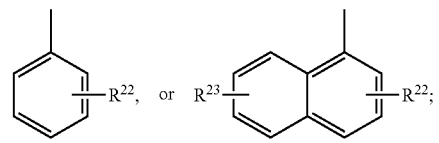

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group.

In another preferred embodiment the present invention is directed to compounds of formula

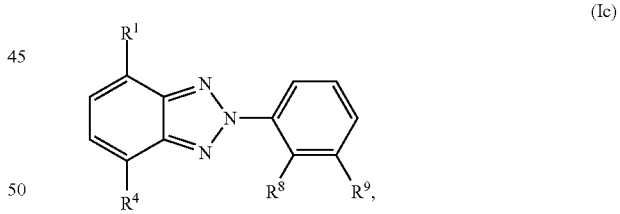

(Ic)

wherein
$R^1$ and $R^4$ are a donor group of formula

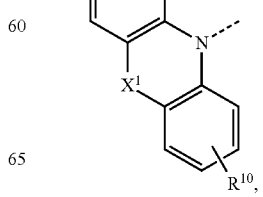

(Xa)

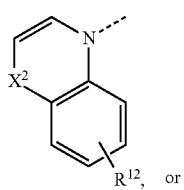
(Xb)

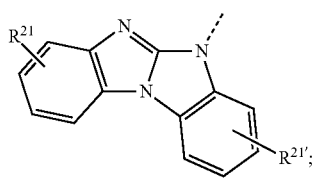
(Xd)

and $X^1$ and $X^2$ are independently of each other O, S, N($R^{15}$), or C($R^{16}$)($R^{17}$);

$R^8$ and $R^9$ are H, or $R^8$ and $R^9$ together form a group of formula

;

$R^{10}$, $R^{11}$, $R^{12}$, $R^{21}$ and $R^{21'}$ are independently of each other H, or a $C_1$-$C_{25}$alkyl group;

$R^{15}$ is a group of formula

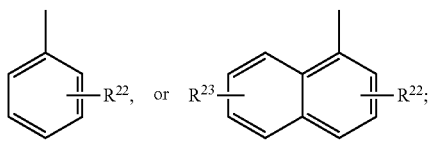

$R^{16}$ and $R^{17}$ are independently of each other H, or a $C_1$-$C_{25}$alkyl group;

$R^{22}$ and $R^{23}$ are independently of each other H, or a $C_1$-$C_{25}$alkyl group.

Examples of donor groups of formula (Xa) are a group of formula

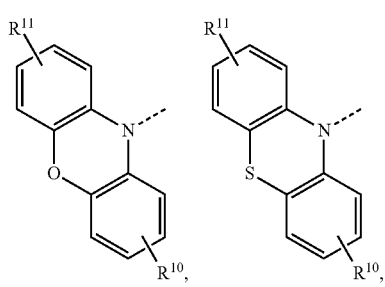

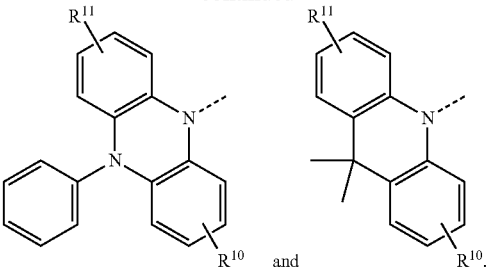

Groups of formula

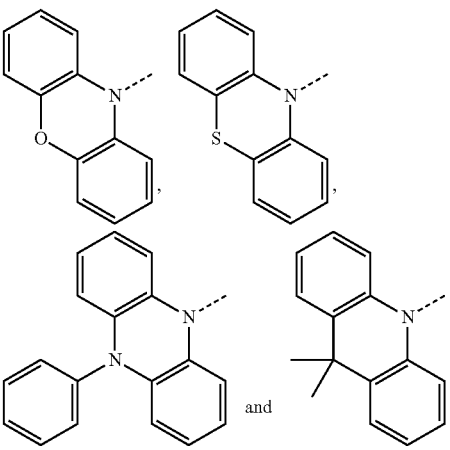

are preferred. Groups of formula

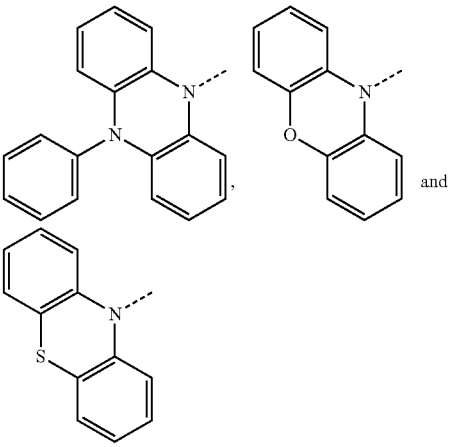

are most preferred.

Examples of the donor group of formula (Xb) are groups of formula

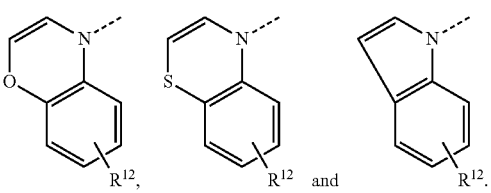

Groups of formula

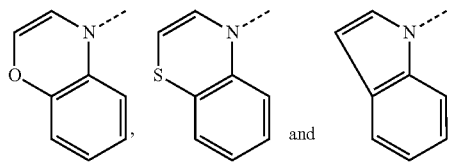

are preferred. A group of formula

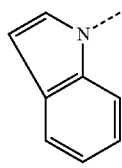

is most preferred.

Among the donor groups of formula (Xd) a group of formula

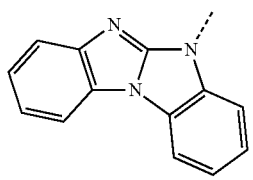

is preferred. The donor group is preferably a donor group of formula (Xa), wherein $X^1$ is O, S, $C(CH_3)(CH_3)$,

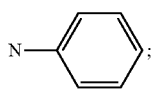

or a donor group of formula (Xb), wherein $X^2$ is a single bond and $R^{12}$ is H; or a donor group of formula (Xd), wherein $R^{21}$ and $R^{21'}$ are H.

Among the donor groups of formula (Xa), (Xb) and (Xd) donor groups of formula (Xa) and (Xc) are preferred. Donor groups of formula (Xa) are most preferred.

Among the donor groups of formula (Xa) groups of formula

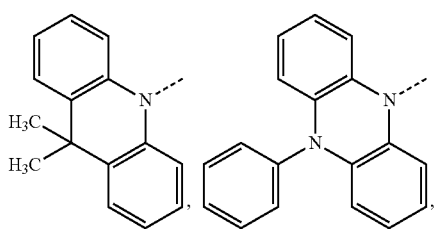

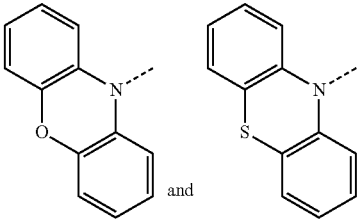

are most preferred.

The above compounds of formula (I) may used as host, or guest in the emitting layer of organic light emitting elements.

Accordingly, the present invention is also directed to a light-emitting layer and an organic light emitting element comprising the above compounds of formula (I).

The light-emitting layer comprises a light-emitting layer comprises
i) a compound of formula (I) as guest and a host material; or
ii) a compound of formula (I) as host and a fluorescent guest material.

The organic light-emitting element comprises a light-emitting layer comprising
i) a compound of formula (I) as guest and a host material; or
ii) a compound of formula (I) as host and a fluorescent guest material. The organic light-emitting element is characterized in that it emits delayed fluorescence and is described in more detail above.

The above compounds of formula (I) can be used in electrophotographic photoreceptors, photoelectric converters, sensors, dye lasers, solar cell devices and organic light emitting elements.

The benzotriazoles of the present invention can be synthesized using copper catalyzed Ullmann conditions or palladium catalyzed Buchwald-Hartwig conditions. Suitable benzotriazole base skeletons are either commercially available, or can be obtained by processes known to those skilled in the art. Reference is made to WO2005/054212.

The following examples are included for illustrative purposes only and do not limit the scope of the claims. Unless otherwise stated, all parts and percentages are by weight.

EXAMPLES

Example 1

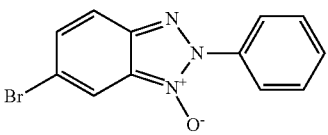 [SMILES: [O-][n+]1c2cc(Br)ccc2nn1-c1ccccc1]

a) Phenyl hydrazine HCl (0.39 mol) and NaOAc.3H$_2$O (0.59 mol) are placed in a 1.5 l flask with EtOH 550 ml. While stirring, 1-fluoro-4-bromo-2-nitrobenzene (0.20 mol) is added (by pouring). The slurry becomes slightly orange. The mixture is heated to reflux overnight (20 hours). After cooling to room temperature, the mixture is filtered and washed with EtOH. Without vacuum on the frit, water is added with stirring to dissolve the NaCl and NaF. Vacuum is applied and the process is repeated. Stirring twice with MeOH in the same manner and applying vacuum give a light orange solid. Volatiles are removed in vacuum. (Yield: 38.2%)

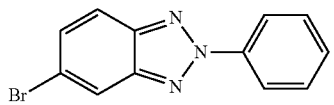 [SMILES: Brc1ccc2nn(-c3ccccc3)nc2c1]

b) The product from example 1a (0.11 mol), and sodium hydrogen sulfite (0.11 mol) are placed in a 250 ml 3 neck round balloon with 200 ml dimethyl formamide (DMF). While stirring, the reaction mixture is heated to 110° C. overnight. After cooling to room temperature, the mixture is poured into 300 ml ice water, and then the precipitate is filtered off and washed with 1000 ml water and 500 ml EtOH. Volatiles are removed in vacuum give a slightly beige powder (yield: 35.5%). $^1$H-NMR (ppm, CDCl$_3$): 8.15 (dd, 2H), 8.03 (d, 1H), 7.57-7.50 (m, 5H).

(A-1)

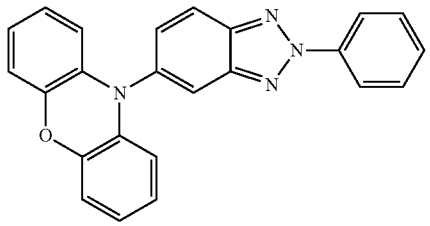

c) The product from example 1b (1.45 mmol), phenoxazine (1.75 mmol), palladium acetate (0.03 mmol), tri-tert-Buthylphosphine (0.06 mmol), sodium t-buthoxide (2.9 mmol) and 10 ml of toluene are placed in a 50 ml flask. The mixture is stirred at 110° C. overnight and cooled. The mixture is then poured into H$_2$O and extracted with ethylacetate. The organic layer is dried over MgSO$_4$ and concentrated by evaporation. Column chromatography of the crude product with dichloromethane/hexane (1:15-1:5) as eluent gives a yellow solid (yield: 81.9%). The product is subsequently purified using zone sublimation. 1H-NMR (ppm, CDCl$_3$): 8.33 (td, 3H), 8.24 (d, 1H), 7.69 (td, 2H), 7.60 (td, 1H), 7.45 (dd, 1H), 6.76 (dd, 2H), 6.72-6.61 (m, 4H), 5.97 (dd, 2H).

Example 2

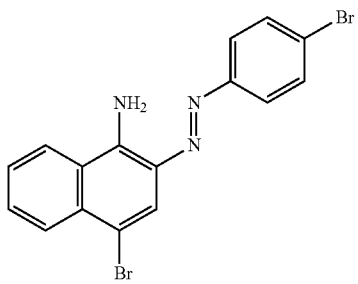 [SMILES: Nc1c(/N=N/c2ccc(Br)cc2)cc(Br)c2ccccc12]

a) 4-Bromoaniline (58.14 mmol) is dissolved in 200 ml water using 174 mmol HCl. The mixture is cooled to 0° C. and sodium nitrite (58.1 mmol) in 30 ml water is added dropwise over 30 minutes. After 45 minutes the diazonium salt is added via cannula to a mixture of 1-amino-4-bromonaphthalene (58.14 mmol) in 300 ml ethanol at 0° C. After 2 hours sodium carbonate (80.2 mmol) in 100 ml water is added dropwise, producing a pH of 7. After an additional 30 minutes the red precipitate is filtered and washed with water (2×300 ml). The brown-red solid is triturated in 100 ml methanol overnight, filtered and dried. The product is dried in vacuo to give a bright red solid (yield: 91.0%). $^1$H-NMR (ppm, (CD$_3$)$_2$SO): 8.59 (d, 1H), 8.12 (s, 1H), 8.07 (d, 1H), 8.04 (d, 2H), 7.82 (d, 1H), 7.76 (d, 2H), 7.70 (t, 1H).

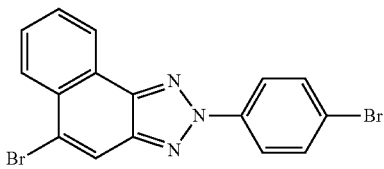 [SMILES: Brc1ccc(-n2nc3cc(Br)c4ccccc4c3n2)cc1]

b) The product from step 2a (49.37 mmol) and copper(II) acetate (0.49 mmol) are placed in a 250 ml flask with a stir bar. 250 ml tert-amyl alcohol is added and the mixture is heated to 80° C. tert-Butyl hydroperoxide, (98.7 mmol) is slowly added and the reaction is monitored by TLC. The flask is cooled to room temperature and the product is filtered. Washing with tert-amyl alcohol and removal of volatiles in vacuo give a light brown solid. The product is triturated in 30 ml methanol overnight, filtered and dried to give an off-white solid (yield: 77.0%). $^1$H-NMR (ppm, CDCl$_3$): 8.47 (m, 1H), 8.20 (d, 1H), 8.08 (d, 2H), 8.01 (s, 1H), 7.58 (m, 2H), 7.49 (d, 2H).

(A-5)

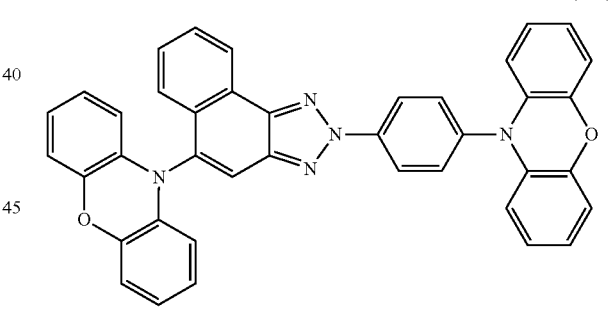

c) The product from example 2b (2.40 mmol), phenoxazine (6.2 mmol), palladium acetate (0.01 mmol), tri-tert-butylphosphine (0.02 mmol), sodium t-buthoxide (7.2 mmol) and 30 ml of toluene are placed in a 100 ml flask. The mixture is stirred at 110° C. overnight and cooled. The mixture is then poured into H$_2$O and extracted with ethylacetate. The organic layer is dried over MgSO$_4$ and concentrated by evaporation. Column chromatography of the crude product with ethylacetate/hexane (1:5) as eluent, followed by reprecipitation from dichloromethane-hexane gives a yellow solid (yield: 53.0%). The product is subsequently purified using zone sublimation. $^1$H-NMR (ppm, CDCl$_3$): 8.73 (d, 1H), 8.61 (d, 2H), 8.35 (s, 1H), 8.06 (d, 1H), 7.75 (m, 3H), 6.82-6.65 (m, 11H), 6.57 (td, 2H), 6.03 (m, 2H), 5.90 (dd, 2H).

Example 3

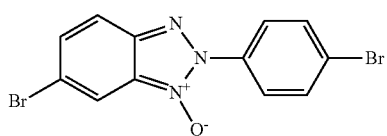 [SMILES: [O-][n+]1c2cc(Br)ccc2nn1-c1ccc(Br)cc1]

4-Bromophenyl hydrazine-HCl (0.39 mol), and NaOAc.3H2O (0.59 mol) are placed in a 1.5 l flask with EtOH 550 ml. While stirring, 1-fluoro-4-bromo-2-nitrobenzene (0.20 mol) is added (by pouring). The slurry becomes slightly orange. The mixture is heated to reflux overnight (20 hours). After cooling to room temperature, the mixture is filtered and washed with EtOH. Without vacuum on the frit, water is added with stirring to dissolve the NaCl and NaF. Vacuum is applied and the process is repeated. Stirring twice with MeOH in the same manner and applying vacuum give a light yellow, crystalline solid. Volatiles are removed in vacuum (yield: 93.4%).

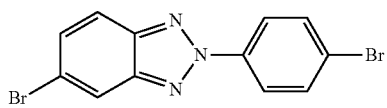 [SMILES: Brc1ccc(-n2nc3ccc(Br)cc3n2)cc1]

b) The product from example 3a (0.11 mol), and sodium hydrogen sulfite (0.11 mol) are placed in a 250 ml 3 neck round balloon with 200 ml DMF. While stirring, the reaction mixture is heated to 110° C. overnight. After cooling to room temperature, the mixture is poured into 300 ml ice water, and then the precipitate is filtered off and washed with 1000 ml water and 500 ml EtOH. Volatiles are removed in vacuum give a slightly beige powder (yield: 93.4%). $^1$H-NMR (ppm, CDCl$_3$): 8.21 (dd, 2H), 8.09 (d, 1H), 7.79 (dd, 1H), 7.67 (dd, 2H), 7.49 (dd, 1H).

(A-6)

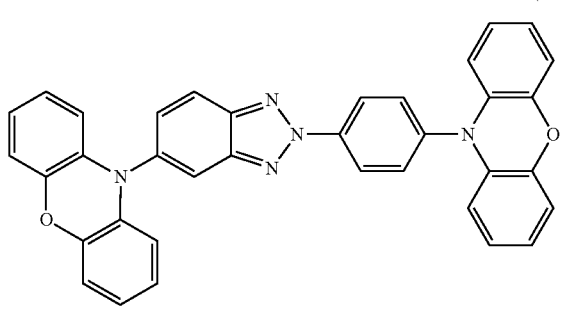

c) The product from example 3b (0.62 mmol), phenoxazine (1.55 mmol), palladium acetate (0.01 mmol), tri-tert-butylphosphine (0.02 mmol), sodium t-buthoxide (1.87 mmol) and 10 ml of toluene are placed in a 50 ml flask. The mixture is stirred at 110° C. overnight and cooled. The mixture is then poured into H$_2$O and extracted with ethylacetate. The organic layer is dried over MgSO$_4$ and concentrated by evaporation. Column chromatography of the crude product with dichloromethane/hexane (1:10) as eluent gives a yellow solid (yield: 30.6%). The product is subsequently purified using zone sublimation. $^1$H-NMR (ppm, CDCl3): 8.60 (d, 2H), 8.35 (d, 1H), 8.29 (d, 1H), 7.75 (d, 2H), 7.49 (dd, 1H), 6.80-6.63 (m, 12H), 6.00 (dd, 4H)

Application Example 1 a) Photoluminescent Characterization in Neat Film

On a silicon substrate, compound (A-5)

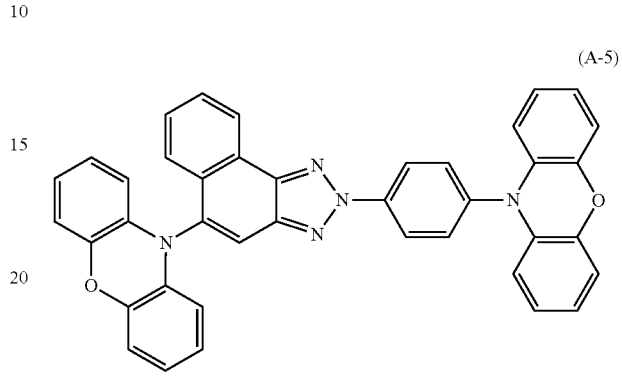

is vacuum-deposited in a thickness of 50 nm. Absorption, fluorescent spectra (excitation at 339 nm) and photoelectron yield spectroscopy of the film are measured, subsequently HOMO and LUMO (eV) of the compound are estimated as 5.76 eV and 3.20 eV, respectively.

b) Photoluminescent Characterization in Host-Guest Film

On a silicon substrate, mCBP doped with 8.6% by weight of compound (A-5) is co-deposited in a thickness of 100 nm. The time-resolved and temperature-dependent emission spectra of the host-guest film are measured by photoluminescence spectroscopy with a streak camera. The prompt (~30 ns) and delayed (>1 μs) fluorescent components and the temperature dependency are observed as shown in FIG. 1 and Table 1. The host-guest film shows an emission peak at 520 nm in PL spectrum (see FIG. 2).

TABLE 1

Temperature dependency of PL emission of codeposited film (mCBP doped with 8.6% by weight of compound (A-5)) (streak camera)

| Temperature (K) | Prompt PL intensity (a.u.) | Delayed PL intensity (a.u.) |
| --- | --- | --- |
| 8 | 0.997 | 0.295 |
| 68 | 0.914 | 0.361 |
| 139 | 0.923 | 0.580 |
| 199 | 0.844 | 0.770 |
| 249 | 0.973 | 0.970 |
| 279 | 1 | 0.999 |
| 198 | 0.975 | 1 |

These results indicate that compound (A-5) is a TADF material.

Application Example 2

An organic light emitting device (OLED) is fabricated by vacuum deposition of ITO (100 nm)/dipyrazino[2,3-f:2',3'-h]quinoxaline-2,3,6,7,10,11-hexacarbonitrile (HAT-CN) (10 nm)/

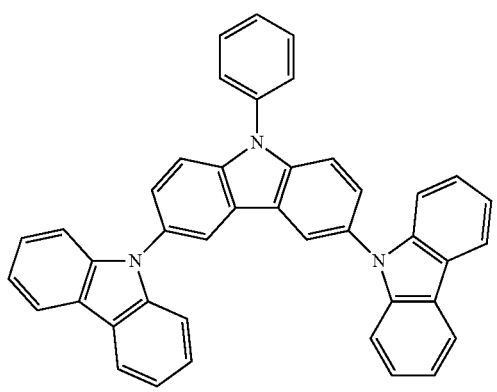 [SMILES: c1ccc(-n2c3ccc(-n4c5ccccc5c5ccccc54)cc3c3cc(-n4c5ccccc5c5ccccc54)ccc32)cc1]

(Tris-PCz, 30 nm)/88.7% by weight 3,3-di(9H-carbazol-9-yl)biphenyl (mCBP):11.3% by weight compound A-5 (30 nm)/2,4,6-tris(biphenyl-3-yl)-1,3,5-triazine (T2T, 10 nm)/

(Bpy-TP2, 40 nm)/LiF (0.8 nm)/Al (100 nm) on a glass substrate, subsequently the device is encapsulated and the performance of the device is evaluated. The device shows an emission peak at 534 nm in electroluminescence (EL) spectrum (see FIG. 2) with an external quantum efficiency (EQE) of 11.1% which is higher than the theoretical value of conventional fluorescent materials (EQE=5-7.5%).

Application Example 3

Application Example 2 is repeated except that compound (A-5) is replaced by compound (A-6) and the emitting layer consists of 90.7% by weight of mCBP and 9.3% by weight of compound (A-6).

Application Example 4

An organic light emitting device (OLED) is fabricated by vacuum deposition of ITO (100 nm)/N-[4-[4-[N-(1-naphthyl)anilino]phenyl]phenyl]-N-phenyl-naphthalen-1-amine (α-NPD, 30 nm)/4-carbazol-9-yl-N,N-bis(4-carbazol-9-yl-phenyl)aniline (TCTA, 20 nm)/[9-(4-tert-butylphenyl)-6-triphenylsilyl-carbazol-3-yl]-triphenyl-silane (CzSi, 10 nm)/ 82% by weight of bis(2-(diphenylphosphino)phenyl)ether oxide (DPEPO): 18% by weight of compound

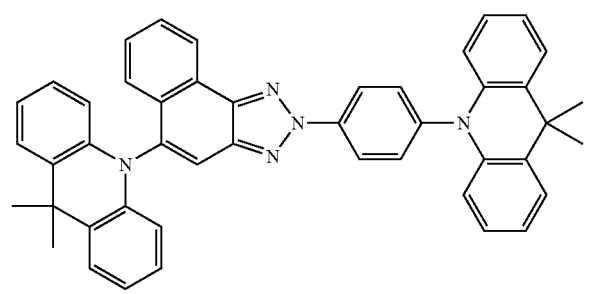

(A-7)

(20 nm)/DPEPO (10 nm)/2-[3,5-bis(1-phenylbenzimidazol-2-yl)phenyl]-1-phenyl-benzimidazole (TPBi, 30 nm)/LiF (0.8 nm)/Al (100 nm) on a glass substrate, subsequently the device is encapsulated and the performance of the device is evaluated.

Application Example 5

Application Example 2 is repeated except that compound A-5 is replaced by compound

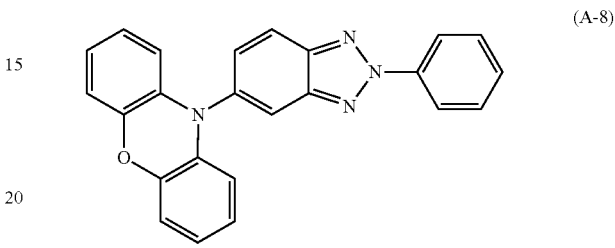

(A-8)

and the emitting layer consists of 87% by weight of mCBP and 13% by weight of compound (A-8).

Application Example 6

Application Example 2 is repeated except that compound A-5 is replaced by compound

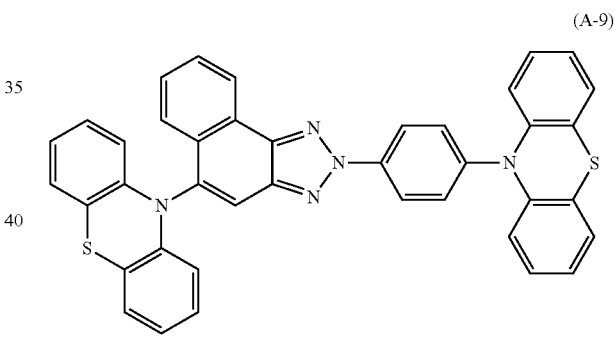

(A-9)

and the emitting layer consists of 88% by weight of mCBP and 12% by weight of compound (A-9).

TABLE 2

EL performance of the devices of Application Examples 3 to 6

| Appl. Example | Emitting compound | EQE (%) | Emission peak (nm) |
|---|---|---|---|
| 3 | A-6 | 11.9 | 569 |
| 4 | A-7 | 15.7 | 516 |
| 5 | A-8 | 7.6 | 543 |
| 6 | A-9 | 14.1 | 542 |

The devices of Application Examples 3 to 6 show emission peaks at 516 to 569 nm in EL spectrum with EQEs of 7.6 to 15.7%, which are higher than the theoretical value of conventional fluorescent materials (EQE=5-7.5%).

The invention claimed is:
1. An organic light-emitting element, comprising a light-emitting layer comprising
   i) a compound of formula

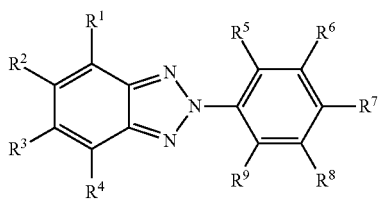

as guest and a host material; or ii) a compound of formula

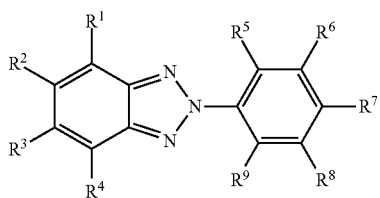   (I)

as host and a fluorescent guest material, wherein

R$^1$, R$^2$, R$^3$ and R$^4$ are independently of each other H, D, F, Cl, a C$_1$-C$_{25}$alkyl group, a C$_1$-C$_{25}$alkoxy group, a C$_6$-C$_{10}$aryloxy group, or a donor group of formula

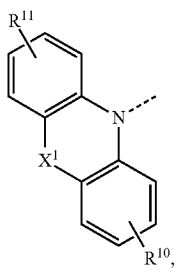

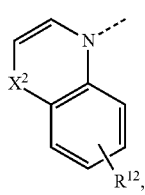

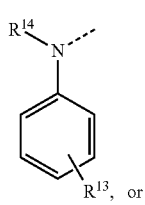

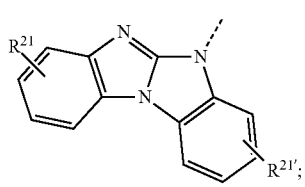

R$^5$, R$^6$, R$^7$, R$^8$ and R$^9$ are independently of each other H, D, F, Cl, a C$_1$-C$_{25}$alkyl group, a C$_1$-C$_{25}$alkoxy group, a C$_6$-C$_{10}$aryloxy group, a group of formula

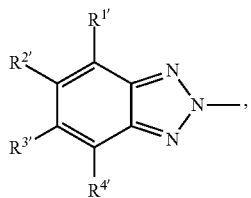

(Xa), (Xb), (Xc), or (Xd);

R$^{1'}$, R$^{2'}$, R$^{3'}$ and R$^{4'}$ are independently of each other H, D, F, Cl, a C$_1$-C$_{25}$alkyl group, a C$_1$-C$_{25}$alkoxy group, or a C$_6$-C$_{10}$aryloxy group; or R$^1$ and R$^2$ together form a group of formula

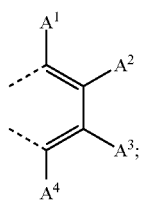

R$^{1'}$ and R$^{2'}$ together form a group of formula

R$^3$ and R$^4$ together form a group of formula

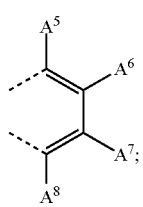

R$^{3'}$ and R$^{4'}$ together form a group of formula

R$^5$ and R$^6$ together form a group of formula

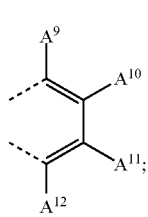

and/or

R$^8$ and R$^9$ together form a group of formula

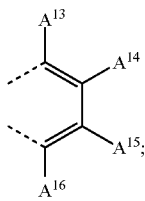

A$^1$, A$^2$, A$^3$, A$^4$, A$^5$, A$^6$, A$^7$ and A$^8$ are independently of each other H, D, F, Cl, a C$_1$-C$_{25}$alkyl group, or a donor group of formula (Xa), (Xb), (Xc), or (Xd);

A$^9$, A$^{10}$, A$^{11}$, A$^{12}$, A$^{13}$, A$^{14}$, A$^{15}$ and A$^{16}$ are independently of each other H, D, F, Cl, a C$_1$-C$_{25}$alkyl group, or a donor group of formula (Xa), (Xb), (Xc), or (Xd);

X$^1$ and X$^2$ are independently of each other a single bond, O, S, N(R$^{15}$), C(=O), C(R$^{16}$)(R$^{17}$), B(R$^{18}$), or Si(R$^{19}$)(R$^{20}$) and R$^{10}$, R$^{11}$, R$^{12}$, R$^{13}$, R$^{21}$ and R$^{21'}$ are independently of each other H, D, F, Cl, or a C$_1$-C$_{25}$alkyl group;

R$^{14}$, R$^{15}$, R$^{16}$, R$^{17}$, R$^{18}$, R$^{19}$ and R$^{20}$ are independently of each other H, D, a C$_1$-C$_{25}$alkyl group, or a C$_6$-C$_{14}$aryl group, which can optionally be substituted by one, or more groups selected from a C$_1$-C$_{25}$alkyl group, a C$_1$-C$_{25}$alkoxy group and a C$_6$-C$_{10}$aryloxy group;

with the proviso that at least one donor group of formula (Xc) is present in the compound of formula (I); characterized in that it emits delayed fluorescence.

2. The organic light-emitting element according to claim 1, wherein

R$^1$, R$^2$, R$^3$, R$^4$, R$^6$, R$^7$, R$^8$ and R$^9$ are independently of each other H, a C$_1$-C$_{25}$alkyl group, a C$_1$-C$_{25}$alkoxy group, a C$_6$-C$_{10}$aryloxy group, a donor group of formula

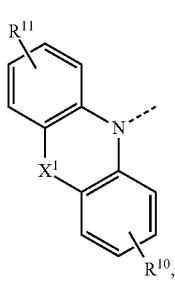

(Xa)

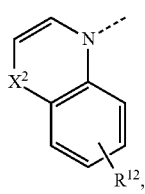

(Xb)

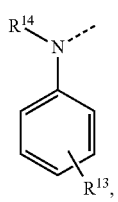

(Xc)

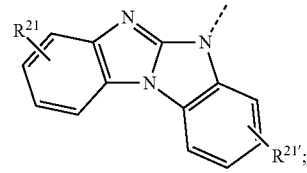

(Xd)

or

R$^1$ and R$^2$ together form a group of formula

and/or

R$^8$ and R$^9$ together form a group of formula

R$^5$ is H, a C$_1$-C$_{25}$alkyl group, a group of formula

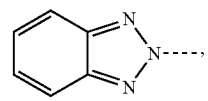

or a donor group of formula (Xa), (Xb), (Xc), or (Xd);

X$^1$ and X$^2$ are independently of each other a single bond, O, S, C(O), N(R$^{15}$), or C(R$^{16}$)(R$^{17}$); and R$^{10}$, R$^{11}$, R$^{12}$, R$^{13}$, R$^{21}$ and R$^{21'}$ are independently of each other H, or a C$_1$-C$_{25}$alkyl group;

R$^{14}$ and R$^{15}$ are independently of each other a group of formula

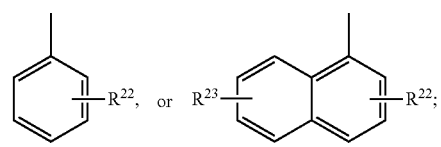

R$^{16}$ and R$^{17}$ are independently of each other H, a C$_1$-C$_{25}$alkyl group;

R$^{22}$ and R$^{23}$ are independently of each other H, a C$_1$-C$_{25}$alkyl group, a C$_1$-C$_{25}$alkoxy group, or a C$_6$-C$_{10}$aryloxy group;

with the proviso that at least one of R$^1$, R$^2$, R$^3$, R$^4$, R$^5$, R$^6$, R$^7$, R$^8$ and R$^9$ is a donor group of formula (Xc).

3. The organic light-emitting element according to claim 1, wherein the compound of formula (I) is a compound of formula (Ia)

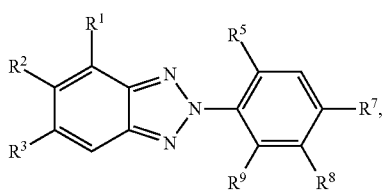

wherein $R^1$ and $R^2$ are independently of each other H, or a $C_1$-$C_{25}$alkyl group, or $R^1$ and $R^2$ together form a group of formula

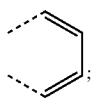

$R^3$, $R^7$ and $R^8$ are independently of each other H, a $C_1$-$C_{25}$alkyl group, or a donor group of formula (Xa)

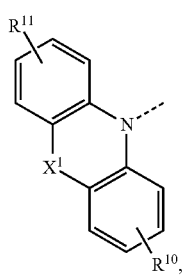

(Xb)

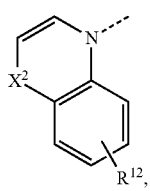

(Xc)

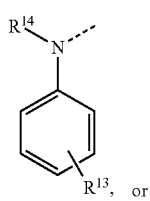

(Xd)

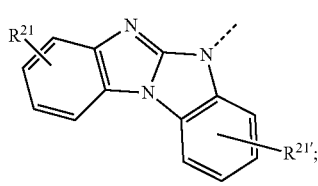

$R^5$ is H, a $C_1$-$C_{25}$alkyl group, a group of formula

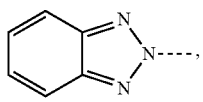

or a donor group of formula (Xa), (Xb), (Xc), or (Xd);

$R^9$ is H, or $R^8$ and $R^9$ together form a group of formula

$X^1$ and $X^2$ are independently of each other a single bond, O, S, N($R^{15}$), or C($R^{16}$)($R^{17}$);

$R^{10}$, $R^{11}$, $R^{12}$, $R^{13}$, $R^{21}$ and $R^{21'}$ are independently of each other H, or a $C_1$-$C_{25}$alkyl group;

$R^{14}$ and $R^{15}$ are independently of each other a group of formula

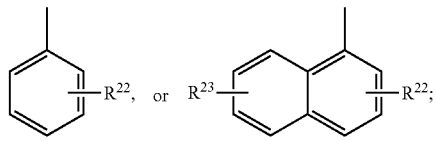

$R^{16}$ and $R^{17}$ are independently of each other H, a $C_1$-$C_{25}$alkyl group;

$R^{22}$ and $R^{23}$ are independently of each other H, or a $C_1$-$C_{25}$alkyl group;

with the proviso that at least one of $R^3$, $R^5$ and $R^7$ is a donor group of formula (Xc).

4. The organic light-emitting element according to claim 1, wherein the compound of formula (I) is a compound of formula (Ia')

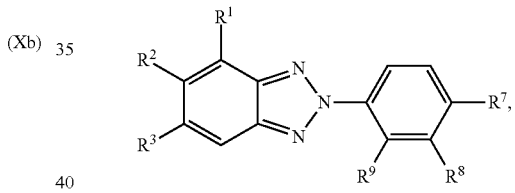

wherein $R^1$ and $R^2$ are independently of each other H, or a $C_1$-$C_{25}$alkyl group, or $R^1$ and $R^2$ together form a group of formula

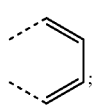

$R^3$ is H, a $C_1$-$C_{25}$alkyl group, or a donor group of formula (Xa)

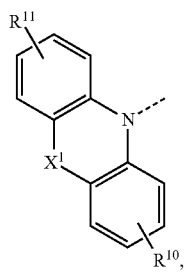

-continued

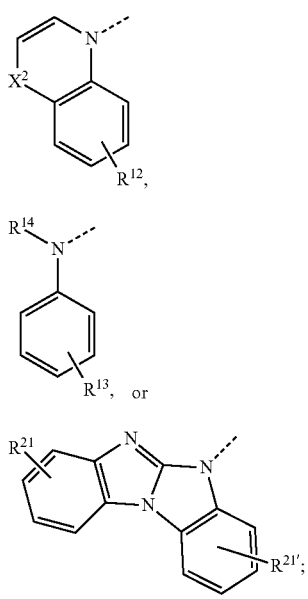

$R^7$ is H, a $C_1$-$C_{25}$alkyl group, or a donor group of formula (Xa), (Xb), (Xc), or (Xd);
$R^8$ and $R^9$ are H, or
$R^8$ and $R^9$ together form a group of formula

$X^1$ and $X^2$ are independently of each other a single bond, O, S, $N(R^{15})$, or $C(R^{16})(R^{17})$;
$R^{10}$, $R^{11}$, $R^{12}$, $R^{13}$, $R^{21}$ and $R^{21'}$ are independently of each other H, or a $C_1$-$C_{25}$alkyl group;
$R^{14}$ and $R^{15}$ are independently of each other a group of formula

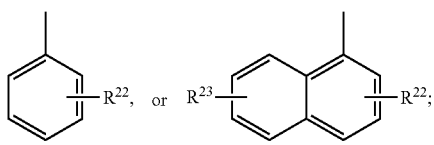

$R^{16}$ and $R^{17}$ are independently of each other H, a $C_1$-$C_{25}$alkyl group;
$R^{22}$ and $R^{23}$ are independently of each other H, or a $C_1$-$C_{25}$alkyl group;
with the proviso that at least one of $R^3$ and $R^7$ is a donor group of formula (Xc).

5. The organic light-emitting element according to claim 1, wherein the compound of formula (I) is a compound of formula

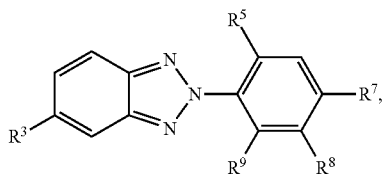

(Ia″)

wherein
$R^3$ and $R^5$ are H and $R^7$ is a donor group of formula

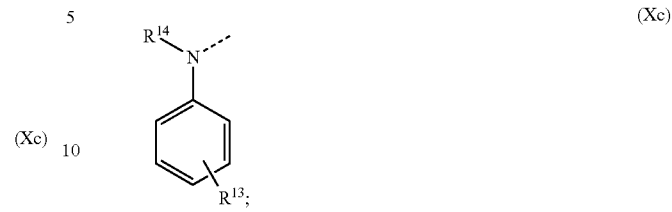

$R^3$ and $R^5$ are H and $R^7$ is a donor group of formula (Xc); or
$R^3$ is a donor group of formula (Xc) and $R^5$ and $R^7$ are H; or
$R^5$ is a donor group of formula (Xc) and $R^3$ and $R^7$ are H; or
$R^3$ and $R^7$ are a donor group of formula (Xc) and $R^5$ is H; or

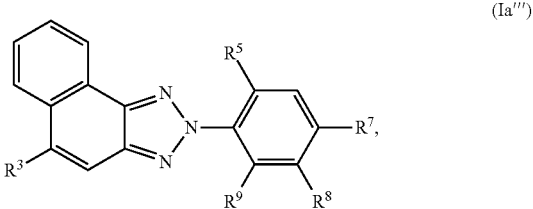

(Ia‴)

wherein
$R^3$ and $R^5$ are H and $R^7$ is a donor group of formula (Xc); or
$R^3$ is a donor group of formula (Xc) and $R^5$ and $R^7$ are H; or
$R^5$ is a donor group of formula (Xc) and $R^3$ and $R^7$ are H; or
$R^3$ and $R^7$ are a donor group of formula (Xc) and $R^5$ is H; and
$R^8$ and $R^9$ are H, or
$R^8$ and $R^9$ together form a group of formula

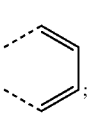

$R^{13}$ are independently of each other H, or a $C_1$-$C_{25}$alkyl group;
$R^{14}$ is a group of formula

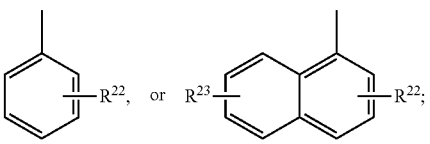

and
$R^{22}$ and $R^{23}$ are independently of each other H, or a $C_1$-$C_{25}$alkyl group.

6. The organic light-emitting element according to claim 5, wherein the compound of formula (I) is a compound of formula (Ia″), wherein $R^5$, $R^8$ and $R^9$ are H;
$R^3$ is H and $R^7$ is a donor group of formula

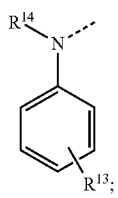 (Xc)

or
$R^3$ is a donor group of formula (Xc) and $R^7$ is H; or
$R^3$ and $R^7$ are a donor group of formula (Xc); or
a compound of formula (Ia''), wherein
$R^5$ is H;
$R^8$ and $R^9$ together form a group of formula

;

$R^3$ is H and $R^7$ is a donor group of formula (Xc); or
$R^3$ is a donor group of formula (Xc) and $R^7$ is H; or
$R^3$ and $R^7$ are a donor group of formula (Xc); or
a compound of formula (Ia''), wherein
$R^3$, $R^7$, $R^8$ and $R^9$ are H;
$R^5$ is a donor group of formula (Xc); or
a compound of formula (Ia'''), wherein
$R^5$, $R^8$ and $R^9$ are H;
$R^3$ is H and $R^7$ is a donor group of formula (Xc); or
$R^3$ is a donor group of formula (Xc) and $R^7$ is H; or
$R^3$ and $R^7$ are a donor group of formula (Xc); or
a compound of formula (Ia'''), wherein
$R^5$ is H;
$R^8$ and $R^9$ together form a group of formula

;

$R^3$ is H and $R^7$ is a donor group of formula (Xc); or
$R^3$ is a donor group of formula (Xc) and $R^7$ is H; or
$R^3$ and $R^7$ are a donor group of formula formula (Xc); or
a compound of formula (Ia'''), wherein
$R^3$, $R^7$, $R^8$ and $R^9$ are H;
$R^5$ is a donor group of formula (Xc);
$R^{13}$ are independently of each other H, or a $C_1$-$C_{25}$alkyl group;
$R^{14}$ is a group of formula

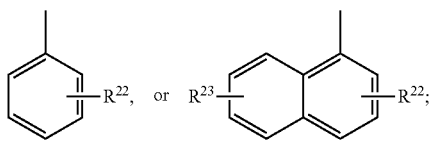

and
$R^{22}$ and $R^{23}$ are independently of each other H, or a $C_1$-$C_{25}$alkyl group.

7. The organic light-emitting element according to claim 3, wherein the compound of formula (I) is a compound of formula

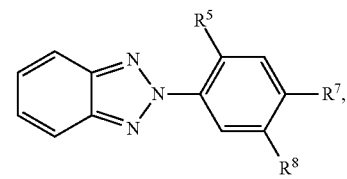 (Ib)

wherein
$R^5$ is a group of formula

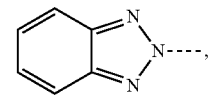, $R^7$ and $R^8$ are a donor group of formula

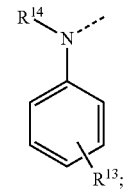 (Xc)

or
a compound of formula (Ib), wherein
$R^5$ is a donor group of formula (Xc), and
$R^7$ and $R^8$ are independently of each other H, or a $C_1$-$C_{25}$alkyl group;
$R^{13}$ are independently of each other H, or a $C_1$-$C_{25}$alkyl group;
$R^{14}$ is a group of formula

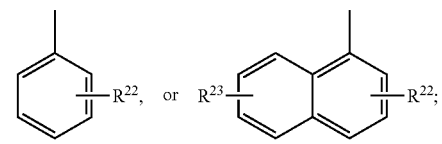;

and
$R^{22}$ and $R^{23}$ are independently of each other H, or a $C_1$-$C_{25}$alkyl group.

8. The organic light-emitting element according to claim 1, wherein the compound of formula (I) is a compound of formula

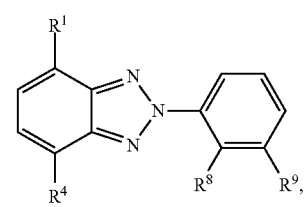 (Ic)

wherein
R¹ and R⁴ are a donor group of formula

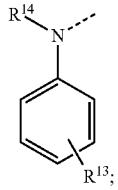
(Xc)

R⁸ and R⁹ are H, or
R⁸ and R⁹ together form a group of formula

;

R¹³ are independently of each other H, or a $C_1$-$C_{25}$alkyl group;
R¹⁴ is a group of formula

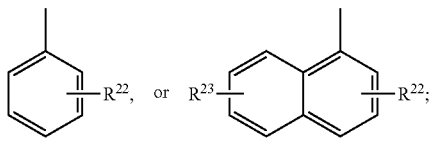

and
R²² and R²³ are independently of each other H, or a $C_1$-$C_{25}$alkyl group.

9. The organic light-emitting element according to claim 1, wherein the donor group is a donor group of formula (Xc), wherein R¹³ is a group of formula

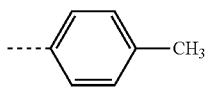

and R¹⁴ is a group of formula

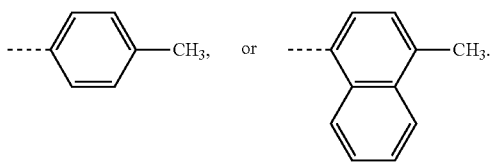

10. The organic light-emitting element according to claim 1, wherein the donor group is a group of formula

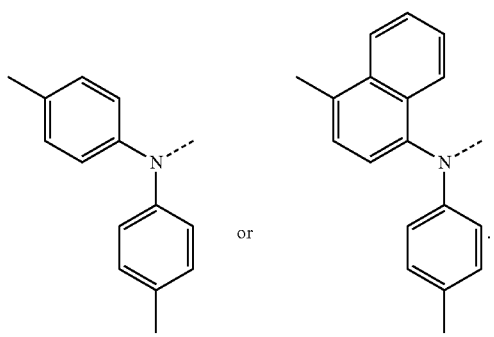

11. A compound of formula

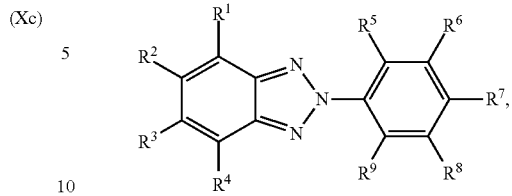
(I)

wherein
R¹, R², R³ and R⁴ are independently of each other H, D, F, Cl, a $C_1$-$C_{25}$alkyl group, a $C_1$-$C_{25}$alkoxy group, a $C_6$-$C_{10}$aryloxy group, or a donor group of formula

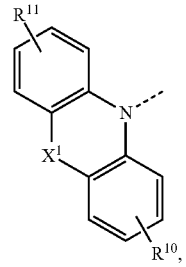
(Xa)

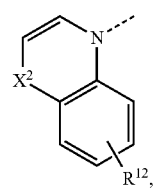
(Xb)

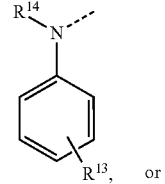
(Xc)

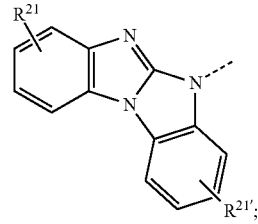
(Xd)

R⁵, R⁶, R⁷, R⁸ and R⁹ are independently of each other H, D, F, Cl, a $C_1$-$C_{25}$alkyl group, a $C_1$-$C_{25}$alkoxy group, a $C_6$-$C_{10}$aryloxy group, a group of formula

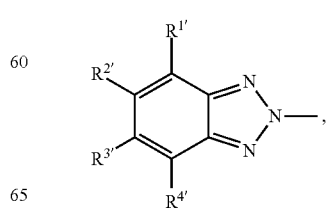

(Xa), (Xb), (Xc), or (Xd);

$R^1$, $R^2$, $R^{3'}$ and $R^{4'}$ are independently of each other H, D, F, Cl, a $C_1$-$C_{25}$alkyl group, a $C_1$-$C_{25}$alkoxy group, or a $C_6$-$C_{10}$aryloxy group, or;

$R^1$ and $R^2$ together form a group of formula

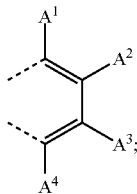

$R^{1'}$ and $R^{2'}$ together form a group of formula

$R^3$ and $R^4$ together form a group of formula

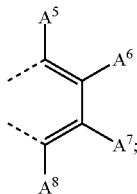

$R^{3'}$ and $R^{4'}$ together form a group of formula

$R^5$ and $R^6$ together form a group of formula

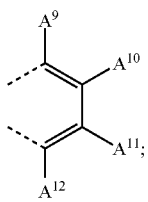

and/or $R^8$ and $R^9$ together form a group of formula

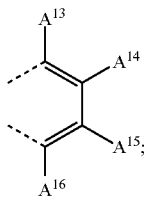

$A^1$, $A^2$, $A^3$, $A^4$, $A^5$, $A^6$, $A^7$ and $A^8$ are independently of each other H, D, F, Cl, a $C_1$-$C_{25}$alkyl group, or a donor group of formula (Xa), (Xb), (Xc), or (Xd);

$A^9$, $A^{10}$, $A^{11}$, $A^{12}$, $A^{13}$, $A^{14}$, $A^{15}$ and $A^{16}$ are independently of each other H, D, F, Cl, a $C_1$-$C_{25}$alkyl group, or a donor group of formula (Xa), (Xb), (Xc), or (Xd);

$X^1$ and $X^2$ are independently of each other O, S, $N(R^{15})$, $C(R^{16})(R^{17})$, $B(R^{18})$, or $Si(R^{19})(R^{20})$ and $R^{10}$, $R^{11}$, $R^{12}$, $R^{13}$, $R^{21}$ and $R^{21'}$ are independently of each other H, D, F, Cl, or a $C_1$-$C_{25}$alkyl group;

$R^{15}$, $R^{16}$, $R^{17}$, $R^{18}$, $R^{19}$ and $R^{20}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group;

$R^{14}$ is a $C_6$-$C_{14}$arly group substituted by one or more groups selected from a $C_1$-$C_{25}$alkyl group, a $C_1$-$C_{25}$alkoxy group and a $C_6$-$C_{10}$aryloxy group;

with the proviso that at least one donor group of formula (Xc) is present in the compound of formula (I).

12. The compound according to claim 11, wherein $R^1$, $R^2$, $R^3$, $R^4$, $R^6$, $R^7$, $R^8$ and $R^9$ are independently of each other H, a $C_1$-$C_{25}$alkyl group, a $C_1$-$C_{25}$alkoxy group, a $C_6$-$C_{10}$aryloxy group, a donor group of formula

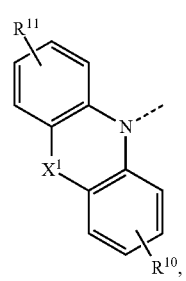
(Xa)

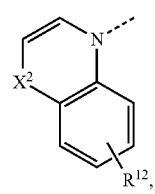
(Xb)

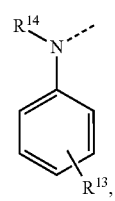
(Xc)

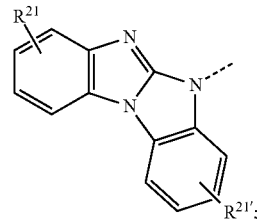
(Xd)

or $R^1$ and $R^2$ together form a group of formula

and/or $R^8$ and $R^9$ together form a group of formula

;

$R^5$ is H, a $C_1$-$C_{25}$alkyl group, a group of formula

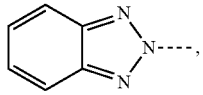, or a donor group of formula (Xa), (Xb), (Xc), or (Xd);

$X^1$ and $X^2$ are independently of each other O, S, N($R^{15}$), or C($R^{16}$)($R^{17}$); and $R^{10}$, $R^{11}$, $R^{12}$, $R^{21}$ and $R^{21'}$ are independently of each other H, or a $C_1$-$C_{25}$alkyl group;

$R^{15}$ is a group of formula

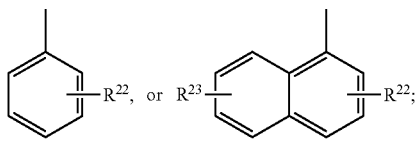

$R^{16}$ and $R^{17}$ are independently of each other H, a $C_1$-$C_{25}$alkyl group;

$R^{22}$ and $R^{23}$ are independently of each other H, a $C_1$-$C_{25}$alkyl group, a $C_1$-$C_{25}$alkoxy group, or a $C_6$-$C_{10}$aryloxy group;

with the proviso that at least one of $R^1$, $R^2$, $R^3$, $R^4$, $R^5$, $R^6$, $R^7$, $R^8$ and $R^9$ is a donor group of formula (Xc).

13. The compound according to claim 11, wherein the compound of formula (I) is a compound of formula

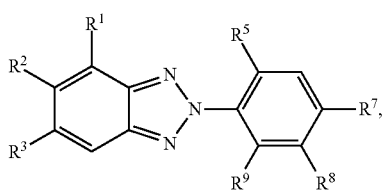 (Ia)

wherein $R^1$ and $R^2$ are independently of each other H, or a $C_1$-$C_{25}$alkyl group, or $R^1$ and $R^2$ together form a group of formula

;

$R^3$, $R^7$ and $R^8$ are independently of each other H, a $C_1$-$C_{25}$alkyl group, or a donor group of formula

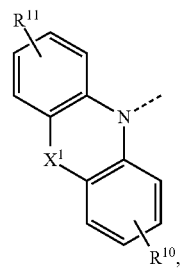 (Xa)

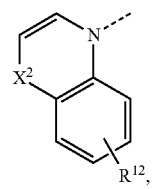 (Xb)

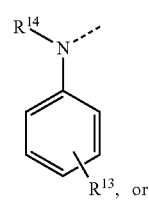 (Xc)

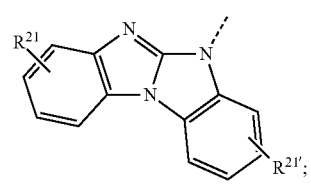 (Xd)

$R^5$ is H, a $C_1$-$C_{25}$alkyl group, a group of formula

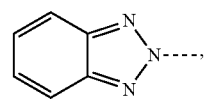, or a donor group of formula (Xa), (Xb), (Xc), or (Xd);

$R^9$ is H, or $R^8$ and $R^9$ together form a group of formula

;

$X^1$ and $X^2$ are independently of each other O, S, N($R^{15}$), or C($R^{16}$)($R^{17}$);

$R^{10}$, $R^{11}$, $R^{12}$, $R^{13}$, $R^{21}$ and $R^{21'}$ are independently of each other H, or a $C_1$-$C_{25}$alkyl group;

$R^{14}$ is a group of formula

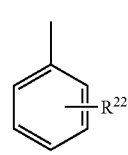

and $R^{22}$ is a $C_1$-$C_{25}$alkyl group, or $R^{14}$ is a group of formula

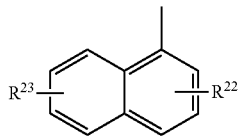

and $R^{22}$ and $R^{23}$ are independently of each other H or a $C_1$-$C_{25}$alkyl group, wherein at least one of $R^{22}$ and $R^{23}$ is a $C_1$-$C_{25}$alkyl group;

$R^{15}$ is a group of formula

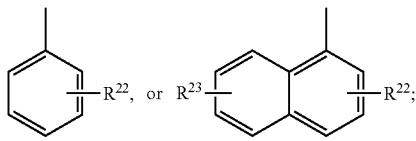

wherein $R^{22}$ and $R^{23}$ are independently of each other H, or a $C_1$-$C_{25}$alkyl group;

$R^{16}$ and $R^{17}$ are independently of each other H, a $C_1$-$C_{25}$alkyl group;

with the proviso that at least one of $R^3$, $R^5$ and $R^7$ is a donor group of formula (Xc).

14. The compound according to claim 13, which is a compound of formula

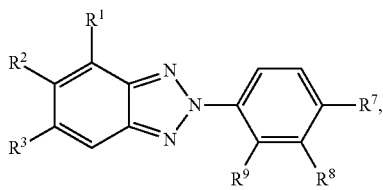

(Ia')

wherein $R^1$ and $R^2$ are independently of each other H, or a $C_1$-$C_{25}$alkyl group, or $R^1$ and $R^2$ together form a group of formula

$R^3$ is H, a $C_1$-$C_{25}$alkyl group, or a donor group of formula (Xa)

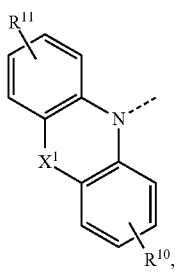

(Xb)

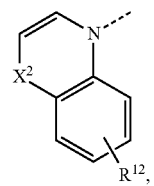

(Xc)

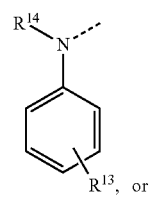

or (Xd)

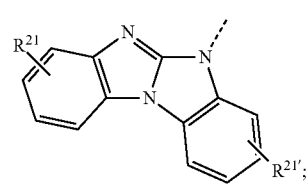

$R^7$ is H, a $C_1$-$C_{25}$alkyl group, or a donor group of formula (Xa), (Xb), (Xc), or (Xd);

$R^8$ and $R^9$ are H, or $R^8$ and $R^9$ together form a group of formula

$X^1$ and $X^2$ are independently of each other O, S, $N(R^{15})$, or $C(R^{16})(R^{17})$;

$R^{10}$, $R^{11}$, $R^{12}$, $R^{13}$, $R^{21}$ and $R^{21'}$ are independently of each other H, or a $C_1$-$C_{25}$alkyl group;

$R^{14}$ is a group of formula

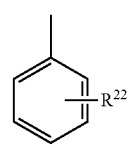

and $R^{22}$ is a $C_1$-$C_{25}$alkyl group, or $R^{14}$ is a group of formula

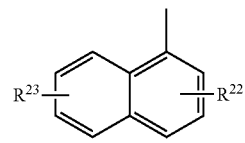

and $R^{22}$ and $R^{23}$ are independently of each other H, or a $C_1$-$C_{25}$alkyl group, wherein at least one of $R^{22}$ and $R^{23}$ is a $C_1$-$C_{25}$alkyl group;

$R^{15}$ is a group of formula

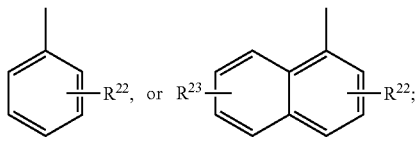

wherein $R^{22}$ and $R^{23}$ are independently of each other H, or a $C_1$-$C_{25}$alkyl group;
$R^{16}$ and $R^{17}$ are independently of each other H, a $C_1$-$C_{25}$alkyl group;
with the proviso that at least one of $R^3$ and $R^7$ is a donor group of formula (Xc).

15. The compound according to claim 13, which is a compound of formula

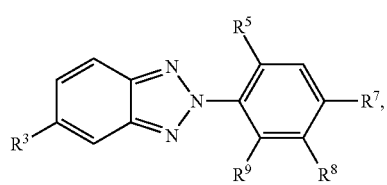 (Ia″)

wherein
$R^3$ and $R^5$ are H and $R^7$ is a donor group of formula

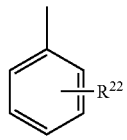 (Xc)

or
$R^3$ is a donor group of formula (Xc) and $R^5$ and $R^7$ are H; or
$R^5$ is a donor group of formula (Xc) and $R^3$ and $R^7$ are H; or
$R^3$ and $R^7$ are a donor group of formula (Xc) and $R^5$ is H; or

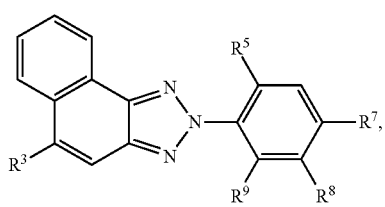 (Ia‴)

wherein
$R^3$ and $R^5$ are H and $R^7$ is a donor group of formula (Xc); or
$R^3$ is a donor group of formula (Xc) and $R^5$ and $R^7$ are H; or
$R^5$ is a donor group of formula (Xc) and $R^3$ and $R^7$ are H; or $R^3$ and $R^7$ are a donor group of formula (Xc) and $R^5$ is H;
$R^8$ and $R^9$ are H, or
$R^8$ and $R^9$ together form a group of formula

$R^{13}$ are independently of each other H, or a $C_1$-$C_{25}$alkyl group;
$R^{14}$ is a group of formula

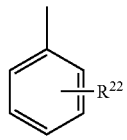

and $R^{22}$ is a $C_1$-$C_{25}$alkyl group, or $R^{14}$ is a group of formula

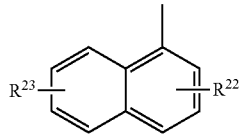

and $R^{22}$ and $R^{23}$ are independently of each other H, or a $C_1$-$C_{25}$alkyl group, wherein at least one of $R^{22}$ and $R^{23}$ is a $C_1$-$C_{25}$alkyl group.

16. The compound according to claim 15, wherein the compound of formula (I) is a compound of formula (Ia″), wherein
$R^5$, $R^8$ and $R^9$ are H;
$R^3$ is H and $R^7$ is a donor group of formula

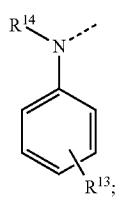 (Xc)

or
$R^3$ is a donor group of formula (Xc) and $R^7$ is H; or
$R^3$ and $R^7$ are a donor group of formula (Xc); or
a compound of formula (Ia‴), wherein
$R^5$, $R^8$ and $R^9$ are H;
$R^3$ is H and $R^7$ is a donor group of formula (Xc); or
$R^3$ is a donor group of formula (Xc) and $R^7$ is H; or
$R^3$ and $R^7$ are a donor group of formula formula (Xc);
$R^{13}$ are independently of each other H, or a $C_1$-$C_{25}$alkyl group;

$R^{14}$ is a group of formula

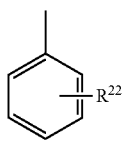

and $R^{22}$ is a $C_1$-$C_{25}$alkyl group, or $R^{14}$ is a group of formula

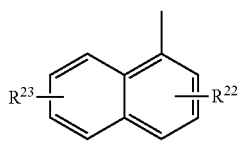

and $R^{22}$ and $R^{23}$ are independently of each other H, or a $C_1$-$C_{25}$alkyl group, wherein at least one of $R^{22}$ and $R^{23}$ is a $C_1$-$C_{25}$alkyl group.

17. The compound according to claim 13, wherein the compound of formula (I) is a compound of formula (Ib)

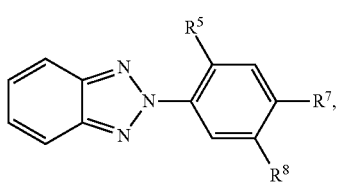

wherein
$R^5$ is a group of formula

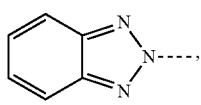

$R^7$ and $R^8$ are a donor group of formula (Xc)

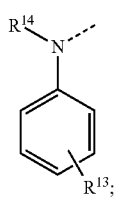

or
a compound of formula (Ib), wherein
$R^5$ is a donor group of formula (Xc), and
$R^7$ and $R^8$ are independently of each other H, or a $C_1$-$C_{25}$alkyl group;
$R^{13}$ are independently of each other H, or a $C_1$-$C_{25}$alkyl group;

$R^{14}$ is a group of formula

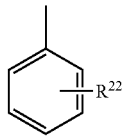

and $R^{22}$ is a $C_1$-$C_{25}$alkyl group, or $R^{14}$ is a group of formula

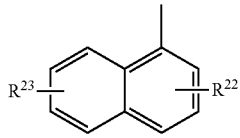

and $R^{22}$ and $R^{23}$ are independently of each other H, or a $C_1$-$C_{25}$alkyl group, wherein at least one of $R^{22}$ and $R^{23}$ is a $C_1$-$C_{25}$alkyl group.

18. The compound according to claim 11, wherein the compound of formula (I) is a compound of formula (Ic)

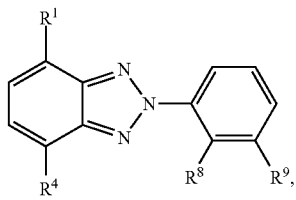

wherein
$R^1$ and $R^4$ are a donor group of formula (Xc)

$R^8$ and $R^9$ are H, or
$R^8$ and $R^9$ together form a group of formula

$R^{13}$ are independently of each other H, or a $C_1$-$C_{25}$alkyl group;
$R^{14}$ is a group of formula

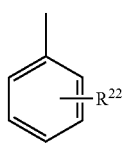

and $R^{22}$ is a $C_1$-$C_{25}$alkyl group, or $R^{14}$ is a group of formula

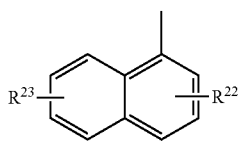

and $R^{22}$ and $R^{23}$ are independently of each other H, or a $C_1$-$C_{25}$alkyl group, wherein at least one of $R^{22}$ and $R^{23}$ is a $C_1$-$C_{25}$alkyl group.

19. The compound according to claim 11, wherein the donor group is a donor group of formula (Xc), wherein $R^{13}$ is a group of formula

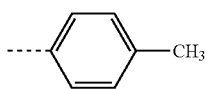

and $R^{14}$ is a group of formula

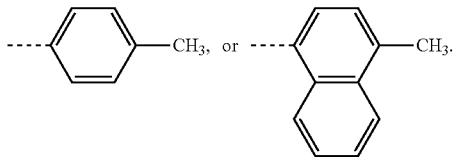

20. The compound according to claim 11, wherein the donor group is a group of formula

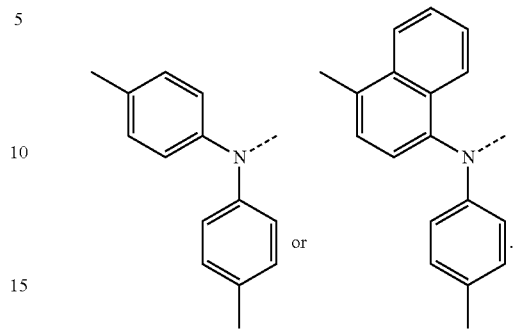

21. A light-emitting layer comprising the compound according to claim 11.

22. An organic light emitting element, comprising the compound according to claim 11.

* * * * *